(12) United States Patent
Cleverly et al.

(10) Patent No.: US 9,597,285 B2
(45) Date of Patent: Mar. 21, 2017

(54) EXTRUDED CHEWABLE FORMULATION COMPRISING BOUND WATER

(71) Applicant: Argenta Manufacturing Limited, Auckland (NZ)

(72) Inventors: Douglas Robert Cleverly, Auckland (NZ); David Anthony Gill, Auckland (NZ); Keryn Davies, Auckland (NZ); Priyanka Agarwal, Auckland (NZ); Su Win, Auckland (NZ); Gopinath Devaraj, Auckland (NZ)

(73) Assignee: Argenta Manufacturing Limited, Auckland (NZ)

( * ) Notice: Subject to any disclaimer, the term of this patent is extended or adjusted under 35 U.S.C. 154(b) by 0 days.

(21) Appl. No.: 15/064,450

(22) Filed: Mar. 8, 2016

(65) Prior Publication Data

US 2016/0184223 A1 Jun. 30, 2016

Related U.S. Application Data

(63) Continuation of application No. 14/656,667, filed on Mar. 12, 2015, now Pat. No. 9,314,478, which is a (Continued)

(51) Int. Cl.
*A61K 9/68* (2006.01)
*A61K 9/00* (2006.01)
(Continued)

(52) U.S. Cl.
CPC ............ *A61K 9/0056* (2013.01); *A23K 20/10* (2016.05); *A23K 20/158* (2016.05); *A23K 20/168* (2016.05); *A23K 20/179* (2016.05); *A23K 20/195* (2016.05); *A23K 40/10* (2016.05); *A23K 40/20* (2016.05); *A23K 40/30* (2016.05); *A23K 50/42* (2016.05); *A61K 9/0058* (2013.01); *A61K 9/145* (2013.01); *A61K 9/146* (2013.01);
(Continued)

(58) Field of Classification Search
CPC .................................................... A61K 9/0058
See application file for complete search history.

(56) References Cited

U.S. PATENT DOCUMENTS

2013/0203692 A1* 8/2013 Soll ...................... A61K 45/06
514/30

\* cited by examiner

*Primary Examiner* — Carlos Azpuru
(74) *Attorney, Agent, or Firm* — Tracey S. Truitt; Poisinelli PC

(57) ABSTRACT

The present invention relates to a chewable formulation for delivering a nutritional or pharmaceutically active agent to an animal target. The chewable formulation comprises a nutritional ingredient or an effective amount of a pharmaceutically active agent, and a plasticizer. The chewable formulation is formed by extrusion and the formulation contains substantially no unbound water, nor is any water added in the manufacturing process. The present invention also relates to a method of manufacturing a shelf stable chewable formulation which comprises mixing the nutritional or pharmaceutically active agent with a fat, lipid or fat and lipid to obtain a first composition, adding one or more plasticizers to the first mixture to obtain a second composition, extruding the second composition at a temperature sufficient to melt the fat and lipid, and allowing the extruded second composition to cool to room temperature thereby providing the chewable formulation.

37 Claims, 2 Drawing Sheets

Related U.S. Application Data continuation of application No. PCT/IB2014/059911, filed on Mar. 17, 2014.

(60) Provisional application No. 61/793,676, filed on Mar. 15, 2013.

(51) Int. Cl.
| | |
|---|---|
| *A61K 9/14* | (2006.01) |
| *A61K 9/50* | (2006.01) |
| *A61K 31/138* | (2006.01) |
| *A61K 31/166* | (2006.01) |
| *A61K 31/35* | (2006.01) |
| *A61K 31/404* | (2006.01) |
| *A61K 31/4184* | (2006.01) |
| *A61K 31/4985* | (2006.01) |
| *A61K 31/506* | (2006.01) |
| *A61K 31/5415* | (2006.01) |
| *A61K 31/573* | (2006.01) |
| *A61K 31/7048* | (2006.01) |

(52) U.S. Cl.
CPC ............ *A61K 9/148* (2013.01); *A61K 9/5015* (2013.01); *A61K 9/5089* (2013.01); *A61K 31/138* (2013.01); *A61K 31/166* (2013.01); *A61K 31/35* (2013.01); *A61K 31/404* (2013.01); *A61K 31/4184* (2013.01); *A61K 31/4985* (2013.01); *A61K 31/506* (2013.01); *A61K 31/5415* (2013.01); *A61K 31/573* (2013.01); *A61K 31/7048* (2013.01)

EXTRUDED CHEWABLE FORMULATION COMPRISING BOUND WATER

INCORPORATION BY REFERENCE

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a chewable formulation containing substantially no water in an unbound state. The present invention also relates to a method of manufacturing a chewable formulation by extrusion without the addition of water.

BACKGROUND TO THE INVENTION

Chewable formulations are useful for the delivery of nutritional and pharmaceutically active ingredients. Such formulations are typically produced by extrusion.

Water is a vital ingredient in chewable treats manufactured by the extrusion process, as shown in the following patents.

US 2005/013714 uses natural meat flavouring, partially gelatinized starch, softener and 9% water. NZ 580357 uses a gelatinized functional protein matrix with 0.5-40% water and water activity in range of 0.6-0.8.

NZ 580333 uses water or aqueous sorbitol used as granulating fluid. U.S. Pat. No. 7,390,520 contains 8-18% water and 56-80% dry wheat gluten. US 2005/013714 uses natural meat flavouring, partially gelatinized starch, softener and 9% water.

NZ 580357 uses a gelatinized functional protein matrix with 0.5-40% water and water activity in range of 0.6-0.8. NZ 580333 uses water or aqueous sorbitol used as granulating fluid. U.S. Pat. No. 7,390,520 contains 8-18% water and 56-80% dry wheat gluten.

High levels of water in chewable treat formulations can lead to a number of problems. Problems include, for example, microbial contamination and drying of the chew on storage. The presence of water may also cause the degradation of active ingredients, which may affect the stability, efficacy, and safety of the product during its shelf life.

Conversely, low levels of water may yield dry or crumbly products that may have poor texture in the mouth and may also be susceptible to disintegration during handling and shipping. Extrusion may also be difficult.

Chewable formulations must be palatable to the animal to which they intended to be delivered. However, providing a formulation that is palatable and has acceptable shelf life can be challenging.

There is an ongoing need for new chewable formulations that avoid one or more of the disadvantages associated with existing chewable formulations.

It is an object of the present invention to go at least some way to meeting this need; and/or to at least provide the public with a useful choice.

SUMMARY OF THE INVENTION

In one aspect the invention relates to a shelf stable chewable formulation comprising
 a nutritional or pharmaceutically active agent,
 a plasticiser, and
 wherein the formulation is formed by extrusion and the formulation contains substantially no unbound water.

In another aspect the invention relates to a shelf stable chewable formulation comprising
 a nutritional or pharmaceutically active agent,
 a plasticiser, and
 wherein the formulation is formed by extrusion and the manufacturing process of the chewable formulation does not include the addition of water.

In another aspect, the invention relates to a shelf stable chewable formulation comprising
 a nutritional or pharmaceutically active agent,
 a plasticiser, and
 wherein the formulation is formed by extrusion and the formulation has a water activity ($a_w$) of from about 0.1 to about 0.65.

In another aspect, the invention relates to a shelf stable chewable formulation comprising
 a nutritional or pharmaceutically active agent,
 a fat, lipid or fat and lipid,
 a plasticiser, and
 optionally, a non-aqueous solvent or vehicle, and
 wherein the formulation is formed by extrusion and the formulation has a water activity ($a_w$) of from about 0.1 to about 0.65.

In another aspect the invention relates to a method of manufacturing a shelf stable chewable formulation comprising
 mixing a nutritional or pharmaceutically active agent with a fat, lipid or fat and lipid to obtain a first composition,
 optionally adding one or more plasticizers to the first mixture to obtain a second composition, and
 extruding the first composition or second composition under conditions effective to at least partially melt the fat, lipid, or fat and lipid, thereby providing the chewable formulation, and
 wherein the method of manufacture does not include the addition of water.

In another aspect the invention relates to a method of manufacturing a shelf stable chewable formulation comprising
 mixing a nutritional or pharmaceutically active agent with a fat, lipid or fat and lipid to obtain a first composition,
 adding one or more plasticizers to the first mixture to obtain a second composition,
 extruding the second composition at a temperature sufficient to melt the fat and lipid,
 and allowing the extruded second composition to cool to room temperature thereby providing the chewable formulation, and
 wherein the method of manufacture does not include the addition of water.

Any one or more of the following embodiments may relate to any of the above aspects.

In one embodiment, the nutritional active agent is selected from a vitamin, a pro-vitamin, a mineral, a glycosaminoglycan or a nutritionally active monomer thereof, an amino acid, or a co-enzyme, or any combination of any two or more thereof.

In one embodiment, the pharmaceutically active agent is selected from anesthetics, corticosteroids, NSAIDS, antibiotics, antiemetics, anti-thyroidal agents, parasiticidal agents, appetite stimulants, anti-histamines, histamine blockers, anti-fungal agents, antiprotozoal agents, anti-depressants, or steroids, or any combination of any two or more thereof.

In one embodiment the pharmaceutically active agent is selected from anesthetics, corticosteroids, NSAIDS, antibiotics, antiemetics, anti-thyroidal agents or parasiticidal agents, or any combination of any two or more thereof.

In one embodiment, the pharmaceutically active agent selected from corticosteroids, NSAIDS, antiemetics, antihistamines, parasiticidal agents, or anthelmintics, or any combination of any two or more thereof.

In one embodiment, the pharmaceutically active agent is a parasiticidal agent.

In one embodiment the pharmaceutically active agent is an anthelmintic.

In one embodiment the pharmaceutically active agent is an NSAID.

In one embodiment, the pharmaceutically active agent is an antiemetic.

In one embodiment, the pharmaceutically active agent is an antihistamine.

In one embodiment, the pharmaceutically active agent is a corticosteroid.

In one embodiment the nutritional ingredient or pharmaceutically active agent is mixed by dry blending.

In an alternate embodiment the nutritional ingredient or pharmaceutically active agent may be dissolved in an appropriate solvent before addition.

In one embodiment, the nutritional ingredient or pharmaceutically active agent may be dissolved or suspended in a non-aqueous solvent before addition.

In one embodiment the nutritional ingredient or pharmaceutically active agent is granulated before mixing.

In one embodiment the nutritional ingredient or pharmaceutically active agent, optionally in granular form, are coated, or further coated, with a suitable coating.

In one embodiment the coating polymer is selected from polyethylene glycols, a wax, or a fatty acid.

In one embodiment the coating polymer is a saturated $C_{18}$-$C_{22}$ fatty acid. More preferably the fatty acid is stearic acid.

In one embodiment the nutritional ingredient or an effective amount of a pharmaceutically active agent (optionally in granular form) are conjugated with other substances, such as cyclodextrins, surfactants, or solubility or bioavailability enhancers, etc.

In one embodiment the water activity ($a_w$) of the chewable formulation is less than 0.93, 0.92, 0.91, 0.90, 0.89, 0.88, 0.87, 0.86, 0.85, 0.84, 0.83, 0.82, 0.81, 0.80, 0.79, 0.78, 0.77, 0.76, 0.75, 0.74, 0.73, 0.72, 0.71, 0.70, 0.69, 0.68, 0.67, 0.66, 0.65, 0.64, 0.63, 0.62, 0.61, 0.60, 0.59, 0.58, 0.57, 0.56, 0.55, 0.54, 0.53, 0.52, 0.51, 0.50, 0.49, 0.48, 0.47, 0.46, 0.45, 0.44, 0.43, 0.42, 0.41, 0.40, 0.38, 0.37, 0.36, 0.35, 0.34, 0.33, 0.32, 0.31, 0.30, 0.29, 0.28, 0.27, 0.26, 0.25, 0.24, 0.23, 0.22, 0.21, 0.20, 0.19, 0.18, 0.17, 0.16, 0.15, 0.14, 0.13, 0.12, 0.11, 0.10, and useful ranges may be selected between any of these values.

In one embodiment the chewable formulation comprises
a filler, diluent or filler and diluent,
a binder,
a sweetener,
a flavouring agent,
a plasticizer,
a humectant,
a fat, lipid or fat and lipid,
an antioxidant,
a colouring agent,
a disintegrating agent, or
a preservative, buffering agent, or preservative and buffering agent, or
any combination of any two or more thereof.

In one embodiment the chewable formulation comprises
a filler, diluent or filler and diluent,
a binder,
a sweetener,
a flavouring agent,
a plasticizer,
a humectant,
a fat, lipid or fat and lipid,
an antioxidant,
a colouring agent,
a disintegrating agent,
a preservative, buffering agent, or preservative and buffering agent,
a lubricant,
a complexing agent,
a coating agent,
a surfactant,
a solubility enhancer, bioavailability enhancer, or a solubility enhancer and a bioavailability enhancer,
a palatability enhancer, or
a non-aqueous solvent or vehicle, or
any combination of any two or more thereof.

In one embodiment the chewable formulation comprises one or more fillers.

In one embodiment a combination of fillers are used in the formulation. In an alternate embodiment a combination of one or more fillers is used with one or more diluents. In an alternate embodiment a combination of diluents are used in the formulation.

In one embodiment the formulation comprises 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, or 90% by weight filler, diluent or filler and diluent, and useful ranges may be selected between any of these values.

In one embodiment the filler, diluent or filler and diluent are selected from starches and their derivatives (e.g. hydrogenated starch hydrosylate), celluloses and their derivatives (e.g. cellulose acetate), protein matrices (soy protein, dextrates, wheat gluten, whey, corn cob, corn gluten), carbohydrates (e.g. maltodextrin, polydextrose), sugars and sugar alcohols (e.g. glucose, lactose, fructose, maltose, dextrose, sucrose, maltitol, xylitol, isomalt, mannitol), silicates, calcium phosphates, calcium sulfate, dextrates, kaolin, magnesium carbonate, polymethacrylates, talc, or salts (e.g. sodium chloride) or any combination of any two or more thereof.

In one embodiment the formulation comprises about 15% by weight filler, diluent or filler and diluent.

In one embodiment the chewable formulation comprises one or more binders.

In one embodiment the formulation comprises 0.1, 0.2, 0.3, 0.5, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% by weight binder, and useful ranges may be selected between any of these values.

In one embodiment, the formulation comprises 1, 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, or 50% weight binder and/or filler, and useful ranges may be selected between any of these values.

In one embodiment the binder is selected from gums such as xanthan gum or guar gum, alginates, celluloses and their derivatives such as methylcellulose or microcrystalline cellulose, fats or lipids, starches and their derivatives, dextrins, celluloses and their derivatives, povidones, silicates, mineral oils, vegetable oils, polymethacrylates, polyethylene oxides, gums, waxes, chitosan, polycarbophil, agar, or carbomers or any combination of any two or more thereof.

In one embodiment the binder is a gum such as guar gum or xanthan gum and is present in the formulation at about 0.2 to about 0.6, and more preferably 0.25 to about 0.5% by weight.

In one embodiment, the chewable formulation comprises one or more sweeteners, flavouring agents, or palatability enhancers, or any combination of two or more thereof.

In one embodiment the chewable formulation comprises one or more sweeteners.

In one embodiment the formulation comprises 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80% by weight sweetener, and useful ranges may be selected between any of these values.

In one embodiment the sweetener may be a natural sweetener such as glucose, fructose, sucrose (e.g. icing sugar), lactose, dextrose, glycerol, sorbitol, xylitol, maltitol, lactitol, glycerol, an artificial sweetener such as aspartame, a saccharin, acesulfame, sodium cyclamate, or any combination of any two or more thereof.

In one embodiment, the sweetener is selected from glucose, fructose, sucrose, lactose, dextrose, glycerol, sorbitol, xylitol, maltitol, lactitol, glycerol, aspartame, a saccharin, acesulfame, sodium cyclamate, steviol glycosides (stevia), rebaudiosides (e.g. rebaudioside A), thaumatin, talin, sucralose, licorice and its derivatives, alitame, neotame, neohesperidin, or dihydrochalcone, or any combination of any two or more thereof.

In one embodiment, the chewable formulation comprises one or more flavouring agents, or palatability enhancers, or any combination of any two or more thereof.

In one embodiment the formulation comprises 1, 2, 3, 4, 5, 6, 7, 8, 9, 10, 11, 12, 13, 14, 15, 16, 17, 18, 19, 20, 21, 22, 23, 24, or 25% by weight flavouring agent, or palatability enhancers, or any combination of any two or more thereof, and useful ranges may be selected between any of these values.

In one embodiment the chewable formulation comprises one or more flavouring agents.

In one embodiment the formulation comprises 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24 or 25% by weight flavouring agent, and useful ranges may be selected between any of these values.

In one embodiment, the flavouring agent is an artificial flavouring agent, semi-synthetic flavouring agent, a natural flavouring agent, or nature identical flavouring agent.

In one embodiment, the flavouring agent is fruit, meat (e.g. pork, chicken, beef, fish), vegetable, dairy, honey, or plant derived, or is artificial.

In one embodiment, the flavouring agent is selected from beef flavour, artificial beef type flavour, beef mince, pork liver powder, cheese flavour, roast chicken hickory smoke, stewed beef, chicken fat, savoury flavouring, roast pork, fish flavouring, vanilla, creamy vanilla, butter caramel, peppermint, sweet apple, or any combination of any two or more thereof.

In one embodiment the flavouring agent is selected from artificial beef type flavour, beef mince, pork liver powder, cheese flavour, roast chicken hickory smoke, or any combination of any two or more thereof.

In one embodiment, the chewable formulation comprises one or more palatability enhancers.

In one embodiment, the chewable formulation comprises 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24 or 25% by weight palatability enhancer, and useful ranges may be selected between any of these values.

In one embodiment, the palatability enhancer is a taste masking agent, a flavour potentiator, an aroma modifier, or a taste modifier, or any combination of any two or more thereof.

In one embodiment, the taste modifier is a bitter blocker.

In one embodiment, the bitter blocker is selected from polyethoxylated glycerol fatty acid esters, such as polyethylated castor oil (e.g. cremphor), cyclodextrins (e.g. (β-cyclodextrin), flavanones (e.g. homoeriodictyol sodium salt), alkaline earth metal salts (e.g. zinc sulphate, magnesium sulphate), or celluloses and their derivatives (e.g. carboxymethylcellulose sodium salt), or any combination of any two or more thereof.

In one embodiment, the flavour potentiator is a sweetness enhancer.

In one embodiment, the sweetness enhancer is selected from pyridinium salts (e.g. alapyridaine), substituted benzoic acids (e.g. 2,4-dihydroxybenzoic acid), and positive allosteric modulators.

In one embodiment, the taste masking agent is selected from polyethoxylated glycerol fatty acid esters, such as polyethylated castor oil (e.g. cremophor), fats, or lipids, or any combination of any two or more thereof.

In one embodiment, the aroma modifier is selected from a flavour oil or flavour concentrate.

In one embodiment the chewable formulation comprises 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45% by weight plasticizer, and useful ranges may be selected between any of these values.

In one embodiment the plasticizer may be selected from alcohols, glycols (such as propylene glycol), lanolin, wool fat, liquid paraffin, mineral oil, petrolatum, benzyl phenylformate, chlorobutanol, diethyl phthalate, glycerol, polyethylene glycol, propylene glycol, sorbitol, triacetin, benzyl phenyl formate, PLGA, methacrylates, phthalates, acetyltributyl citrate, acetyltriethyl citrate, castor oil, dibutyl sebacate, tributyl citrate, triethyl citrate, or any combination of any two or more thereof.

In one embodiment the chewable formulation comprises one or more humectants.

In one embodiment the chewable formulation comprises 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, or 90% by weight humectant, and useful ranges may be selected between any of these values.

In one embodiment the humectant is selected from sodium and potassium chloride, benzalkonium chloride, aluminium silicate, sodium propionates, sodium and potassium phosphates, sugars, sulfites, hydrogenated starch hydrosylate, etc. Liquid humectants include, but are not limited to, glycols, polyols, sugar alcohols, vegetable oils and mineral oil, hydrogenated vegetable oils, hydrocarbons, triacetin, liquid paraffin, or any combination of any two or more thereof.

In one embodiment the humectant is in a solid form.

In one embodiment the humectant is selected from propylene glycol and glycerine.

In one embodiment the chewable formulation comprises one or more lubricants.

In one embodiment the chewable formulation comprises 2, 3, 4, 5, 6 ,7 8, 9, 10, 11, 12, 13, 14, 15, 16, 17, 18% by weight lubricant, and useful ranges may be selected between any of these values.

In one embodiment, the lubricant is a fat, lipid or fat and lipid.

In one embodiment the fat, lipid, or fat and lipid is selected from shortening, tallow, stearates, glyceryl distearate, glycerol monostearate, behenoyl polyoxy-8-glyceride, hydrogenated coconut oil, hard fat, or any combination of any two or more thereof. Other fats/lipids known in the art may also be used.

In one embodiment the chewable formulation comprises an antioxidant.

In one embodiment the chewable formulation comprises about 0.0005, 0.001, 0.005, 0.01, 0.05, 0.1, 0.2, 0.3, 0.4, 0.5, 1, 1.5, 2, 2.5, 3, 3.5, 4, 4.5, or 5% by weight antioxidant, and useful ranges may be selected between any of these values.

In one embodiment the antioxidant is selected from propyl gallate, ascorbic acid and its derivatives, sodium formaldehyde sulfoxylate, malic acid, fumaric acid, editic acid, thiols, polyphenols, sodium EDTA, sodium ascorbate, sodium metabisulfite, butylated hydroxytoluene, butylated hydroxyanisole, or natural substances such as flavanoids, tocopherols, carotenes, cysteine, or any combination of any two or more thereof. Other antioxidants known in the art may also be used.

In one embodiment, the chewable formulation comprises a non-aqueous solvent or vehicle.

In one embodiment, the non-aqueous solvent or vehicle is selected from glycerol formal, dimethyl sulfoxide, N-methyl-2-pyrrolidone, ethylene glycol, diethylene glycol monoethyl ether glycofurol, glycerol formal, acetone, alcohol, tetrahydrofurfuryl alcohol, diglyme, dimethyl isosorbide, ethyl lactate.

In one embodiment, the chewable formulation comprises about 1, 2, 3, 4, 5, 6, 7, 8, 9, 10, 11, 12, 13, 14, 15, 16, 17, 18, 19, 20, 21, 22, 23, 24, or 25% by weight non-aqueous solvent or vehicle, and useful ranges may be selected between any of these values.

In one embodiment the chewable formulation comprises a colouring agent.

In one embodiment the chewable formulation comprises a disintegrating agent.

In one embodiment the formulation comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% by weight disintegrating agent, and useful ranges may be selected between any of these values.

In one embodiment the disintegrating agent is selected from povidones, croscarmellose sodium, sodium starch glycollate, celluloses and their derivatives, starches and their derivatives, gelatin, silicon dioxide, or any combination of any two or more thereof.

In one embodiment the chewable formulation comprises preservatives, buffering agents or preservatives and buffering agents.

In one embodiment the chewable formulation comprises 2, 3, 4, 5, 6 , 7, 8, 9, 10, 11, 12, 13, 14, 15, 16, 17, 18% by weight fats, lipids or fats and lipids, and useful ranges may be selected between any of these values.

In one embodiment the preservative is selected from acids, alcohols, phenols, parabens, sorbates, thiols, phenylmercury salts, or any combination of any two or more thereof.

In one embodiment, the chewable formulation comprises a surfactant.

In one embodiment, the formulation comprises about 0.01, 0.02, 0.03, 0.04, 0.05, 0.06, 0.07, 0.08, 0.09, 0.1, 0.15, 0.2, 0.3, 0.4, 0.5, 1, 2, 3, 4, 5, 6, 7, 8, 9, 10, 11, 12, 13, 14, 15, 16, 17, 18, 19, or 20% surfactant by weight, and useful ranges may be selected between any of these values (for example, from about 2 to about 10% surfactant by weight).

In one embodiment, the surfactant is selected from propylene glycol esters (e.g. propylene glycol monocaprylate), PEGs, PEG esters, fatty acid glycerides (e.g. lauroyl glycerides), and anionic surfactants (e.g. sodium lauryl sulfate).

In one embodiment, the chewable formulation comprises a solubility enhancer, bioavailability enhancer, or a solubility enhancer and bioavailability enhancer. The solubility enhancer and/or bioavailability enhancer enhances the solubility and/or bioavailability of the nutritional or pharmaceutically active agent.

In one embodiment, the chewable formulation comprises about 0.01, 0.1, 0.5, 1, 2, 3, 4, 5, 6, 7, 8, 9, 10, 11, 12, 13, 14, 15% by weight solubility enhancer, bioavailability enhancer, or solubility enhancer and bioavailability enhancer, and useful ranges may be selected between any of these values.

In one embodiment, the solubility enhancer is selected from surfactants, complexing agents, buffers, or ionic salts, or any combination of any two or more thereof.

In one embodiment, the solubility enhancer is selected from sodium lauryl sulphate, polysorbates, spans, polyethylene glycols, bile salts, lecithin, phospholipids, poloxamers, polyoxyl 35 castor oil, medium chain mono- and diglycerides, propylene glycol monolaurate, polyvinyl caprolactam-polyvinyl acetate-polyethylene glycol graft copolymer, tocopheyl polyethylene glycol succinate, polyoxyl-15-hydroxystearate, lauroyl polyoxyl-32 glycerides, nonionic triblock copolymers, polyoxyethylene (8) caprylic/capric glycerides, PEG-40 hydrogenated castor oil, diethylene glycol monoethyl ether and caprylocaproyl macrogol glycerides, or any combination of any two or more thereof. Any other suitable solubility enhancers known in the art may be used.

In one embodiment, the bioavialbility enhancer is penetration enhancer.

In one embodiment, the bioavailability enhancer is a naturally or herbally derived bioavailability enhancer.

In one embodiment, the bioavailability enhancer is selected from quercetin, genistein, lysergol, naringin, sinomenine, piperine, glycyrrhizin, nitrile glycoside, cuminum cyminum, niaziridin, piperine, or allicine.

In one embodiment, the chewable formulation comprises one or more complexing agents.

In one embodiment, the nutritional or pharmaceutically active agent is complexed or conjugated with one or more complexing agents.

In one embodiment, the complexing agent is selected from EDTA, choleic acid, cyclodextrins (e.g. (β-cyclodextrin), cyclic glucose oligomers, or polymers such as polethylene glycols, methyl cellulose, carboxy methyl cellulose and polyvinylpyrollidine, or any combination of any two or more thereof.

In one embodiment, the chewable formulation comprises about 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 60, 70 or 80% complexing agent by weight, and useful ranges may be selected between any of these values (for example, from about 0.1% to about 30% complexing agent by weight). The amount used depends on the concentration of API and its affinity for the complexing agent.

In one embodiment, the molar ratio of API : complexing agent is about 4:1, 2:1, 1:1, 1:2, 1:3, 1:4, 1:5, 1:6, 1:7, 1:8, 1:9, or 1:10, and useful ranges may be selected between any of these values (for example, from about 1:1 to about 1:10.

In one embodiment, the chewable formulation comprises one or more coating agents.

In one embodiment, the nutritional or pharmaceutically active agent, optionally in granular form, are coated with the one or more coating agents.

In one embodiment, the chewable formulation comprises about 1% to about 20% coating agent by weight of the nutritional or pharmaceutically active agent.

In one embodiment, the coating agent is selected from polyethylene glycols, a wax, or a fatty acid, or a combination of any two or more thereof.

In one embodiment, the formulation comprises about 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39% by weight liquid ingredients, and useful ranges may be selected between any of these values.

In one embodiment the chewable formulation is a single extrudate or co-extrudate.

In one embodiment, the nutritional or pharmaceutically active agent is, prior to the addition of the plasticiser, combined with one or more ingredients selected from:
  a filler, diluent or filler and diluent,
  a binder,
  a sweetener,
  a flavouring agent,
  a humectant,
  a fat, lipid or fat and lipid,
  an antioxidant,
  a colouring agent,
  a disintegrating agent,
  a preservative, buffering agent, or preservative and buffering agent,
  a lubricant,
  a complexing agent,
  a coating agent,
  a surfactant,
  a solubility enhancer, bioavailability enhancer, or a solubility enhancer and a bioavailability enhancer,
  a palatability enhancer, or
  a non-aqueous solvent or vehicle, or
  any combination of any two or more thereof.

In one embodiment, the one or more ingredients are in a dry state. In alternate embodiment, the one or more ingredients are not in liquid form.

In one embodiment, the nutritional or pharmaceutically active agent is combined with the one or more ingredient, prior to the addition of the fat, lipid or fat and lipid.

In one embodiment, the fat, lipid or fat and lipid acts as a plasticiser and the first composition is extruded.

In one embodiment the active ingredient is, prior to the addition of the fat, lipid or fat and lipid, combined with
  a filler,
  a diluent,
  a sweetener,
  a flavouring agent,
  a binder, or
  a disintegrating agent, or
  any combination of two or more of the above.

In one embodiment the filler, diluent, sweetener, flavouring agent, binder and disintegrating agent are all in a dry state.

In one embodiment the fat, lipid, or fat and lipid are pulverised before being added.

In one embodiment a plasticiser is added to the second composition.

In one embodiment, the plasticiser is in the form of a liquid.

In one embodiment, the extrusion is carried out at a temperature and/or pressure sufficient to at least partially melt the fat, lipid, or fat and lipid.

In one embodiment, the conditions are sufficient to melt at least 10, 15, 20, 25, 30, 35, 40, 45, 50, 55, 60, 65, 70, 75, 80, 85, 90, 95% of the fat, lipid, or fat and lipid.

In one embodiment, the conditions are effective to completely melt the fat, lipid, or fat and lipid.

In one embodiment, the method of manufacture is carried out without applying heat.

In one embodiment, the extrusion is carried out without applying heat.

In one embodiment the extrusion is performed under pressure sufficient to bind the ingredients together.

In one embodiment, the extruded composition is allowed to cool to room temperature after extrusion, thereby providing the chewable formulation.

In one embodiment, the chewable formulation is suitable for packaging immediately after extrusion.

In one embodiment, the method of manufacture further comprises packaging the chewable formulation.

In one embodiment, the chewable formulation is packaged immediately after extrusion.

In one embodiment, the chewable formulation is packaged within 1, 2, 3, 4, 5, 6, 7, 8, 9, 10, 15, 30, 60, 90, or 120 minutes after extrusion, and useful ranges may be selected between any of these values.

In another embodiment, the chewable formulation is packaged within 1, 2, 3, 4, 5, 6, 7, 8, 9, 10, 11, 12, 18, 24, 48, or 72 hours extrusion, and useful ranges may be selected between any of these values.

In one embodiment, the extruded composition is not allowed to cool or cooled prior to packaging.

In one embodiment, the extruded composition is not cured prior to packaging.

In one embodiment, the packaging is hermetic.

In one embodiment, the chewable formulation is formed on extrusion.

In one embodiment, the chewable formulation is packaged without cooling or curing.

In one embodiment, the method of manufacturing the shelf stable chewable formulation is continuous.

In one embodiment, the method of manufacture comprises co-extruding at least one additional composition.

In one embodiment, the at least one additional composition comprises a processed or unprocessed food material, or a nutritional or pharmaceutically active agent, or any combination of any two or more thereof.

In one embodiment, the food material is of plant or animal origin. In one embodiment, the food material is confectionary.

In one embodiment, the at least one additional composition comprises a palatable chewable base and optionally a nutritional or pharmaceutically active agent.

In one embodiment, the first or second composition comprises an unpalatable nutritional or pharmaceutically active agent and the at least one additional composition comprises a palatable chewable base and optionally a nutritional or pharmaceutically active agent.

In one embodiment, the at least one additional composition comprises
- a filler, diluent or filler and diluent,
- a binder,
- a sweetener,
- a flavouring agent,
- a plasticizer,
- a humectant,
- a fat, lipid or fat and lipid,
- an antioxidant,
- a colouring agent,
- a disintegrating agent,
- a preservative, buffering agent, or preservative and buffering agent,
- a lubricant,
- a complexing agent,
- a coating agent,
- a surfactant,
- a solubility enhancer, bioavailability enhancer, or a solubility enhancer and a bioavailability enhancer,
- a palatability enhancer, or
- a non-aqueous solvent or vehicle, or
- any combination of any two or more thereof.

In one embodiment at least 90, 91, 92, 93, 94, 95, 96, 97, 98, 99% by weight of any water present in the chewable formulation is present in a bound state, and useful ranges may be selected between any of these values.

In one embodiment the chewable formulations may have acceptable physical and chemical stability, providing at least 12, 13, 14, 15, 16, 17, 18, 19, 20, 21, 22, 23, 24, 25, 26, 27, 28, 29, 30, 31, 32, 33, 34, 35, or 36 months shelf life, and useful ranges may be selected between any of these values.

In one embodiment, the chewable formulation is chewable for at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 months.

In one embodiment, the chewable formulation has a chewiness of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 11, 12, 13, 14, 15, 16, 17, 18, 19, or 20 N, and useful ranges may be selected between any of these values.

In one embodiment, the chewable formulation has a hardness of about 1000, 950, 900, 850, 800, 750, 725, 700, 675, 650, 625, 600, 575, 550, 525, 500, 475, 450, 425, 400, 375, 350, 325, 300, 275, 250, 225, 200, 175, 150, 125, 100, 75, 50, 25, 20, 15, or 10 N, and useful ranges may be selected between any of these values.

In one embodiment, the chewable formulation has a compression energy of energy of about 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2100, 2200, 2300, 2400, 2500, 2600, 2700, 2800, 2900, or 3000 N.mm, and useful ranges may be selected between any of these values.

In one embodiment, the chewable formulation has an adhesion of about 0, −0.5, −1, −1.5, −2, −2.5, −3, −3.5, −4, −4.5, −5, −5.5, −6, −6.5, −7, −7.5, −8, −8.5, −9, −9.5, −10, −11, −12, −13, −14, −15, −16, −17, −18, −19, or −20 N.mm, and useful ranges may be selected between any of these values.

In one embodiment, the chewable formulation has a cohesiveness of about 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.25, 0.3, 0.35, 0.4, 0.45, or 0.5, and useful ranges may be selected between any of these values.

In one embodiment, the chewable formulation has a springiness of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40%, and useful ranges may be selected between any of these values.

In one embodiment, the chewable formulation has a modulus of about 1, 2, 3, 4, 5, 10, 15, 20, 25, 30, 35, 40, 45, 50, 55, 60, 65, 70, 75, 80, 85, 90, 95, 100, 110, 120, 130, 140, 150, 160, 170, 180, 190, or 200 N/mm, and useful ranges may be selected between any of these values.

In one embodiment the chewable formulation delivers at least 80% of the active ingredient loading within 10, 15, 20, 25, 30, 35, 40, 45, 50, 55, 60, 65, 70, 75, 80, 85, 90 or 95 minutes, and useful ranges may be selected between any of these values.

In one embodiment, the chewable formulation provides sustained delivery of the nutritional or pharmaceutically active ingredient over an extended period of time. In one embodiment, the active ingredient is delivered over 2, 4, 6, 8, 10, 12, 24, 48, 60, 72, 96, 120, 144, or 168 hours, and useful ranges may be selected between any of these values.

In one embodiment, the chewable formulation provides delayed delivery of the nutritional or pharmaceutically active ingredient. In one embodiment, delivery is delayed by about 1, 2, 3, 4, 5, 6, 8, 10, 12, 24, 48, or 72 hours, and useful ranges may be selected between any of these values.

In one embodiment the chewable formulation substantially retains its malleability throughout the shelf-stable period.

In one embodiment, the chewable formulation substantially retains a characteristic selected from chewiness, hardness, compression energy, adhesion, cohesiveness, springiness, modulus, and any combination of any two or more thereof (as measured by the method described in Example 7).

In one embodiment the chewable formulation does not dry out nor become brittle over the shelf-stable period.

In one embodiment, the release characteristics of the nutritional or pharmaceutically active agent are substantially maintained throughout the shelf-stable period.

In one embodiment, the chewable formulation delivers the nutritional or pharmaceutically active agent at substantially the same dose and rate throughout the shelf stable period.

In another aspect the invention the invention is the use of any one or more of the compositions described above.

In another aspect the invention the invention may be the use of any one or more of the compositions described above.

In another aspect, the invention relates to the use of a chewable formulation of the invention for treating an animal in need thereof.

In another aspect, the invention relates to a method of treating an animal in need thereof with a chewable formulation of the invention.

In another aspect, the invention relates to use of a nutritional or pharmaceutically active agent, and a plasticiser in the manufacture of a chewable formulation of the invention for treating an animal in need thereof.

In another aspect, the invention relates to a shelf stable chewable formulation manufactured by a method of the invention.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7).

As used herein, the term "substantially" means at least 90, 95 or 99%.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting In this specification, where reference has been made to external sources of information, including patent specifications and other documents, this is generally for the purpose of providing a context for discussing the features of the present invention. Unless stated otherwise, reference to such sources of information is not to be construed, in any jurisdiction, as an admission that such sources of information are prior art or form part of the common general knowledge in the art.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
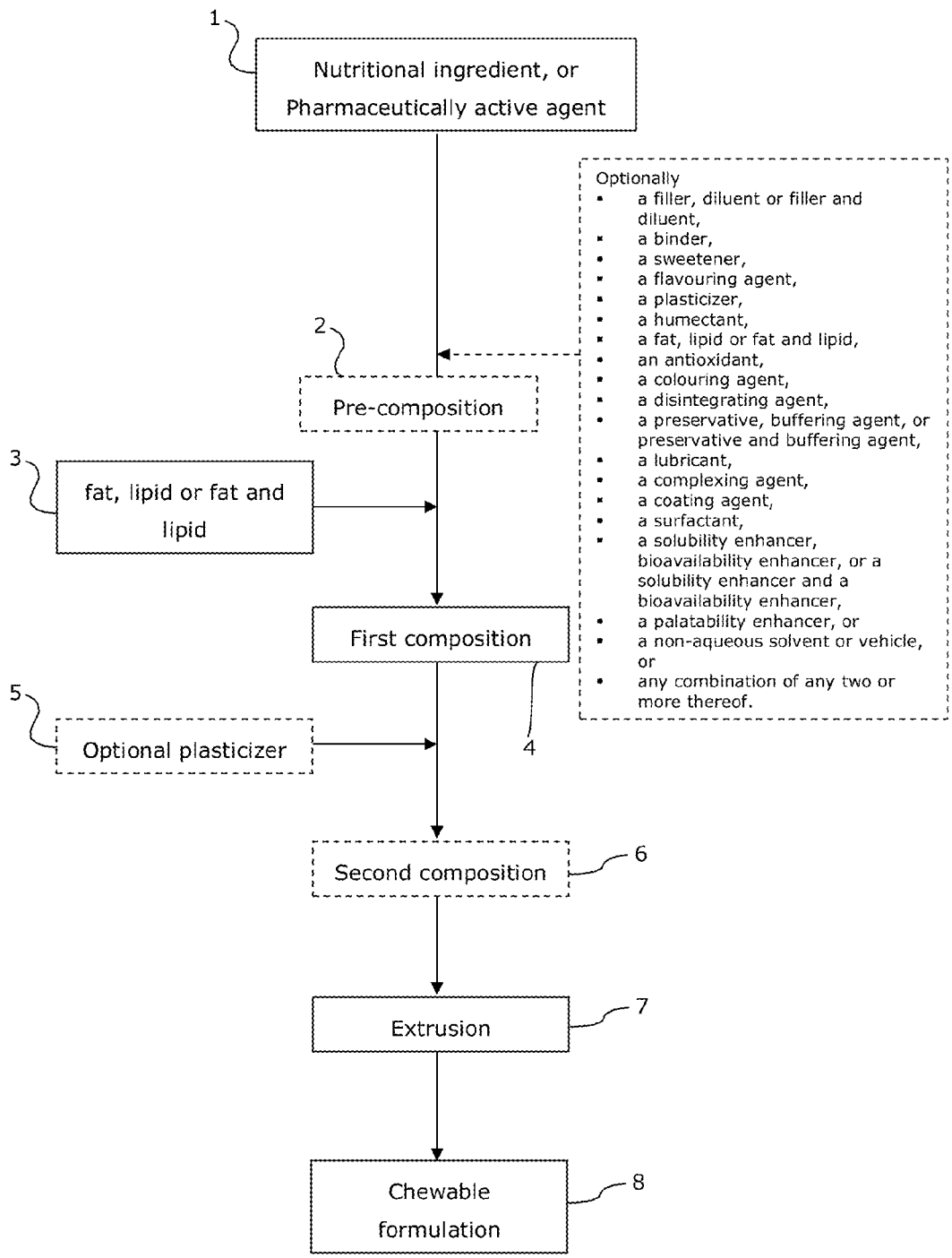
FIG. 1 depicts a representative schematic of the invention.

The present invention relates to the preparation of a chewable treat manufactured by extrusion and which does not contain water in a free state. Without wishing to be limited by theory, the absence of water in a free state
  reduces the risk of microbial contamination,
  improves chemical stability of the nutritional and pharmaceutical ingredients,
  prevents the dosage unit from becoming hard and brittle over time, or
  any combination of two or more of the above.

The present invention provides a simple and effective method for preparing of semi-soft, palatable and stable chewable treat without addition of water.

It should be appreciated that the present invention provides a platform for administering therapeutic ingredients and/or nutritional ingredients to veterinary animals.

The present invention also relates to a composition for the manufacture of stable and palatable, fast disintegrating, semi-soft medicated chewable tablets (treats) by extrusion without the addition of extraneous water. The soft chewable tablets do not harden on storage and are resistant to microbial contamination.

In one embodiment the semi-soft chewable treats contain a blend of any one or more of binders, flavours, palatability enhancers, humectants, disintegrating agents, non-aqueous solvents, and diluents that are plasticized with liquid plasticizers, such as glycols and polyols to make them ductile and extrudable.

The present invention provides an extrudable chew that
  uses fats or lipids as plasticizers and binding agents,
  is manufactured in the absence of added water,
  uses plasticizers to replace water in extrudable matrices,
  contains humectants to maintain the extrudable chew in a pliant and soft state during its shelf life, or
  any combination of two or more of the above.

The components of the invention are described as follows.

The chewable composition of the present invention is a platform technology to allow delivery of an active ingredient in a chewable form to an animal. A wide range of active ingredients can be delivered orally by the chewable platform formulation of the present invention. The active ingredient may be any orally active drug or other biologically active compound known in art for human and/or veterinary pharmaceuticals and nutraceuticals.

For example, the active ingredient may be a nutritional ingredient. A nutritional supplement includes any ingredient whose purpose is to assist or maintain the health of the target animal. For example, the nutritional supplement may provide a nutritional benefit to the target animal.

In some embodiments the chewable formulation delivers a therapeutic substance to the target animal, such as a pharmaceutically active agent.

The pharmaceutically active agent can be chosen from various treatment groups, such as anesthetics, corticosteroids, NSAIDS, antibiotics, antiemetics, anti-thyroidal agents or parasiticidal agents; or they could be selected for their nutritional value such as for example, vitamins or minerals or a combination thereof.

As a non-limiting example, the nutritional active could be a vitamin. Non-limiting examples of vitamins include vitamin A, vitamin E, vitamin $B_{12}$, vitamin $B_3$, d-pantothenic acid (vitamin $B_5$), folic acid, vitamin $B_6$, vitamin $B_1$, vitamin $D_3$, vitamin C, vitamin $B_2$. As another example, the nutritional active could be a pro-vitamin, for example beta-carotene or panthenol.

As another non-limiting example, the nutritional active could be a mineral. Non-limiting examples of minerals include potassium, sodium, manganese, zinc, iron, calcium, copper, cobalt, iodine, chlorine and selenium. The mineral may be in the form of a suitable salt.

As another example, the nutritional active could be a glycosaminoglycan or a nutritionally active monomer thereof. As a non-limiting example, the glycosaminoglycan could be chondroitin. As a non-limiting example, the glycosaminoglycan monomer could be glucosamine.

As another example, the nutritional active could be an amino acid. Suitable amino acids include but are not limited to the 20 naturally occurring L-amino acids, for example arginine, isoleucine, leucine, lysine, etc.

As another example, the nutritional active could be a co-enzyme, for example co-enzyme Q.

Vitamin, pro-vitamin, mineral, glycosaminoglycan or a nutritionally active monomer thereof, an amino acid, or a co-enzyme.

As a non-limiting example, the pharmaceutically active agent could be a NSAID such as meloxicam or carprofen. As another non-limiting example the pharmaceutically active agent could be selected from an anthelmintic such as a macrocyclic lactone, benzimidazole, imidazothiazole or salicylanilide. As an example of a macrocyclic lactone the pharmaceutically active agent could be selected from abamectin, moxidectin, avermectin, ivermectin, selamectin or cydectin. As an example of a benzimidazole, the pharmaceutically active agent could be selected from mebendazole, fenbendazole, oxfendazole, albendazole, thiabendazole or carbendazol. As an example of an imidazothiazole, the pharmaceutically active agent could be selected from levamisole, pyrantel pamoate, butamisole, or tetramisole. As an example of a salicylanilide the pharmaceutically active agent could be selected from clioxanide, closantel or niclosamide.

In one embodiment, the pharmaceutically active agent is an anesthetic. Anesthetics include, but are not limited to, local anesthetics, such as procaine, bupivicaine, lidocaine and proparacaine, phenothiazine and buterophenone sedatives, for example acepromazine, chlorpromazine, droperidol and azaperone, benzodiazapines, such as diazepam, midazolam and zolazepam, alpha-2 adrenergic agonists, such as thiazines, for example xylazine, and medetomidine, opiates, for example buprenorphine, pentazocine, nalbuphine, butorphanol, fentanyl, morphine, meperidine, and oxymorphone, barbiturates, such as phenobarbital, thiopental, and thiamylal, and dissociative anesthetics, such as ketamine and tiletamine.

In one embodiment, the pharmaceutically active agent is an analgesic. Analgesics include, but are not limited to, opioid analgesics and non-opioid analgesics, for example non-steroidal anti-inflammatories, such as those described herein. Non-limiting examples of opioid analgesics include buprenorphine, butorphanol, dextromoramide, dezocine, dextropropoxyphene, diamorphine, fentanyl, alfentanil, sufentanil, hydrocodone, hydromorphone, ketobemidone, levomethadyl acetate, mepiridine, methadone, morphine, nalbuphine, opium, oxycodone, papaveretum, pentazocine, pethidine, phenoperidine, piritramide, dextropropoxyphene, remifentanil, tilidine, tramadol, codeine, dihydrocodeine, meptazinol, dezocine, eptazocine and flupirtine.

In one embodiment, the pharmaceutically active agent is a corticosteroid. Non-limiting examples of corticosteroids include endogenous and synthetic adrenocorticoid steroids. These include, but are not limited to, hydrocortisone, betamethasone, cortisone, dexamethasone, prednisolone, prednisone, methylprednisilone, triamcinolone, flumethasone, and their pharmaceutically acceptable derivitives.

In one embodiment, the pharmaceutically active agent is an NSAID. NSAIDs include, but are not limited to, carboxylic acid and enolic acid derivatives. Enolic acid NSAIDs include, but are not limited to, pyrazolones (e.g. phenylbutazone, oxyphenbutazone, and ramifenazone) and oxicams (e.g. meloxicam, piroxicam, and tenoxicam). Carboxylic acid NSAIDs include, but are not limited to, salicylates (e.g. aspirin), propionic acids (e.g. ibuprofen, naproxen, carprofen, ketoprofen, and vedaprofen), anthranilic acids (e.g. tolfenamic and meclofenamic acids), phenylacetic acids (e.g. acetaminophen), aminonicotinic acids (e.g. flunixin), and indolines (e.g. indomethacin).

Further non-limiting examples of NSAIDs include acemetacin, acetylsalicylic acid (aspirin), alminoprofen, benoxaprofen, bucloxic acid, carprofen, celecoxib, clidanac, deracoxib, diclofenac, diflunisal, dipyrone, etodolac, fenoprofen, fentiazac, firocoxib, flobufen, flufenamic acid, flufenisal, flunixin, fluprofen, flurbiprofen, ibuprofen, indomethacin, indoprofen, isoxicam, ketoprofen, ketorolac, meclofenamic acid, mefenamic acid, meloxicam, miroprofen, nabumetone, naproxen, niflumic acid, oxaprozin, oxepinac, phenylbutazone, piroxicam, pirprofen, pramoprofen, sudoxicam, sulindac, suprofen, tepoxalin, tiaprofenic acid, tiopinac, tolfenamic acid, tolmetin, trioxaprofen, zidometacin, or zomepirac, pharmaceutically acceptable salts thereof and mixtures thereof.

In one embodiment, the pharmaceutically active agent is an antibiotic. Non-limiting examples of antibiotics include beta-lactams such as penicillins, aminopenicillins (e.g., amoxicillin, ampicillin, hetacillin), penicillinase resistant antibiotics (e.g., cloxacillin, dicloxacillin, methicillin, nafcillin, oxacillin), extended spectrum antibiotics (e.g., axlocillin, carbenicillin, mezlocillin, piperacillin, ticarcillin); cephalosporins (e.g., cefadroxil, cefazolin, cephalixin, cephalothin, cephapirin, cephradine, cefaclor, cefacmandole, cefmetazole, cefonicid, ceforanide, cefotetan, cefoxitin, cefprozil, cefuroxime, loracarbef, cefixime, cefoperazone, cefotaxime, cefpodoxime, ceftazidime, ceftiofur, ceftizoxime, ceftriaxone, moxalactam); monobactams such as aztreonam; carbapenems such as imipenem and eropenem; quinolones (e.g., ciprofloxacin, enrofloxacin, difloxacin, orbifloxacin, marbofloxacin); chloramphenicols (e.g., chloramphenicol, thiamphenicol, florfenicol); tetracyclines (e.g., chlortetracycline, tetracycline, oxytetracycline, doxycycline, minocycline); macrolides (e.g., erythromycin, tylosin, tlimicosin, clarithromycin, azithromycin); lincosamides (e.g., lincomycin, clindamycin); aminoglycosides (e.g., gentamicin, amikacin, kanamycin, apramycin, tobramycin, neomycin, dihydrostreptomycin, paromomycin); sulfonamides (e.g., sulfadmethoxine, sulfamethazine, sulfaquinoxaline, sulfamerazine, sulfathiazole, sulfasalazine, sulfadiazine, sulfabromomethazine, suflaethoxypyridazine); glycopeptides (e.g., vancomycin, teicoplanin, ramoplanin, and decaplanin); and other antibiotics (e.g., rifampin, nitrofuran, virginiamycin, polymyxins, tobramycin).

In one embodiment, the pharmaceutically active agent is an antiemetic. Non-limiting examples of antiemetics include phenothiazines (e.g. prochloperazine, promethazine, thiethylperazine, perphenazine, chlorpromazine, metopimazine, acepromazine), 5HT-3 receptor antagonists such as ondansetron, granisetron, tropisetron, dolasetron, hydrodolasetron, azasetron, ramosetron, lerisetron, indisetron and palonosetron, and others such as dimenhydrinate, diphenhydramine (which can also act as an antihistamine), cyclizine, meclizine, promethazine, hyroxyzine, metoclopramide, domperidone, hyoscine, hyoscine hydrobromide, hyoscine hydrochloride, scopolamine, clebopride, alizapride, itopride, bromopride, droperidol, haloperidol, benzquinamide, cerium oxalate, diphenidol, dronabinol, nabilone, ginger, levosulpiride, butorphanol and aprepitant.

In one embodiment, the pharmaceutically active agent is an anti-thyroidal agent. Anti-thyroidal agents include, but are not limited to, carbimazole, methimazole, and propylthiouracil.

In one embodiment, the pharmaceutically active agent is a parasiticidal agent. Non-limiting examples of parasiticidal agents include macrocyclic lactones such as abamectin, ivermectin, eprinomectin, doramectin, moxidectin, selamectin, milbemycin oxime.

The parasiticidal agent may be an endoparasiticidal agent, ectoparaciticidal agent, orendectoparaciticidal agent. Ectoparasiticides include, for example, organochlorines, organophosphates, carbamates, amidines, pyrethrins and synthetic pyrethroids, benzoylureas, juvenile hormone analogues, macrocyclic lactones, neonicotinoids, phenylpyrazoles, and spinosyns, such as spinosad. Endectoparaciticides include, for example, macrocyclic lactones, such as ivermectin. Endoparasiticides include, for example, anthelmintics, such as those described herein. Examples of parasiticidal agents include avermectin, milbemycin, phenylpyrazole, nodulisporic acid, clorsulon, closantel, quinacrine, chloroquine, vidarabine, nitenpyram, ivermectin, milbemycine oxime, lufenuron, salimectin, moxidectin, dorimectin, and paraherquamide.

In one embodiment, the pharmaceutically active agent is an anthelmintic. Anthelmintics include, but are not limited to, benzimidazoles, imidazothiazoles, tetrahydropyrimidines, macrocyclic lactones, salicylanilides, substituted phenols, aromatic amides, isoquinolines, amino acetonitriles, spiroindoles.

Anthelmintic benzimidazoles include, but are not limited to, mebendazole, flubendazole, fenbendazole, oxfendazole, oxibendazole, albendazole, albendazole sulfoxide, thiabendazole, thiophanate, febantel, netobimin, and triclabendazole. Further examples include mebendazole, and ricobendazole.

Imidazothiazoles and tetrahydropyrimidines are both nicotinic agonists. Anthelmintic imidathiazoles include, but are not limited to, levamisole, tetramisole, and butamisole. Tetrahydropyrimidine anthelmintics include, for example, morantel, oxantel, and pyrantel.

Macrocyclic lactones include, but are not limited to, abamectins, for example abamectin, doramectin, eprinomectin, ivermectin, and selamectin, and milbemycins, for example milbemycin oxime and moxidectin.

Salicylanilides include, but are not limited to, brotianide, clioxanide, closantel, niclosamide, oxyclozanide, and rafoxanide. Substituted phenols include, but are not limited to, bithionol, disophenol, hexachlorophene, niclofolan, menichlopholan, and nitroxynil. Aromatic amides include diamfenetide.

Isoquinoline anthelmintics include, but are not limited to, praziquantel and epsiprantel. Amino-acetonitrile derivatives include, but are not limited to, monepantel.

Further examples of anthelmintics include, but are not limited to, piperazine and derivatives thereof such as piperazine and diethylcarbamazine, benzenesulfonamides such as clorsulon, amidines such as bunamidine, isothiocyantes such as nitroscanate, and organophosphates such as dichlorvos, and spiroindoles such as derquantel.

In one embodiment, the pharmaceutically active agent is an appetite stimulant. There are several widely used drugs which can cause a boost in appetite. Examples, include, but are not limited to, tricyclic antidepressants (TCAs), tetracyclic antidepressants, natural or synthetic cannabinoids, first-generation antihistamines, antipsychotics, steroid hormones, and ghrelin receptor agonists such as capromorelin. Non-limiting examples of appetite stimulants used in pets include cyproheptadine, diazepam, mirtazapine, megesterol acetate, stanozolol. Examples of appetite stimulants used in humans include medroxyprogesterone acetate, dronabinole, and dexamethasone.

In one embodiment, the pharmaceutically active agent is an anti-histamine. Non-limiting examples of antihistamines include cetirizine, clemastine, clemastine fumarate, dexmedetomidine, doxylamine, loratidine, desloratidine and promethazine, and diphenhydramine, or pharmaceutically acceptable salts, solvates or esters thereof.

In one embodiment, the pharmaceutically active agent is a histamine blocker. Histamine blockers include but are not limited to cimetidine, famotidine, nizatidine, and ranitidine.

In one embodiment, the pharmaceutically active agent is an anti-fungal agent. Anti-fungals include but are not limited to polyenes, azoles, allylamines, morpholines, antimetabolites, and combinations thereof. Non-limiting examples include nystatin, fluconazole, itraconazole, clotrimazole, ketoconazole, terbinafine, 5-fluorocytosine, and amphotericin B.

In one embodiment, the pharmaceutically active agent is an antiprotozoal agent. Non-limiting examples of antiprotozoal agents include eflornithine, furazolidone, melarsoprol, metronidazole, ornidazole, paromomycin sulphate, pentamidine, pyrimethamine and tinidazole. Antiprotozoal agents include coccidostats. Examples of coccidostats include, but are not limited to, amprolium, arprinocid, artemether, clopidol, decoquinate, diclazuril, dinitolmide, ethopabate, halofuginone, lasalocid, monensin, narasin, nicarbazin, oryzalin, robenidine, roxarsone, salinomycin, spiramycin, sulfadiazine, and toltrazuril.

In one embodiment, the pharmaceutically active agent is an anti-depressant. Anti-depressants include but are not limited to serotonin reuptake inhibitors and tricyclic antidepressants, for example amitriptyline and clomipramine.

In one embodiment, the pharmaceutically active agent is a steroid. Steroids include, for example, corticosteroids such as those described herein. Further non-limiting examples include paramethasone, betamethasone, dexamethasone, fludrocortisone, stanozolol, boldenone undecylenate, and trenbolone acetate.

Steroids include natural and synthetic steroid hormones, steroid hormone precursors, steroid hormone metabolites, and derivatives thereof structurally derived from cholesterol. Steroid hormones include, but are not limited to, androgens, estrogens, progestogens, mineralcorticoids, and glucocorticoids. Non-limiting examples of androgens include testosterone, dehydroepiandrosterone, dehydroepiandrosterone sulphate, dihydrotestosterone, androstenedione, androstenediol, androstanedione, and androstanediol. Non-limiting examples of estrogens include estrone, estradiol, estriol, estetrol, equilin, and equilenin. Non-limiting examples of progestogens include progesterone, 17-hydroxy-progesterone, pregnenolone, dihydroprogesterone, allopregnanolone, 17-hydroxy-pregnenolone, 17-hydroxy-dihydroprogesterone, and 17-hydroxy-allopregnanolone. Non-limiting examples of mineralcorticoids include aldosterone, 11-deoxycorticosterone, fludrocortisones, 11-deoxy-cortisol, and pregnenedione. Non-limiting examples of glucocorticoids include cortisol (hydrocortisone), corticosterone, 18-hydroxy-corticosterone, cortisone.

In one embodiment the nutritional ingredient or pharmaceutically active agent is added to the composition by dry blending.

In one embodiment the nutritional ingredient or pharmaceutically active agent may be dissolved in an appropriate solvent before addition to the composition.

In one embodiment, the nutritional ingredient or pharmaceutically active agent may be dissolved, emulsified, or suspended in a non-aqueous solvent before addition.

In one embodiment the nutritional ingredient or pharmaceutically active agent is granulated before addition to the composition to improve distribution and/or improve chemical stability. In one embodiment, granulation masks offensive tastes and/or offensive odours.

In one embodiment the nutritional ingredient or pharmaceutically active agent, optionally in granular form, are coated, or further coated, with a suitable coating. In one embodiment the coating is a coating polymer that coats and protects the nutritional ingredient or pharmaceutically active agent. In another embodiment, the coating masks offensive taste and/or offensive odour. In one embodiment the coating polymer is selected from polyethylene glycols, a wax, or a fatty acid.

In one embodiment the coating polymer is a wax is sourced from animal, vegetable, mineral, petroleum or synthetic waxes. More preferably, the wax is an animal wax such as beeswax.

In an alternate embodiment the coating polymer is a saturated $C_{18}$-$C_{22}$ fatty acid. More preferably the fatty acid is stearic acid.

The nutritional or pharmaceutically active agent may be soluble, partially soluble, or insoluble in water.

In one embodiment the nutritional ingredient or pharmaceutically active agent (optionally in granular form) are conjugated with other substances, such as cyclodextrins, surfactants, solubility or bioavailability enhancers, etc., to inhibit interactions with other excipients or with the environment, promote its chemical stability, improve solubility, enhance bioavailability, or improve platability. Similarly, the pharmaceutically active agent may be incorporated in to novel drug delivery systems, such as microcapsules, liposomes, niosomes, nanoparticles, microemulsions, or nanoemulsions to protect the drug or permit organ targeting.

In one embodiment, the chewable formulation comprises two or more nutritional or pharmaceutically active agents.

In one embodiment the chewable formulation comprises a nutritional ingredient and pharmaceutically active agent.

In some embodiments the composition includes the presence of one or more excipients.

In some embodiments a single excipient has more than one function in the formulation of the present invention. For example, propylene glycol and glycerol may be present and have a simultaneous role as a plasticizer, humectant, antimicrobial agents, or any combination of any two or more thereof, in this formulation. Sugar may have a role as a sweetener, humectant, diluent, or any combination of any two or more thereof. Lipids or fats may have a role as a lubricant, plasticizer, binders, or any combination of any two or more thereof. Any suitable excipient may be used.

Table 1 below describes preferred ingredients as well as examples and/or alternatives that could be used in the present invention.

TABLE 1

List of ingredients used the chewable formulation of the present invention.

| Ingredient | Function | Examples and/or alternatives (can be used alone or in combination) |
|---|---|---|
| Ascorbyl Palmitate | Antioxidant | Propyl gallate, ascorbic acid, sodium ascorbate, sodium metabisulfite, thiols, polyphenols, BHT, BHA |
| α-Tocopherol | Antioxidant | Fumaric acid, malic acid, Editic acid (EDTA), flavonoids |
| Cellulose powder | Filler/diluent | Cellulose derivatives, starch derivatives, calcium phosphates, cellulose acetate, dextrates, starches and derivatives, silicates, protein powders, wheat gluten, soy powder, sugars and sugar alcohols |
| Microcrystalline cellulose + $Ca_2PO_4$ | Dry Binder | Povidones, starches, celluloses, silicates, alginates, gums, waxes |
| Methylcellulose | Dry Binder | Povidones, starches, celluloses, silicates, alginates, gums, waxes |
| Beef Type Flavour | Flavouring agent | Any artificial, natural or semisynthetic flavour/palatability enhancers |
| Icing Sugar (sucrose) | Sweetening agent | Any natural (sugars, sugar alcohols) and/or artificial (aspartame, saccharins, acesulfame), sweeteners |
| Glyceryl distearate | Lubricant | Artificial natural or semisynthetic fats (stearates, glycerides, paraffin, hydrogenated vegetable oils, animal fats) |
| Sodium chloride | Humectant | Potassium chloride, hyamine, aluminium silicate, sodium propionates, sodium and potassium phosphates, sufites |

TABLE 1-continued

List of ingredients used the chewable formulation of the present invention.

| Ingredient | Function | Examples and/or alternatives (can be used alone or in combination) |
|---|---|---|
| Glycerine | Plasticizer | Alcohols, lanolin, petrolatum, glycols, polyols, vegetable oils, hydrocarbons, hydrogenated vegetable oils |
| Propylene Glycol | Plasticizer | Methacrylates, glycols, polyols, vegetable oils, hydrocarbons, hydrogenated vegetable oils |
| Pregelatinized starch | Disintegrating agent | Povidones, croscarmellose sodium, sodium starch glycollate, cellulose, gelatine, silicon dioxide, starch |
| Non-aqueous solvents or vehicles | Solvent or vehicle | Dimethyl sulfoxide, N-methyl-2-pyrrolidone, ethylene glycol, diethylene glycol monoethyl ether glycofurol, glycerol formal, acetone, alcohol, tetrahydrofurfuryl alcohol, diglyme, dimethyl isosorbide, ethyl lactate |
| Buffering agents | Buffer | Citric acid, tartaric acid and other acidifying agents, sodium carbonate, sodium bicarbonate, sodium citrate, other carbonates, other alkalizing agents |
| Colouring agent | Colour | Any natural or artificial colourant |
| Preservatives | Preserve | Acids, alcohols, phenols, parabens, sorbates, thiols, phenylmercury salts |

In one embodiment the chewable formulation comprises one or more fillers. A filler may be used to increase the total mass of the chewable formulation to a manageable size. The filler may also modify texture, have taste masking abilities or be a sweetener, a disintegrant, a binder, or a humectant, for example.

In some embodiments the filler is selected from cellulose powders (for example, see the Arbocel range such as Arbocel M80), soy protein powder, soy grits, silicon dioxide, wheat germ, or any combination of any two or more thereof.

In one embodiment the use of the filler absorbs any excess oils and fats, melted during extrusion, and prevents oil leakage.

In one embodiment a combination of fillers are used in the formulation. In an alternate embodiment a combination of one or more fillers is used with one or more diluents. In an alternate embodiment a combination of diluents are used in the formulation.

For example, one or more diluents may be used in combination with a cellulose powder such as Arbocell M80. Examples of diluents include starches and their derivatives (e.g. hydrogenated starch hydrosylate), celluloses and their derivatives (e.g. cellulose acetate), protein matrices (soy protein, dextrates, wheat gluten, whey, corn cob, corn gluten), carbohydrates (e.g. maltodextrin, polydextrose), sugars and sugar alcohols (glucose, lactose, fructose, maltose, dextrose, sucrose, maltitol, xylitol, isomalt, mannitol), silicates, calcium phosphates, calcium sulfate, dextrates, kaolin, magnesium carbonate, polymethacrylates, talc, salts (e.g. sodium chloride) or any combination of any two or more thereof.

In one embodiment the diluents may also serve a role in fat absorption, disintegration, binding, providing nutrition, lubrication or any combination of any two or more thereof. The diluent may also be used for taste masking or modifying texture, for example.

In one embodiment the composition comprises 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, or 90% by weight filler, diluent or filler and diluent, and useful ranges may be selected between any of these values (for example, from about 2 to about 40, about 2 to about 36, about 2 to about 30, about 2 to about 24, about 2 to about 22, about 2 to about 28, about 2 to about 24, about 2 to about 20, about 2 to about 4, about 4 to about 40, about 4 to about 30, about 4 to about 20, about 4 to about 10, about 8 to about 40, about 8 to about 36, about 8 to about 30, about 8 to about 28, about 8 to about 22, about 8 to about 18, about 8 to about 14, about 10 to about 40, about 10 to about 32, about 10 to about 26, about 10 to about 20, about 16 to about 40, about 16 to about 32, about 16 to about 24, about 16 to about 20, about 22 to about 40, about 22 to about 36, about 22 to about 30, about 22 to about 24, about 28 to about 40, about 28 to about 36, about 28 to about 30, about 32 to about 40, about 32 to about 34, about 24 to about 40, about 24 to about 38 or about 38 to about 40% by weight filler, diluent or filler and diluent).

In one embodiment the formulation comprises about 15% by weight filler, diluent or filler and diluent.

In one embodiment the chewable formulation comprises one or more binders.

Binding agents may be used to improve the binding properties of the powdered mass, to assist the formation of compact dosage units.

Any suitable binder known in the art may be used. In one embodiment the binder is selected from gums such as xanthan gum or guar gum, alginates, celluloses and their derivatives such as methylcellulose or microcrystalline cellulose, fats or lipids, starches and their derivatives, dextrins, celluloses and their derivatives, povidones, silicates, mineral oils, vegetable oils, polymethacrylates, polyethylene oxides, gums, waxes, chitosan, polycarbophil, agar, or carbomers, or any combination of any two or more thereof.

In some embodiments the binder is a dry binder such as Methocel A15 Premium (methylcellulose) and Avicel (microcrystalline cellulose+calcium phosphate dibasic). The inventors have found that both these binders have good ability to bind dry powders and undergo direct compaction.

Surprisingly, contrary to their traditional use, fats or lipids have also been found to be useful in the present invention as binders. The fats or lipids melt at extrusion temperature and harden again post-extrusion, binding the chew mass in a lipid matrix. Fats and lipids that are solid at room temperate but melt at temperatures above 30° C. (preferably 40-90° C.)

can also be used as a binder. For example, glyceryl distearate NF/glycerol distearate, having a melting point between 50-60° C. was found by the inventors to be useful in the present invention. Several other fats, such as glycerol monostearate (melting point: 54-64° C.), behenoyl polyoxyl-8-glycerides NF (drop point: 60-74 ° C.), hydrogenated coconut oil or hard fat (melting point: 42-44 ° C.) and shortening (melting point 46-48° C.) may also be useful.

In one embodiment the formulation comprises 0.1, 0.2, 0.3, 0.5, 0.5, 0.6, 0.7, 0.8, 0.9, 1, 2, 3, 4, 5, 6, 7, 8, 9, 0, 11, 12, 13, 14, 15, 16, 17, 18, 19, 20, 21, 22, 23, 24, 26, 27, 28, 29, 30, 31, 32, 33, 34, 35, 36, 37, 38, 39, 40, 41, 42, 43, 44, 45, 46, 47, 48, 49, or 50% % by weight binder, and useful ranges may be selected between any of these values (for example, from about 0.1 to about 50, from about 0.1 to about 40, from about 0.1 to about 30, from about 0.1 to about 25, from about 0.1 to about 20, from about 0.1 to about 15, about 0.1 to about 12, about 0.1 to about 7, about 0.1 to about 5, about 0.1 to about 1, about 0.1 to about 0.6, about 0.1 to about 0.5, about 0.1 to about 0.4, about 0.3 to about 50, about 0.3 to about 40, about 0.3 to about 30, about 0.3 to about 25, about 0.3 to about 20, about 0.3 to about 15, about 0.3 to about 12, about 0.3 to about 10, about 0.3 to about 7, about 0.3 to about 6, about 0.3 to about 5, about 03 to about 1, about 0.3 to about 0.8, about 0.5 to about 50, about 0.5 to about 40, about 0.5 to about 30, about 0.5 to about 25, about 0.5 to about 20, about 0.5 to about 15, about 0.5 to about 13, about 0.5 to about 10, about 0.5 to about 7, about 0.5 to about 6, about 0.5 to about 4, about 0.5 to about 1, about 0.5 to about 0.9, about 1 to about 50, about 1 to about 40, about 1 to about 30, about 1 to about 25, about 1 to about 20, about 1 to about 15, about 1 to about 12, about 1 to about 10, about 1 to about 7, about 1 to about 6, about 3 to about 50, about 3 to about 40, about 3 to about 30, about 3 to about 25, about 3 to about 20, about 3 to about 15, about 3 to about 13, about 3 to about 10, about 3 to about 8, about 3 to about 7, about 3 to about 5, about 5 to about 50, about 5 to about 40, about 5 to about 30, about 5 to about 25, about 5 to about 20, about 5 to about 15, about 5 to about 12, about 5 to about 10, about 5 to about 7, about 5 to about 6, about 8 to about 50, about 8 to about 40, about 8 to about 30, about 8 to about 25, about 8 to about 20, about 8 to about 15, about 8 to about 12, about 8 to about 10, about 11 to about 50, about 11 to about 40, about 11 to about 30, about 11 to about 25, about 11 to about 20, about 11 to about 15, about 11 to about 12 or about 13 to about 15% by weight binder).

In one embodiment, the formulation comprises 1, 2, 3, 4, 5, 6, 7, 8, 9, 10, 11, 12, 13, 14, 15, 16, 17, 18, 19, 20, 22, 24, 26, 28, 30, 32, 34, 36, 38, 40, 42, 44, 46, 48, or 50% weight binder and/or filler, and useful ranges may be selected between any of these values.

In one embodiment the binder is a gum such as guar gum or xanthan gum and is present in the formulation at about 0.2 to about 0.6, and more preferably 0.25 to about 0.5% by weight.

The binder may be added in the form of a liquid or solid. Filler-binders are typically in solid form.

In one embodiment the chewable formulation comprises one or more sweeteners.

Sweetening agents may be used to improve the palatability of the chewable treats.

Any suitable sweetener known in the art may be used. In one embodiment the sweetener may be a natural sweetener such as glucose, fructose, sucrose (e.g. icing sugar), lactose, dextrose, glycerol, sorbitol, xylitol, maltitol, lactitol, glycerol, an artificial sweetener such as aspartame, a saccharin, acesulfame, sodium cyclamate, or any combination of any two or more thereof. In another embodiment, the sweetener is selected from glucose, fructose, sucrose, lactose, dextrose, glycerol, sorbitol, xylitol, maltitol, lactitol, glycerol, aspartame, a saccharin, acesulfame, sodium cyclamate, stevia, rebaudioside A, thaumatin, sucralose, licorice and its derivatives, alitame, neotame, neohesperidin, or dihydrochalcone, or any combination of any two or more thereof.

In one embodiment, the chewable formulation comprises one or more palatability enhancers. Palatability enhancers improve the palatability of the chewable treats. Advantageously, palatability enhancers may improve the palatability of chewable formulations comprising bitter, acrid, obnoxious, unpleasant, or otherwise unpalatable nutritional or pharmaceutically active agents.

In one embodiment, the chewable formulation comprises 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% by weight palatability enhancer, and useful ranges may be selected between any of these values (for example, from about 0.5 to about 30, from about 0.5 to about 25, from about 0.5 to about 20, from about 0.5 to about 15, about 1 to about 30, about 1 to about 25, about 1 to about 20, about 1 to about 15, about 5 to about 30, about 5 to about 25, about 5 to about 20, or about 5 to about 15).

In one embodiment, the palatability enhancer is a taste masking agent, a flavour potentiator, an aroma modifier, or a taste modifier, or any combination of any two or more thereof.

In one embodiment, the taste modifier is a bitter blocker.

In one embodiment, the bitter blocker is selected from polyethoxylated glycerol fatty acid esters, such as polyethylated castor oil (e.g. cremphor), cyclodextrins (e.g. (β-cyclodextrin), flavanones (e.g. homoeriodictyol sodium salt), alkaline earth metal salts (e.g. zinc sulphate, magnesium sulphate), or celluloses and their derivatives (e.g. carboxymethylcellulose sodium salt), or any combination of any two or more thereof.

In one embodiment, the flavour potentiator is a sweetness enhancer.

In one embodiment, the sweetness enhancer is selected from pyridinium salts (e.g. alapyridaine), substituted benzoic acids (e.g. 2,4-dihydroxybenzoic acid), and positive allosteric modulators.

In one embodiment, the taste masking agent is selected from polyethoxylated glycerol fatty acid esters, such as polyethylated castor oil (e.g. cremophor), fats, or lipids, or any combination of any two or more thereof.

In one embodiment, the aroma modifier is selected from a flavour oil or flavour concentrate.

The inventors have also found that glycerin, typically used as a plasticizer and humectant, may also have additional sweetening property.

In one embodiment the formulation comprises 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80% by weight sweetener, and useful ranges may be selected between any of these values (for example, from about 0.1 to about 80, from about 0.1 to about 70, from about 0.1 to about 60, from about 0.1 to about 50, from about 0.1 to about 40, from about 0.1 to about 45, from about 0.1 to about 30, from about 0.1 to about 25, from about 0.1 to about 20, from about 0.5 to about 80, from about 0.5 to about 70, from about 0.5 to about 60, from about 0.5 to about 50, from about 0.5 to about 40, from about 0.5 to about 45, from about 0.5 to about 30, from about 0.5 to about 25, from about 0.5 to about 20, from about 1 to about 80, from about 1 to about 70, from about 1 to about 60, from about 1 to about 50, from about 1 to about 40, from about 1 to about 45, from about 1 to about 30, from about 1 to about 25, from about 1 to about 20, from about 5 to about 30, about 5 to about 25, about 5 to about 20, about 5 to about 25, about 5 to about 20, about 8 to about 30, about 8 to about 25, about 8 to about 20, about 8 to about 14, about 8 to about 12, about 10 to about 30, about 10 to about 25, about 10 to about 21, about 10 to about 14, about 14 to about 30, about 14 to about 25, about 14 to about 21, about 14 to about 19, about 15 to about 30, about 15 to about 26, about 15 to about 20, about 18 to about 30, about 18 to about 27, about 18 to about 25, about 18 to about 20, about 22 to about 30, about 22 to about 18, about 22 to about 25, about 25 to about 30 or about 26 to about 30% by weight sweetener).

In one embodiment, the chewable formulation comprises one or more flavouring agents, palatability enhancers, a taste masking agents, or aroma modifiers, or any combination of any two or more thereof.

In one embodiment the formulation comprises 1, 2, 3, 4, 5, 6, 7, 8, 9, 10, 11, 12, 13, 14, 15, 16, 17, 18, 19, 20, 21, 22, 23, 24, or 25% by weight flavouring agent, palatability enhancers, a taste masking agents, or aroma modifiers, or any combination of any two or more thereof, and useful ranges may be selected between any of these values.

In one embodiment the chewable formulation comprises one or more flavouring agents.

Flavouring agents may be used to improve the palatability of the chewable tablets. Any type of flavouring agent can be used provided it improves the palatability of the product, typically by improving either its taste and/or smell. Use of a flavouring agent may also assist dose compliance. Flavours can be natural (derived from animal or plant sources), semi synthetic, or artificial. In one embodiment, the flavouring agent is an artificial flavouring agent, semi-synthetic flavouring agent, a natural flavouring agent, or nature identical flavouring agent.

The flavouring agent may be solid, semi-solid or liquid. For example, the flavouring agent may be in the form of a powder, granules, a gel, beads, a liquid, a concentrate or a mince.

The flavouring agent used may depend on animal for which the formulation is intended. For example, a meat flavoured flavouring agent may be used for a formulation intended for administration to a dog, while a fruit (e.g. apple) flavoured flavouring agent may be used for a formulation intended for administration to a horse.

The flavouring agent may, for example, have a sweet, fruity, dairy, meat, poultry, seafood, or plant extract flavour. Any suitable flavouring agent may be used.

In one embodiment, the flavouring agent is fruit, meat (e.g. pork, chicken, beef, fish), vegetable, dairy, honey, or plant derived, or is artificial.

Examples of flavouring agents include beef flavour, artificial beef type flavour, beef mince, pork liver powder, cheese flavour, roast chicken hickory smoke, stewed beef flavoring, chicken fat, roast pork, roast chicken flavour, savoury flavouring, fish flavouring, butter caramel, vanilla, creamy vanilla, apple, sweet apple, marshmallow, citrus, plant extract flavour oils, honey, dairy flavouring agents, bacon, tuna fish, and the like.

In one embodiment the flavouring agent is selected from artificial beef type flavour, beef mince, pork liver powder, cheese flavour, roast chicken hickory smoke, or any combination of any two or more thereof. Other flavouring agents known in the art may also be used.

In one embodiment the formulation comprises 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, or 25% by weight flavouring agent, and useful ranges may be selected between any of these values (for example, from about 0.1 to about 25, from about 0.1 to about 20, from about 0.1 to about 15, from about 0.1 to about 13, from about 0.1 to about 10, from about 0.1 to about 8, from about 0.1 to about 5, 0.2 to about 25, from about 0.2 to about 20, from about 0.2 to about 15, from about 0.2 to about 13, from about 0.2 to about 10, from about 0.2 to about 8, from about 0.2 to about 5, from about 0.5 to about 25, from about 0.5 to about 20, from about 0.5 to about 15, from about 0.5 to about 13, from about 0.5 to about 10, from about 0.5 to about 8, from about 0.5 to about 5, from about 1 to about 25, from about 1 to about 20, from about 1 to about 15, about 1 to about 13, about 1 to about 10, about 1 to about 8, about 1 to about 5, about 1 to about 4, about 2 to about 15, about 2 to about 10, about 2 to about 9, about 2 to about 6, about 2 to about 5, about 2 to about 4, about 5 to about 15, about 5 to about 12, about 5 to about 10, about 5 to about 8, about 8 to about 15, about 8 to about 10, about 10 to about 15, about 12 to about 15 or about 13 to about 15% by weight flavouring agent). The amount of used depends on the flavouring agent.

In one embodiment the chewable formulation comprises one or more plasticizers.

Plasticizers may be used to the formulation to improve its plasticity, and malleability. Plasticizers make the extrusion feel ductile and easy to shape.

In one embodiment the plasticizer may be selected from alcohols, glycols (such as propylene glycol), lanolin, wool fat, liquid paraffin, mineral oil, petrolatum, benzyl phenylformate, chlorobutanol, diethyl phthalate, glycerol, polyethylene glycol, propylene glycol, sorbitol, triacetin, benzyl phenyl formate, PLGA, methacrylates, phthalates, acetyltributyl citrate, acetyltriethyl citrate, castor oil, dibutyl sebacate, tributyl citrate, triethyl citrate, or any combination of any two or more thereof. Other plasticizers known in the art may also be used.

Surprisingly, contrary to their traditional use, fats or lipids have also been found to be useful in the present invention as plasticizers. Fats or lipids used in the formulation melt at the extrusion temperature to function as a plasticizer.

The inventors have also determined that plasticizers such as propylene glycol and glycerine can have multiple roles, as they can also function as humectants and reduce water activity of the chewable formulation.

In one embodiment the chewable formulation comprises 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45% by weight plasticizer, and useful ranges may be selected between any of these values (for example, from about 5 to about 45, from about 5 to about 40, from about 5 to about 35, from about 5 to about 30, about 5 to about 26, about 5 to about 22, about 5 to about 15, about 5 to about 12, about 5 to about 12, about 5 to about 8, about 8 to about 45, about 8 to about 40, about 8 to about 35, about 8 to about 30, about 8 to about 28, about 8 to about 25, about 8 to about 21, about 8 to about 16, about 8 to about 12, about 10 to about 45, about 10 to about 40, about 10 to about 35, about 10 to about 30, about 10 to about 26, about 10 to about 22, about 10 to about 18, about 10 to about 14, about 14 to about 45, about 14 to about 40, about 14 to about 35, about 14 to about 30, about 14 to about 25, about 14 to about 20, about 18 to about 45, about 18 to about 40, about 18 to about 35, about 18 to about 30, about 18 to about 26, about 18 to about 23, about 18 to about 20, about 20 to about 45, about 20 to about 40, about 20 to about 35, about 20 to about 30, about 20 to about 25, about 22 to about 45, about 22 to about 40, about 22 to about 35, about 22 to about 30, about 22 to about 25, about 25 to about 45, about 25 to about 40, about 25 to about 35, about 25 to about 30 or about 27 to about 30% by weight plasticizer).

In one embodiment, the placticiser is a liquid at standard temperature and pressure.

In one embodiment the chewable formulation comprises one or more humectants.

Humectants may be used to reduce the water activity. Humectants bind any water, if present, to themselves, so that free moisture is unavailable for microbial contamination or chemical breakdown of active ingredient. Humectants may also prevent the product from drying out.

In one embodiment the humectant is selected from sodium and potassium chloride, benzalkonium chloride, aluminium silicate, sodium propionates, sodium and potassium phosphates, sugars, sulfites, hydrogenated starch hydrosylate, etc. Liquid humectants include, but are not limited to, glycols, polyols, sugar alcohols, vegetable oils and mineral oil, hydrogenated vegetable oils, hydrocarbons, triacetin, liquid paraffin, or any combination of any two or more thereof. Other humectants known in the art may also be used.

The humectants may be in the form of a solid or liquid. In one embodiment the humectant is in a solid form.

The inventors have surprisingly found that propylene glycol and glycerin also function as humectants and reduce the water activity of the chewable treats. As such, in certain embodiments wherein the chewable formulation comprises propylene glycol and/or glycerin, it may not be necessary to include an antimicrobial agent in the formulation to prevent microbial contamination.

In some embodiments the chewable formulation may also comprise solid humectants, such as salt and sugar. These humectants work together to reduce the overall water activity of the dosage unit and make it less susceptible to microbial contamination and water induced chemical degradation.

In one embodiment the chewable formulation comprises 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, or 90% by weight humectant, and useful ranges may be selected between any of these values (for example, from about 0.2 to about 90, from about 0.2 to about 80, from about 0.2 to about 70, from about 0.2 to about 60, from about 0.2 to about 50, from about 0.2 to about 40, from about 0.2 to about 30, from about 0.2 to about 20, from about 0.2 to about 10, from about 0.2 to about 5, about 0.2 to about 4, about 0.2 to about 2, about 0.2 to about 1, about 0.2 to about 0.7, about 0.6 to about 90, about 0.6 to about 80, about 0.6 to about 70, about 0.6 to about 60, about 0.6 to about 50, about 0.6 to about 40, about 0.6 to about 30, about 0.6 to about 20, about 0.6 to about 10, about 0.6 to about 5, about 0.6 to about 4, about 0.6 to about 2, about 0.6 to about 1, about 0.6 to about 0.8, about 0.8 to about 90, about 0.8 to about 80, about 0.8 to about 70, about 0.8 to about 60, about 0.8 to about 50, about 0.8 to about 40, about 0.8 to about 30, about 0.8 to about 20, about 0.8 to about 10, about 0.8 to about 5, about 0.8 to about 4, about 0.8 to about 2, about 0.8 to about 1, about 1 to about 90, about 1 to about 80, about 1 to about 70, about 1 to about 60, about 1 to about 50, about 1 to about 40, about 1 to about 30, about 1 to about 20, about 1 to about 10, about 1 to about 5, about 1 to about 4, about 1 to about 3, about 1 to about 2, about 2 to about 90, about 2 to about 80, about 2 to about 70, about 2 to about 60, about 2 to about 50, about 2 to about 40, about 2 to about 30, about 2 to about 20, about 2 to about 10, about 2 to about 5, about 2 to about 4, about 3 to about 90, about 3 to about 80, about 3 to about 70, about 3 to about 60, about 3 to about 50, about 3 to about 40, about 3 to about 30, about 3 to about 20, about 3 to about 10, about 3 to about 5, about 5 to about 90, about 5 to about 80, about 5 to about 70, about 5 to about 60, about 5 to about 50, about 5 to about 40, about 5 to about 30, about 5 to about 20, about 5 to about 10, about 10 to about 90, about 10 to about 80, about 10 to about 70, about 10 to about 60, about 10 to about 50, about 10 to about 40, about 10 to about 30, about 10 to about 20, about 15 to about 90, about 15 to about 80, about 15 to about 70, about 15 to about 60, about 15 to about 50, about 15 to about 40, about 15 to about 30, or about 15 to about 20% by weight humectant).

In one embodiment, the chewable formulation comprises less than about 45, 40, 35, 30, 25, 20, 15, 10, or 5% liquid humectant.

In one embodiment the chewable formulation comprises one or more lubricants.

Lubricants may be used to assist the formulation to slip through the extruder without friction.

In one embodiment lipids, fat or lipids and fats are added to the formulation to provide lubrication during extrusion.

The fats and lipids used are typically solid at room temperature, but melt partially or completely under extrusion conditions. The melted fats/lipid further improve binding and plasticity of the chew formulation. The plastic extrusion feed is then shaped in the extruder die under very high pressure to form the chewable treats. Once out of the extruder, the fats/lipids solidify again and the chewable treats harden, to compact semi-soft dosage units.

In one embodiment the fats and lipids are selected from shortening, tallow, stearates, glyceryl distearate, glycerol monostearate, behenoyl polyoxy-8-glyceride, hydrogenated coconut oil, hard fat, or any combination of any two or more thereof. Other fats/lipids known in the art may also be used.

In one embodiment the chewable formulation comprises 2, 3, 4, 5, 6 ,7 8, 9, 10, 11, 12, 13, 14, 15, 16, 17, 18% by weight lubricant, and useful ranges may be selected between any of these values (for example, from about 2 to about 18, about 2 to about 16, about 2 to about 14, about 2 to about 12, about 2 to about 10, about 2 to about 8, about 2 to about 6, about 4 to about 18, about 4 to about 17, about 4 to about 14, about 4 to about 12, about 4 to about 10, about 4 to about 8, about 5 to about 18, about 5 to about 17, about 5 to about 16, about 5 to about 12, about 5 to about 10, about 5 to about 7, about 7 to about 18, about 7 to about 15, about 7 to about 14, about 7 to about 12, about 7 to about 10, about 9 to about 18, about 9 to about 16, about 9 to about 14, about 9 to about 11, about 10 to about 18, about 10 to about 17, about 10 to about 14, about 10 to about 12, about 12 to about 18, about 12 to about 17,12 to about 14, about 15 to about 18, about 15 to about 17 or about 16 to about 18% by weight lubricant).

In one embodiment the chewable formulation comprises an antioxidant. Antioxidants may be used to protect the active ingredient from oxidation.

In one embodiment the antioxidant is selected from propyl gallate, ascorbic acid and its derivatives, sodium formaldehyde sulfoxylate, malic acid, fumaric acid, editic acid, thiols, polyphenols, sodium EDTA, sodium ascorbate, sodium metabisulfite, butylated hydroxytoluene, butylated hydroxyanisole, or natural substances such as flavanoids, tocopherols, carotenes, cysteine, or any combination of any two or more thereof. Other antioxidants known in the art may also be used.

The inventors have surprisingly found that the use of ascorbyl palmitate and α-tocopherols are synergistic in the formulation of the present invention.

The amount of antioxidant used may depend on, for example, the nutritionally or pharmaceutically active agent present in the formulation and its concentration.

In one embodiment the chewable formulation comprises about 0.0005, 0.001, 0.005, 0.01, 0.05, 0.1, 0.2, 0.3, 0.4, 0.5, 1, 1.5, 2, 2.5, 3, 3.5, 4, 4.5, or 5% by weight antioxidant, and useful ranges may be selected between any of these values (for example, from about 0.0005 to about 5, from about 0.0005 to about 3, from about 0.0005 to about 1, from about 0.0005 to about 0.5, from about 0.001 to about 5, from about 0.001 to about 3, from about 0.001 to about 2, from about 0.001 to about 1, from about 0.001 to about 0.5, from about 0.001 to about 0.2, from about 0.005 to about 5, from about 0.005 to about 3, from about 0.005 to about 1, from about 0.005 to about 0.5, from about 0.005 to about 0.2, from about 0.01 to about 5, from about 0.01 to about 3, from about 0.01 to about 1, from about 0.01 to about 0.5, from about 0.01 to about 0.2 by weight antioxidant).

In one embodiment, the chewable formulation comprises a surfactant.

In one embodiment, the formulation comprises about 0.01, 0.02, 0.03, 0.04, 0.05, 0.06, 0.07, 0.08, 0.09, 0.1, 0.15, 0.2, 0.3, 0.4, 0.5, 1, 2, 3, 4, 5, 6, 7, 8, 9, 10, 11, 12, 13, 14, 15, 16, 17, 18, 19, or 20% surfactant by weight, and useful ranges may be selected between any of these values (for example, from about 2 to about 10% surfactant by weight).

In one embodiment, the surfactant is selected from propylene glycol esters (e.g. propylene glycol monocaprylate), PEGs, PEG esters, fatty acid glycerides (e.g. lauroyl glycerides), and anionic surfactants (e.g. sodium lauryl sulfate).

In one embodiment, the chewable formulation comprises a solubility enhancer, bioavailability enhancer, or a solubility enhancer and bioavailability enhancer. The solubility enhancer and/or bioavailability enhancer enhances the water solubility and/or bioavailability of the nutritional or pharmaceutically active agent in the animal to which the formulation is to be administered.

In one embodiment, the chewable formulation comprises about 0.01, 0.1, 0.5, 1, 2, 3, 4, 5, 6, 7, 8, 9, 10, 11, 12, 13, 14, 15% by weight solubility enhancer, bioavailability enhancer, or solubility enhancer and bioavailability enhancer, and useful ranges may be selected between any of these values (for example, from about 0.01 to about 15, from about 0.01 to about 10, from about 0.01 to about 8, from about 0.01 to about 6, from about 0.01 to about 5, from about 0.1 to about 15, from about 0.1 to about 10, from about 0.1 to about 8, from about 0.1 to about 6, from about 0.1 to about 5, from about 0.5 to about 15, from about 0.5 to about 10, from about 0.5 to about 8, from about 0.5 to about 6, from about 0.5 to about 5, from about 1 to about 15, from about 1 to about 14, from about 1 to about 13, from about 1 to about 12, from about 1 to about 11, from about 1 to about 10, from about 1 to about 9, from about 1 to about 8, from about 1 to about 7, from about 1 to about 6, or from about 1 to about 5% solubility enhancer, bioavailability enhancer, or solubility enhancer and bioavailability enhancer by weight). The amount of solubility or bioavailability enhancing agent used depends on the nutritional or pharmaceutically active agent, and the amount in which the nutritional or pharmaceutically active agent is present.

In one embodiment, the solubility enhancer is selected from surfactants, complexing agents, buffers, or ionic salts, or any combination of any two or more thereof.

In one embodiment, the solubility enhancer is selected from sodium lauryl sulphate, polysorbates, spans, polyethylene glycols, bile salts, lecithin, phospholipids, poloxamers, polyoxyl 35 castor oil, medium chain mono- and diglycerides, propylene glycol monolaurate, polyvinyl caprolactam-polyvinyl acetate-polyethylene glycol graft copolymer, tocopheyl polyethylene glycol succinate, polyoxyl-15-hydroxystearate, lauroyl polyoxyl-32 glycerides, nonionic triblock copolymers, polyoxyethylene (8) caprylic/capric glycerides, PEG-40 hydrogenated castor oil, diethylene glycol monoethyl ether and caprylocaproyl macrogol glycerides, or any combination of any two or more thereof. Any other suitable solubility enhancers known in the art may be used.

In one embodiment, the bioavialbility enhancer is penetration enhancer.

In one embodiment, the bioavailability enhancer is a naturally or herbally derived bioavailability enhancer.

In one embodiment, the bioavailability enhancer is selected from quercetin, genistein, lysergol, naringin, sinomenine, piperine, glycyrrhizin, nitrile glycoside, cuminum cyminum, niaziridin, piperine, or allicine.

In one embodiment, the chewable formulation comprises one or more complexing agents.

In one embodiment, the nutritional or pharmaceutically active agent is complexed or conjugated with one or more complexing agents.

In one embodiment, the complexing agent is selected from EDTA, choleic acid, cyclodextrins (e.g. (β-cyclodextrin), cyclic glucose oligomers, or polymers such as polethylene glycols, methyl cellulose, carboxy methyl cellulose and polyvinylpyrollidine, or any combination of any two or more thereof.

In one embodiment, the chewable formulation comprises about 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 60, 70 or 80% complexing agent by weight, and useful ranges may be selected between any of these values (for example, from about 0.1% to about 30% complexing agent by weight). The amount used depends on the concentration of API and its affinity for the complexing agent.

In one embodiment, the molar ratio of API:complexing agent is about 4:1, 2:1, 1:1, 1:2, 1:3, 1:4, 1:5, 1:6, 1:7, 1:8, 1:9, or 1:10, and useful ranges may be selected between any of these values (for example, from about 1:1 to about 1:10.

In one embodiment, the chewable formulation comprises one or more coating agents.

In one embodiment, the nutritional or pharmaceutically active agent, optionally in granular form, are coated with the one or more coating agents.

In one embodiment, the chewable formulation comprises about 1% to about 20% coating agent by weight of the nutritional or pharmaceutically active agent.

In one embodiment, the coating agent is selected from polyethylene glycols, a wax, or a fatty acid, or a combination of any two or more thereof.

In one embodiment, the chewable formulation comprises a non-aqueous solvent, for example glycerol formal. The non-aqueous solvent may solubilise or enhance solubilization of the nutritional or pharmaceutically active agent. The non-aqueous solvent may also enhance the extrudability of the formulation and the consistency and texture of the chewable product.

In one embodiment, the chewable formulation comprises about 1, 2, 3, 4, 5, 6, 7, 8, 9, 10, 11, 12, 13, 14, 15, 16, 17, 18, 19, 20, 21, 22, 23, 24, or 25% by weight non-aqueous solvent or vehicle, and useful ranges may be selected between any of these values (for example, from about 1 to about 25, from about 1 to about 20, from about 1 to about 18, from about 1 to about 16, from about 1 to about 15, from about 1 to about 14, from about 1 to about 13, from about 1 to about 12, from about 1 to about 11, from about 1 to about 10, from about 1 to about 9, from about 1 to about 8, from about 1 to about 7, from about 1 to about 6, from about 1 to about 5, from about 2 to about 25, from about 2 to about 20, from about 2 to about 18, from about 2 to about 16, from about 2 to about 14, from about 2 to about 12, from about 2 to about 10, from about 2 to about 8, from about 2 to about 6, from about 5 to about 25, from about 5 to about 20, about 5 to about 15, or from about 5 to about 10 non-aqueous solvent or vehicle).Those skilled in the art will appreciate that the amount of non-aqueous solvent or vehicle used must be veterinary or pharmaceutically acceptable.

The non-aqueous solvent or vehicle is typically an organic solvent, which is pharmaceutically acceptable and chemically and biologically inert in the amount used. In one embodiment, the organic solvent is selected from dimethyl sulfoxide, N-methyl-2-pyrrolidone, ethylene glycol, diethylene glycol monoethyl ether glycofurol, glycerol formal, acetone, alcohol, tetrahydrofurfuryl alcohol, diglyme, dimethyl isosorbide, and ethyl lactate.

Further examples of organic solvents include alcohols (e.g. glycerol formal, methanol, ethanol, n-propanol, and iso-propanol), glycols (e.g. propylene glycol), ketones (e.g. acetone, methyl ethyl ketone), amide (e.g. dimethyl formamide), ethers (e.g. dimethyl isosorbide, 1,4-dioxane, diethyl ether, tetrahydrofuran, and tert-butyl methyl ether), halogenated solvents (e.g. dichloromethane and chloroform), sulfur containing solvents (e.g. dimethyl sulfoxide), aromatic hydrocarbons, aliphatic hydrocarbons (e.g. hexane and cyclohexane), esters (e.g. glycerol triacetate, ethyl acetate), carbonates (e.g. propylene carbonate), and nitriles (e.g. acetonitrile). Other suitable non-aqueous solvents will be apparent to those skilled in the art.

In one embodiment the chewable formulation comprises a colouring agent which may be used to improve the aesthetic appeal of the dosage units.

In one embodiment the colours are natural or artificial and may be selected from caramel or brown oxide for example. Other colouring agents known in the art may also be used.

In one embodiment the chewable formulation comprises a disintegrating agent. A disintegrating agent may be used to enable the chew to break down on contact with water to quickly release the active ingredient. This minimizes the risk of the chewable treat travelling unabsorbed through the gastrointestinal tract (GIT).

In one embodiment the disintegrating agent is selected from povidones, croscarmellose sodium, sodium starch glycollate, celluloses and their derivatives, starches and their derivatives, gelatin, silicon dioxide, or any combination of any two or more thereof. Other disintegrating agents known in the art may also be used.

In one embodiment the formulation comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30% by weight disintegrating agent, and useful ranges may be selected between any of these values (for example, from about 1 to about 30, from about 1 to about 25, from about 1 to about 20, from about 1 to about 15, about 1 to about 13, about 1 to about 10, about 1 to about 8, about 1 to about 5, about 1 to about 4, about 2 to about 30, about 2 to about 25, about 2 to about 20, about 2 to about 15, about 2 to about 10, about 2 to about 9, about 2 to about 6, about 2 to about 5, about 2 to about 4, about 5 to about 30, about 5 to about 25, about 5 to about 20, about 5 to about 15, about 5 to about 12, about 5 to about 10, about 5 to about 8, about 8 to about 30, about 8 to about 25, about 8 to about 20, about 8 to about 15, about 8 to about 10, about 10 to about 30, about 10 to about 25, about 10 to about 20, about 10 to about 15, about 12 to about 30, about 12 to about 25, about 12 to about 20, about 12 to about 15, about 13 to about 30, about 13 to about 25, about 13 to about 20, or about 13 to about 15% by weight disintegrating agent).

In one embodiment the chewable formulation comprises preservatives, buffering agents or preservatives and buffering agents. Preservatives may be used to prevent microbiological contamination and improve stability of the drug.

In one embodiment the preservative is selected from acids, alcohols, phenols, parabens, sorbates, thiols, phenylmercury salts, or any combination of any two or more thereof. Other preservatives known in the art may also be used.

In one embodiment a buffering agent may be added to adjust the pH of the formulation. This can sometimes help to improve the stability of certain active ingredients.

As mentioned previously, in some embodiments fats, lipids or fats and lipids are used in the formulation of the present invention. Any fats or lipids that are solid at room temperature, but melt above 30° C., preferably between 40-90° C. can be used. Fats/lipids function as lubricants, binders and plasticizers in this formulation. These include, but are not limited to stearates, glycerides, phospholipids, behenates, waxes, fatty acid esters, hydrogenated vegetable oils, animal fats, wool fat, hard fat, or any combination of any two or more thereof.

In one embodiment the chewable formulation comprises 2, 3, 4, 5, 6 ,7 8, 9, 10, 11, 12, 13, 14, 15, 16, 17, 18, 19, 20, 21, 22, 23, 24, or 25% by weight fats, lipids or fats and lipids, and useful ranges may be selected between any of these values (for example, from about 2 to about 25, from about 2 to about 20, from about 2 to about 18, about 2 to about 16, about 2 to about 14, about 2 to about 10, about 2 to about 8, about 2 to about 6, about 4 to about 25, about 4 to about 20, about 4 to about 18, about 4 to about 17, about 4 to about 14, about 4 to about 12, about 4 to about 10, about 4 to about 8, about 5 to about 25, about 5 to about 20, about 5 to about 18, about 5 to about 17, about 5 to about 16, about 5 to about 12, about 5 to about 10, about 5 to about 7, about 7 to about 25, about 7 to about 20, about 7 to about 18, about 7 to about 15, about 7 to about 14, about 7 to about 12, about 7 to about 10, about 9 to about 25, about 9 to about 20, about 9 to about 18, about 9 to about 16, about 9 to about 14, about 9 to about 11, about 10 to about 25, about 10 to about 20, about 10 to about 18, about 10 to about 17, about 10 to about 14, about 10 to about 12, about 12 to about 25, about 12 to about 20, about 12 to about 18, about 12 to about 17,12 to about 14, about 15 to about 25, about 15 to about 20, about 15 to about 18, about 15 to about 17, about 16 to about 25, about 16 to about 20, or about 16 to about 18% by weight fats, lipids or fats and lipids).

The chewable formulation may other conventional inert ingredients known in the art for use in chewable formulations.

In one embodiment, the chewable formulation comprises one or more food ingredients.

In one embodiment, the food ingredient is selected from oils (e.g. Soybean oil, Canola Oil, Peanut Oil, Palm Oil, Cod-liver oil), extracts (e.g. Rosemary extract, Grape extract, Vanilla extract, Citrus or lemon balm extract, Malt extract, or Other plant or vegetable, fruit based extracts), flours and starches (e.g. Oat Flour, Pea Flour, Pearled Barley Flour, Rice flour, Wheat Flour, Corn starch, Tapioca Starch, Potato starch or flour, Rye Grain flour, Cereal Flour), and others such as Milk Protein, Dried whole milk or milk products, Bran, Carrageenan, Pectin, and Menthol.

The ingredients used in the formulation are typically food grade quality or higher (e.g. generally regarded as safe (GRAS) and/or pharmaceutical grade). Mixtures of ingredients of different grades may be used.

As described herein, some of the ingredients used in the chewable formulation can be multifunctional. For example, sucrose can be used as a filler/diluent, binder and as a sweetening agent, and starches can be used as a filler/diluent, binder and as a disintegrating agent.

In one embodiment, the formulation comprises about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40% by weight liquid ingredients, and useful ranges may be selected between any of these values (for example, from about 10 to about 40, from about 10 to about 35, from about 10 to about 30, from about 10 to about 25, from about 15 to about 40, from about 15 to about 35, from about 15 to about 30, or from about 15 to about 25).

In another aspect the invention relates to a method of manufacturing a shelf stable chewable formulation 8 comprising mixing a nutritional or pharmaceutically active agent 1 with a fat, lipid or fat and lipid 3 to obtain a first composition 4, optionally adding one or more plasticizers 5 to the first mixture to obtain a second composition 6, and extruding the first composition 4 or second composition 6 under conditions effective to at least partially melt the fat, lipid, or fat and lipid, thereby providing the chewable formulation, and wherein the method of manufacture does not include the addition of water.

In one embodiment, the fat, lipid or fat and lipid 3 acts as a plasticiser and the first composition 4 is extruded.

In one embodiment, one or more plasticisers 5 are added to the first mixture to obtain a second composition 6, and the second composition 6 is extruded 7.

In one embodiment, the extrusion 7 is carried out at a temperature and/or pressure sufficient to at least partially melt the fat, lipid, or fat and lipid.

In one embodiment, the conditions are sufficient to melt at least 10, 15, 20, 25, 30, 35, 40, 45, 50, 55, 60, 65, 70, 75, 80, 85, 90, 95% of the fat, lipid, or fat and lipid.

In one embodiment, the conditions are effective to completely melt the fat, lipid, or fat and lipid.

In one embodiment the invention relates to a method of manufacturing an extruded chewable formulation 8 comprising mixing a nutritional ingredient or an effective amount of a pharmaceutically active agent with a fat, lipid or fat and lipid 3 to obtain a first composition 4, adding one or more plasticizers 5 to the first mixture to obtain a second composition 6, extruding 7 the second composition at a temperature sufficient to melt the fat and lipid, and allowing the extruded second composition to cool to room temperature thereby providing the chewable formulation 8, and wherein the method of manufacture does not include the addition of water.

In one embodiment, the nutritional or pharmaceutically active agent is, prior to the addition of the plasticiser, combined with one or more ingredients selected from:
 a filler, diluent or filler and diluent,
 a binder,
 a sweetener,
 a flavouring agent,
 a humectant,
 a fat, lipid or fat and lipid,
 an antioxidant,
 a colouring agent,
 a disintegrating agent,
 a preservative, buffering agent, or preservative and buffering agent,
 a lubricant,
 a complexing agent,
 a coating agent,
 a surfactant,
 a solubility enhancer, bioavailability enhancer, or a solubility enhancer and a bioavailability enhancer,
 a palatability enhancer, or
 a non-aqueous solvent or vehicle, or
  any combination of any two or more thereof to form a pre-composition 2 or first composition 4.

In one embodiment, the one or more ingredients are in a dry state. In one embodiment, the one or more ingredients are not in liquid form.

In one embodiment, the nutritional or pharmaceutically active agent is combined with the one or more ingredients, prior to the addition of the fat, lipid or fat and lipid.

In one embodiment the nutritional ingredient or an effective amount of a pharmaceutically active agent is first (i.e. prior to the addition of the fat, lipid or fat and lipid) combined with
 a filler,
 a diluent,
 a sweetener,
 a flavouring agent,
 a binder,
 a disintegrating agent, or
  any combination of two or more of the above to form a pre-composition 2.

In one embodiment the pre-composition 2 is a dry mixture of ingredients.

In one embodiment the fat, lipid, or fat and lipid 3 are pulverised before being added.

In one embodiment a plasticiser 5 is added to the second composition.

In one embodiment, the plasticiser is in the form of a liquid.

It should be appreciated that the fat, lipid, or fat and lipid can also act as a plasticiser. In this case, in some embodiments, following the addition of the fat, lipid, or fat and lipid, further plasticiser is not added.

In one embodiment, the method of manufacture may be carried out without applying heat. Heating during the manufacturing process may adversely impact on the stability of the nutritional or pharmaceutically active agent.

In one embodiment, the extrusion is carried out without applying heat. In such embodiments, the heat generated in the extruder due to shear is sufficient to at least partially melt the fat, lipid or fat and lipid; it is not necessary to apply heat from an external source.

In one embodiment extrusion is carried out at a temperature of about 20, 22, 24, 26, 28, 30, 32, 34, 36, 38, 40, 42, 44, or 45° C., and useful ranges may be selected between any of these values (for example, the extrusion may be carried out at a temperature from about 20 to about 45, from about 20 to about 40, from about 20 to about 30° C.). In one embodiment, the extrusion is carried out at a temperature of less than about 45, 44, 42, 40, 38, 36, 34, 32, 30, 28, 26, 24, 22, or 20° C.

In one embodiment the extrusion is performed under pressure sufficient to bind the ingredients together.

In one embodiment the second composition is blended prior to extrusion.

In one embodiment a planetary mixer is used to carry out the blending.

In one embodiment the extrusion is carried out as a single extrusion step.

In one embodiment, the method of manufacture comprises co-extruding at least one additional composition. The at least one additional composition may comprise any of the ingredients described herein with respect to the first or second composition. Co-extruding at least one additional composition provides a chewable formulation in the form of a co-extrudate.

The plasticizers (propylene glycol and glycerin) are added to the powder mass to increase plasticity and give the powder mass a dough-like consistency.

During extrusion, the feed is subjected to a temperature and pressure under which the fats/lipids melt and bind the powders together. They also improve plasticity of the extrusion feed and lubricate it, thus preventing sticking/picking to the extruder dies.

At room temperature the extrudates cool again and become slightly harder. The diluents and dry powder binders in the extrusion feed have high fat retention ability and prevent oil leakage.

Water, or any other aqueous ingredient, is not used during the formulation and manufacture of chewable treats, ensuring improved physical, chemical and microbiological stability. While there may be water in the formulation, any water is present in a bound state, and not a free state.

It will be appreciated that unbound water is water that is in a free state, and can take part in, for example, hydrolysis reactions. In the present invention any water present is effectively in a bound state. This effectively means that the water is not available for chemical reactions or use, for example by microorganisms.

In one embodiment at least 90, 91, 92, 93, 94, 95, 96, 97, 98, or 99% by weight of any water present in the chewable formulation is present in a bound state, and useful ranges may be selected between any of these values (for example, from about 95 to about 99, about 97 to about 99, about 96 to about 99, about 96 to about 98, about 97 to about 99, about 97 to about 98 or 98 to about 99 of any water present in the chewable formulation is in a bound state).

The amount of water present in a bound state in the formulation may be determined using any suitable method known in the art. Methods for measuring free moisture/water include, for example, water activity, and loss on drying (moisture balance). Methods for measuring free and bound water include, for example, Karl Fischer methods (e.g. KF titrators, KF oven/evaporators, moisture meters), and thermogravimetric analysis (TGA). The above methods are commonly used in pharmaceutical and food industries.

It will be apparent to those skilled in the art that it may be necessary to use more than one method in combination to determine the amount of free and bound water. One method that can be used quantify both unbound and bound moisture in the formulation is high resolution TGA.

The chewable formulation therefore has a low water activity (aw). A low water activity can be provided by including a sufficient amount of one or more humectants in the formulation.

In one embodiment the water activity (aw) of the chewable formulation is less than 0.93, 0.92, 0.91, 0.90, 0.89, 0.88, 0.87, 0.86, 0.85, 0.84, 0.83, 0.82, 0.81, 0.80, 0.79, 0.78, 0.77, 0.76, 0.75, 0.74, 0.73, 0.72, 0.71, 0.70, 0.69, 0.68, 0.67, 0.66, 0.65, 0.64, 0.63, 0.62, 0.61, 0.60, 0.59, 0.58, 0.57, 0.56, 0.55, 0.54, 0.53, 0.52, 0.51, 0.50, 0.49, 0.48, 0.47, 0.46, 0.45, 0.44, 0.43, 0.42, 0.41, 0.40, 0.38, 0.37, 0.36, 0.35, 0.34, 0.33, 0.32, 0.31, 0.30, 0.29, 0.28, 0.27, 0.26, 0.25, 0.24, 0.23, 0.22, 0.21, 0.20, 0.19, 0.18, 0.17, 0.16, 0.15, 0.14, 0.13, 0.12, 0.11, 0.10, and useful ranges may be selected between any of these values (for example, from about 0.93 to about 0.1, from about 0.93 to about 0.2, from about 0.93 to about 0.25, from about 0.93 to about 0.80, about 0.93 to about 0.83, about 0.93 to about 0.86, about 0.93 to about 0.89, about 0.92 to about 0.1, about 0.92 to about 0.2, from about 0.92 to about 0.25, about 0.92 to about 0.80, about 0.92 to about 0.83, about 0.92 to about 0.86, about 0.92 to about 0.89, about 0.91 to about 0.1, about 0.91 to about 0.2, from about 0.91 to about 0.25, 0.91 to about 0.80, about 0.91 to about 0.83, about 0.91 to about 0.86, about 0.91 to about 0.89, about 0.89 to about 0.1, about 0.89 to about 0.2, from about 0.89 to about 0.25, about 0.89 to about 0.8, about 0.89 to about 0.84, about 0.86 to about 0.1, about 0.86 to about 0.2, from about 0.86 to about 0.25, about 0.86 to about 0.8, about 0.86 to about 0.84, about 0.84 to about 0.1, about 0.84 to about 0.2, from about 0.84 to about 0.25, about 0.84 to about 0.8, about 0.84 to about 0.82, about 0.82 to about 0.1, about 0.82 to about 0.2, from about 0.82 to about 0.82, about 0.82 to about 0.80, from about 0.8 to about 0.1, from about 0.8 to about 0.15, from about 0.8 to about 0.2, from about 0.8 to about 0.25, from about 0.75 to about 0.1, from about 0.75 to about 0.15, from about 0.75 to about 0.2, from about 0.75 to about 0.25, from about 0.7 to about 0.1, from about 0.7 to about 0.15, from about 0.7 to about 0.2, from about 0.7 to about 0.25, from about 0.68 to about 0.1, from about 0.68 to about 0.15, from about 0.68 to about 0.2, from about 0.68 to about 0.25, from about 0.65 to about 0.1, from about 0.65 to about 0.15, from about 0.65 to about 0.2, from about 0.65 to about 0.25, from about 0.63 to about 0.1, from about 0.63 to about 0.15, from about 0.63 to about 0.2, from about 0.63 to about 0.25, from about 0.6 to about 0.1, from about 0.6 to about 0.15, from about 0.6 to about 0.2, from about 0.6 to about 0.25, from about 0.55 to about 0.1, from about 0.55 to about 0.15, from about 0.55 to about 0.2, from about 0.55 to about 0.25, from about 0.5 to about 0.1, from about 0.5 to about 0.15, from about 0.5 to about 0.2, from about 0.5 to about 0.25, from about 0.45 to about 0.1, from about 0.45 to about 0.15, from about 0.45 to about 0.2, or from about 0.45 to about 0.25).

In one embodiment the chewable formulation does not dry out during storage.

In one embodiment the chewable formulations are hard and "chewy", but not brittle, and resist deformation during storage and handling.

In one embodiment, the chewable formulation has a chewiness, hardness, compression energy, adhesion, cohesiveness, springiness, or modulus, or any combination of any two or more thereof (as measured by the method described in Example 7) sufficient to provide a chewable texture.

In one embodiment, the chewable formulation maintains a characteristic selected from chewiness, hardness, compression energy, adhesion, cohesiveness, springiness, and modulus, and any combination of any two or more thereof (as measured by the method described in Example 7) sufficient to provide a chewable texture.

In one embodiment, the chewable formulation has a chewiness of about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 11, 12, 13, 14, 15, 16, 17, 18, 19, or 20 N, and useful ranges may be selected between any of these values (for example, from about 0.1 to about 20, from about 0.1 to about 15, from about 0.1 to about 10, from about 0.1 to about 7, from about 0.5 to about 20, from about 0.5 to about 15, from about 0.5 to about 10, from about 0.5 to about 8, from about 0.5 to about 6, from about 1 to about 20, from about 1 to about 15, from about 1 to about 10, from about 1 to about 8, from about 1 to about 6, from about 2 to about 20, from about 2 to about 15, from about 2 to about 10, from about 2 to about 8, from about 2 to about 6 N.

In one embodiment, the chewable formulation has a hardness of about 1000, 950, 900, 850, 800, 750, 725, 700, 675, 650, 625, 600, 575, 550, 525, 500, 475, 450, 425, 400, 375, 350, 325, 300, 275, 250, 225, 200, 175, 150, 125, 100, 75, 50, 25, 20, 15, or 10 N, and useful ranges may be selected between any of these values (for example, from about 1000 to about 10, from about 1000 to about 25, from about 1000 to about 50, from about 750 to about 10, from about 750 to about 25, from about 750 to about 50, from about 500 to about 10, from about 500 to about 25, or from about 500 to about 50 N).

In one embodiment, the chewable formulation has a compression energy of energy of about 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2100, 2200, 2300, 2400, 2500, 2600, 2700, 2800, 2900, or 3000 N.mm, and useful ranges may be selected between any of these values (for example, from about 100 to about 3000, from about 100 to about 2500, from about 100 to about 2000, from about 100 to about 1750, from about 250 to about 3000, from about 250 to about 2500, from about 250 to about 2000, from about 250 to about 1750, from about 500 to about 3000, from about 500 to about 2500, from about 500 to about 2000, from about 500 to about 1900, from about 500 to about 1800, from about 500 to about 1750, from about 600 to about 3000, from about 600 to about 2500, from about 600 to about 2000, from about 600 to about 1900, from about 600 to about 1800, from about 600 to about 1750, from about 700 to about 3000, from about 700 to about 2500, from about 700 to about 2000, from about 700 to about 1900, from about 700 to about 1800, from about 700 to about 1750, from about 750 to about 3000, from about 750 to about 2500, from about 750 to about 2000, from about 750 to about 1900, from about 750 to about 1800, from about 750 to about 1750, from about 750 to about 1700, from about 750 to about 1650, from about 750 to about 1600, from about 750 to about 1550, or from about 750 to about 1500).

In one embodiment, the chewable formulation has an adhesion of about 0, −0.5, −1, −1.5, −2, −2.5, −3, −3.5, −4, −4.5, −5, −5.5, −6, −6.5, −7, −7.5, −8, −8.5, −9, −9.5, −10, −11, −12, −13, −14, −15, −16, −17, −18, −19, or −20 N.mm, and useful ranges may be selected between any of these values (for example, from about 0 to about −20, from about 0 to about −18, from about 0 to about −16, from about 0 to about −15, from about 0 to about −14, from about 0 to about −13, from about 0 to about −12, from about 0 to about −11, from about 0 to about −10, from about 0 to about −9, from about 0 to about −8, from about 0 to about −7, from about 0 to about −6, from about −0.5 to about −20, from about −0.5 to about −18, from about −0.5 to about −16, from about −0.5 to about −15, from about −0.5 to about −14, from about −0.5 to about −13, from about −0.5 to about −12, from about −0.5 to about −11, from about −0.5 to about −10, from about −0.5 to about −9, from about −0.5 to about −8, from about −0.5 to about −7, from about −0.5 to about −6, from about −1 to about −20, from about −1 to about −18, from about −1 to about −16, from about −1 to about −15, from about −1 to about −14, from about −1 to about −13, from about −1 to about −12, from about −1 to about −11, from about −1 to about −10, from about −1 to about −9, from about −1 to about −8, from about −1 to about −7, or from about −1 to about −6).

In one embodiment, the chewable formulation has a cohesiveness of about 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.25, 0.3, 0.35, 0.4, 0.45, or 0.5, and useful ranges may be selected between any of these values (for example, from about 0.01 to about 0.5, from about 0.01 to about 0.4, from about 0.01 to about 0.3, from about 0.01 to about 0.2, from about 0.01 to about 0.1, from about 0.03 to about 0.5, from about 0.03 to about 0.4, from about 0.03 to about 0.3, from about 0.03 to about 0.2, from about 0.03 to about 0.1, from about 0.05 to about 0.5, from about 0.05 to about 0.4, from about 0.05 to about 0.3, from about 0.05 to about 0.2, or from about 0.05 to about 0.1).

In one embodiment, the chewable formulation has a springiness of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40%, and useful ranges may be selected between any of these values (for example, from about 1 to about 40, from about 1 to about 35, from about 1 to about 30, from about 1 to about 25, from about 3 to about 40, from about 3 to about 35, from about 3 to about 30, from about 3 to about 25, from about 5 to about 40, from about 5 to about 35, from about 5 to about 30, from about 5 to about 25, from about 10 to about 40, from about 10 to about 35, from about 10 to about 30, or from about 10 to about 25).

In one embodiment, the chewable formulation has a modulus of about 1, 2, 3, 4, 5, 10, 15, 20, 25, 30, 35, 40, 45, 50, 55, 60, 65, 70, 75, 80, 85, 90, 95, 100, 110, 120, 130, 140, 150, 160, 170, 180, 190, or 200 N/mm, and useful ranges may be selected between any of these values (for example, from about 1 to about 200, from about 1 to about 150, from about 1 to about 100, from about 1 to about 75, from about 1 to about 60, from about 3 to about 200, from about 3 to about 150, from about 3 to about 100, from about 3 to about 75, from about 3 to about 60, from about 5 to about 200, from about 5 to about 150, from about 5 to about 100, from about 5 to about 75, from about 5 to about 60, from about 10 to about 200, from about 10 to about 150, from about 10 to about 100, from about 10 to about 75, from about 10 to about 60, from about 15 to about 200, from about 15 to about 150, from about 15 to about 100, from about 15 to about 75, from about 15 to about 60, from about 20 to about 200, from about 20 to about 150, from about 20 to about 100, from about 20 to about 75, from about 20 to about 60, from about 25 to about 200, from about 25 to about 150, from about 25 to about 100, from about 25 to about 75, or from about 25 to about 60).

In one embodiment the chewable formulations is capable of delivering a range of drug candidates, including nutritional supplements to an animal.

In one embodiment the chewable formulations may have good physical and chemical stability, providing at least 12, 13, 14, 15, 16, 17, 18, 19, 20, 21, 22, 23, 24, 25, 26, 27, 28, 29, 30, 31, 32, 33, 34, 35, or 36 months shelf life, and useful ranges may be selected between any of these values (for example, from about 12 to about 36, from about 12 to about 30, about 12 to about 26, about 12 to about 20, about 12 to about 17, about 13 to about 36, about 13 to about 30, about 13 to about 25, about 13 to about 17, about 13 to about 15, about 16 to about 36, about 16 to about 30, about 15 to about 30, about 15 to about 30, about 15 to about 27, about 15 to about 22, about 15 to about 19, about 14 to about 36, about 14 to about 30, about 14 to about 28, about 14 to about 22, about 14 to about 18, about 14 to about 17, about 17 to about 36, about 17 to about 30, about 17 to about 28, about 17 to about 23, about 17 to about 20, about 18 to about 36, about 18 to about 30, about 18 to about 27, about 18 to about 24, about 18 to about 22, about 20 to about 36, about 20 to about 30, about 20 to about 28, about 20 to about 26, about 25 to about 36, about 25 to about 30, about 25 to about 28, about or about 27 to about 30 months of shelf life).

In one embodiment the chewable formulation delivers at least 80% of the active ingredient loading within 10, 15, 20, 25, 30, 35, 40, 45, 50, 55, 60, 65, 70, 75, 80, 85, 90 or 95 minutes, and useful ranges may be selected between any of these values (for example, for example, from about 10 to about 95, from about 10 to about 75, from about 10 to about 60, from about 10 to about 45, from about 10 to about 30, from about 15 to about 95, from about 15 to about 75, from about 15 to about 60, from about 15 to about 45, from about 15 to about 30, from about 20 to about 95, from about 20 to about 75, from about 20 to about 60, from about 20 to about 45, from about 20 to about 30, from about 30 to about 95, from about 30 to about 75, from about 30 to about 60, from about 30 to about 45, from about 50 to about 95, about 50 to about 90, about 50 to about 80, about 50 to about 70, about 50 to about 60, about 55 to about 95, about 55 to about 85, about 55 to about 80, about 55 to about 70, about 60 to about 95, about 60 to about 90, about 60 to about 80, about 60 to about 70, about 65 to about 95, about 65 to about 90, about 65 to about 80, about 70 to about 95, about 70 to about 90, about 70 to about 80, about 75 to about 95, about 75 to about 90 or about 80 to about 90 minutes from delivery of the chewable ingredient to the target animal).

In one embodiment, the chewable formulation provides sustained delivery of the nutritional or pharmaceutically active ingredient over an extended period of time. In one embodiment, the active ingredient is delivered over 2, 4, 6, 8, 10, 12, 24, 48, 60, 72, 96, 120, 144, or 168 hours, and useful ranges may be selected between any of these values.

In one embodiment, the chewable formulation provides delayed delivery of the nutritional or pharmaceutically active ingredient. In one embodiment, delivery is delayed by about 1, 2, 3, 4, 5, 6, 8, 10, 12, 24, 48, or 72 hours, and useful ranges may be selected between any of these values.

The rate of release of the nutritional or pharmaceutically active agent from the chewable formulation may be modulated or controlled by, for example, the use certain controlled or sustained release agents (e.g. polymers) or by using excipients (e.g. disintegrants) that promote in rapid release, as appropriate.

In one embodiment, the release characteristics of the nutritional or pharmaceutically active agent are substantially maintained throughout the shelf-stable period.

In one embodiment, the chewable formulation delivers the nutritional or pharmaceutically active agent at substantially the same dose and rate throughout the shelf stable period.

Without wishing to be bound by theory, the applicant believes that in certain embodiments, there is no cross linking and/or polymerisation between the nutritional or pharmaceutically active agent and/or excipients or other ingredients in the formulation. Such cross-linking and/or polymerisation reduced the amount of nutritional or pharmaceutically active agent made available to the animal.

The chewable formulation is for treating an animal in need thereof. The suitability of the formulation for treating a particular disease or condition, for example, depends on the nutritional or pharmaceutically active agent(s) present in the formulation.

The term "treatment", and related terms, such as "treating" and "treat" as used herein, relates generally to treatment, of either a human or a non-human animal, in which some desired therapeutic effect is achieved. The therapeutic effect may, for example, be the inhibition of progress of a disease or condition, including a reduction in the rate of progress, a halt in the rate of progress, amelioration, and cure. Treatment as a prophylactic measure is also included. Treatment also includes combination treatments and therapies, in which two or more treatments or therapies are used, for example, sequentially or simultaneously, in combination.

The present invention provides use of a chewable formulation of the present invention for treating an animal in need thereof.

The present invention also provides a method of treating an animal in need thereof, comprising administering chewable formulation of the present invention.

The present invention also provides use of a composition as described herein in the manufacture of a chewable formulation of the present invention for treating an animal in need thereof.

The animal to be treated may be human or non-human. Non-human animals include, for example, production animals, such as, cattle, sheep, swine, deer, and goats; companion animals, such as, dogs, cats, and horses; zoo animals, such as, zebras, elephants, giraffes, and large cats; research animals, such as, mice, rats, rabbits, and guinea pigs; furbearing animals, such as, mink; birds, such as, ostriches, emus, hens, geese, turkeys, and ducks.

A person skilled in the art will be able to readily determine the appropriate dosage of administration for treating an animal. The dosage will depend upon the nutritional or pharmaceutically active agent(s) present in the formulation and may also depend on the frequency of administration, the sex, age, weight and general condition of the animal treated, the nature and severity of the condition treated, any concomitant diseases to be treated, and any other factors evident to those skilled in the art.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Dissolution of Carprofen

The dissolution of carprofen in four formulations (F1-4) was tested. The formulations are shown in Table 2 below. Formulations F1 and F2 were prepared by extruding the chew twice. Formulations F3 and F4 were prepared by extruding the chew once.

TABLE 2

Formulations F1-4

| No. | Ingredient | F1 | F2 | F3 | F4 |
|---|---|---|---|---|---|
| 1 | Carprofen | 3.2 | 3.2 | 3.2 | 3.2 |
| 2 | Ascorbyl Palmitate | 0.2 | 0.2 | 0.2 | 0.2 |
| 3 | Decanox (tocopherol) | 0.1 | 0.1 | 0.1 | 0.1 |
| 4 | Arbocel M80 (cellulose powder) | 14.5 | 15 | 13 | 13 |
| 5 | Avicel DG (microcrystalline cellulose 75% w/w and dibasic calcium phosphate 25% w/w) | 5 | 5 | 5 | 5 |
| 6 | Methocel A15 Premium (methylcellulose) | 7 | 7 | 7 | 7 |
| 8 | Beef Type Flavour | 5 | 10 | 10 | 10 |
| 9 | Icing Sugar | 20 | 19 | 19 | 19 |
| 10 | Sodium chloride | — | 2 | 2 | 2 |
| 11 | Precirol ATO5 (glycerol distearate) | 8 | 7.5 | 7.5 | 7.5 |
| 12 | Glycerine (vegetable) | 16 | 11 | 10 | 11 |
| 13 | Propylene Glycol | 11 | 12.5 | 12 | 12 |
| 14 | Pregelatinized maize starch | 10 | 7.5 | 6 | 5 |
| 15 | Sodium Starch Glycollate | — | — | 5 | — |
| 16 | Ac-Di-Sol (croscarmellose sodium) | — | — | — | 5 |
|   | Total | 100 | 100 | 100 | 100 |

Dissolution testing was carried out using 0.5 M phosphate buffer at 37° C. as the dissolution medium with a paddle Speed of 75.0 rpm. The dissolution apparatus used was USP Apparatus II without disk or sinker.

1. Formulations
1.1 Formulations 1 and 2

Three chewable treats were picked randomly from formulation 1 and 2 (F1 and F2) and dissolution of carprofen was tested. The results are shown in Table 3 and Table 4.

TABLE 3

Dissolution of carprofen from F1.

| Sample Name | Carprofen Released (% w/w) | | | | |
|---|---|---|---|---|---|
|  | 0 mins | 30 mins | 60 mins | 90 mins | 120 mins |
| 1 | 0.0 | 14.3 | 27.7 | 44.5 | 58.3 |
| 2 | 0.0 | 35.0 | 62.2 | 82.7 | 92.2 |
| 3 | 0.0 | 38.8 | 66.6 | 83.7 | 91.0 |
| Avg: | 0.0 | 29.4 | 52.2 | 70.3 | 80.5 |
| Std dev: | 0.0 | 13.2 | 21.3 | 22.3 | 19.2 |

TABLE 4

Dissolution of carprofen from F2.

| Sample Name | Carprofen Released (% w/w) | | | |
|---|---|---|---|---|
|  | 0 mins | 30 mins | 60 mins | 120 mins |
| 1 | 0.0 | 45.0 | 70.5 | 95.3 |
| 2 | 0.0 | 47.8 | 75.9 | 97.5 |
| 3 | 0.0 | 13.0 | 21.8 | 42.0 |
| Avg: | 0.0 | 35.2 | 56.0 | 78.3 |
| Std dev: | 0.0 | 19.4 | 29.8 | 31.4 |

1.2 Formulations 3 and 4

Three chewable treats were selected from the start, middle and end of the extrusion line and tested. Dissolution time of chewable treats obtained from the end of the extrusion line was slightly higher than that of chewable treats obtained from the start of the extrusion line. Table 5 summarizes dissolution data for F3 and Table 6 summarizes dissolution data for F4.

TABLE 5

Dissolution of carprofen from F3

| Sample Name | Carprofen Released (% w/w) | | | |
|---|---|---|---|---|
|  | 0 mins | 30 mins | 60 mins | 120 mins |
| 1 | 0.0 | 60.6 | 88.4 | 97.4 |
| 2 | 0.0 | 59.6 | 90.5 | 95.3 |
| 3 | 0.0 | 49.6 | 79.3 | 95.1 |
| Avg: | 0.0 | 56.6 | 86.1 | 95.9 |
| Std dev: | 0.0 | 6.1 | 6.0 | 1.3 |

TABLE 6

Dissolution of carprofen from F4

| Sample Name | Carprofen Released (% w/w) | | | |
|---|---|---|---|---|
|  | 0 mins | 30 mins | 60 mins | 120 mins |
| start | 0.0 | 77.8 | 99.5 | 100.8 |
| middle | 0.0 | 70.2 | 94.6 | 98.8 |
| end | 0.0 | 60.8 | 90.7 | 101.7 |
| Avg: | 0.0 | 69.6 | 94.9 | 100.4 |
| Std dev: | 0.0 | 8.5 | 4.4 | 1.5 |

2. Conclusion

We found that the dissolution of API from chewable treats decreases as the number of extrusions performed increases. More than 80% of the API was found to be released in the first 90 minutes.

Super disintegrants (croscarmellose sodium and sodium starch glycollate) can further improve dissolution and show up to 100% drug release in the first 90 minutes.

Example 2

Drug-Excipient Compatibility Studies in Dog Chewable Treats Containing Meloxicam 1. Experimental Design Drug-excipient compatibility studies were undertaken for meloxicam-containing chewable treats.

A series of formulations were prepared by sequentially subtracting one ingredient from each formulation, as outlined in Table 7. All formulations were extruded manually before storage.

TABLE 7

Meloxicam chewable treats prepared for compatibility studies.

| Ingredients | MLX-1 | MLX-2 | MLX-3 | MLX-4 | MLX-5 | MLX-6 |
|---|---|---|---|---|---|---|
| Meloxicam | 0.073 | 0.073 | 0.073 | 0.073 | 0.073 | 0.073 |
| Nutrisoy grits | 25 | | 25 | 25 | 25 | 25 |
| Icing Sugar | 23 | 23 | 23 | 23 | 23 | |
| Arbocel M80 (cellulose powder) | 16.627 | 41.627 | 20.627 | 16.627 | 16.627 | 39.627 |
| Pregelatinized Starch | 5 | 5 | 5 | 5 | 5 | 5 |
| Salt | 1 | 1 | 1 | 1 | 1 | 1 |
| Beef (flavour) | 4 | 4 | | 4 | 4 | 4 |
| Propylene Glycol | 9 | 9 | 9 | 9 | 17 | 9 |
| Glycerogelatin (10%) | 8 | 8 | 8 | | 8 | 8 |
| Shortening | 8 | 8 | 8 | 8 | | 8 |
| Ascorbyl palmitate | 0.2 | 0.2 | 0.2 | 0.2 | 0.2 | 0.2 |
| a-tocopherol | 0.1 | 0.1 | 0.1 | 0.1 | 0.1 | 0.1 |
| Glycerine | | | | 8 | | |
| Total | 100 | 100 | 100 | 100 | 100 | 100 |

1.1 Storage Conditions

All the formulations were stored for 1 month at 50° C. and for 6 months at 40° C.

2. Results

2.1 Appearance

At each time interval, the colour the meloxicam chewable treats had substantially darkened. Closer inspection revealed that this was due to darkening (or perhaps "toasting") of nutrisoy grits at elevated temperatures. Some darkening could also have been due to the beef flavouring.

2.2 Meloxicam Content

The results of meloxicam assay during the compatibility study are listed in Table 8. These results clearly show that formulations MLX-2 (no nutrisoy grits) and MLX-5 (no shortening fat) were relatively more stable that the rest of the formulations. Degradation of Meloxicam was, thus, attributed to nutrisoy grits and shortening fat, respectively.

TABLE 8

Percentage of meloxicam recovered from chewable treats after 6 months at 40° C.

| Sample Name | Meloxicam (% initial) | | | | % Difference |
|---|---|---|---|---|---|
| | 0 Month | 1 Month | 3 Months | 6 Months | 0-6 Months |
| MLX-1 | 100.00 | 94.56 | 95.54 | 88.15 | 11.85 |
| MLX-2 | 100.00 | 97.32 | 99.44 | 94.35 | 5.65 |
| MLX-3 | 100.00 | 94.32 | 93.49 | 88.78 | 11.22 |
| MLX-4 | 100.00 | 95.35 | 107.33 | 89.99 | 10.01 |
| MLX-5 | 100.00 | 96.41 | 101.38 | 94.62 | 5.38 |
| MLX-6 | 100.00 | 93.74 | 101.73 | 87.08 | 12.92 |

2.3 pH

A slight decrease in pH was observed in all formulations, except MLX-4 (no gelatin) and MLX-5 (no shortening fat) as shown in Table 9.

TABLE 9 pH of meloxicam chewable treats after 6 months at 40° C.

| Sample Name | pH | | | | % Difference |
|---|---|---|---|---|---|
| | 0 Month | 1 Month | 3 Months | 6 Months | 0-6 Months |
| MLX-1 | 5.94 | 6.0 | 5.9 | 5.9 | −0.78 |
| MLX-2 | 5.03 | 5.0 | 5.0 | 5.0 | −1.43 |
| MLX-3 | 6.23 | 6.3 | 6.2 | 6.1 | −2.42 |
| MLX-4 | 5.92 | 6.1 | NT* | | 0.15 |
| MLX-5 | 5.86 | 6.1 | 6.0 | 6.06 | 3.35 |
| MLX-6 | 5.65 | 6.0 | 5.9 | NT* | — |

NT*-Not tested due to insufficient sample

Example 3

Drug-Excipient Compatibility Studies in Chewable Treats Containing Carprofen 1. Experimental design A series of formulations were prepared by sequentially subtracting one ingredient from each formulation, as outlined in Table 10. All formulations were extruded manually before storage.

TABLE 10

Carprofen chewable treats prepared for compatibility studies.
Carprofen Dog Chews

| Ingredients | CAR-1 | CAR-2 | CAR-3 | CAR-4 | CAR-5 | CAR-6 |
|---|---|---|---|---|---|---|
| Carprofen | 3.2 | 3.2 | 3.2 | 3.2 | 3.2 | 3.2 |
| Nutrisoy grits | 25 | | 25 | 25 | 25 | 25 |
| Icing Sugar | 23 | 23 | 23 | 23 | 23 | |
| Arbocel M80 (cellulose powder) | 13.5 | 38.5 | 17.5 | 13.5 | 13.5 | 36.5 |
| Pregelatinized Starch | 5 | 5 | 5 | 5 | 5 | 5 |
| Salt | 1 | 1 | 1 | 1 | 1 | 1 |
| Beef (flavour) | 4 | 4 | | 4 | 4 | 4 |
| Propylene Glycol | 9 | 9 | 9 | 9 | 17 | 9 |
| Glycerogelatin (10%) | 8 | 8 | 8 | | 8 | 8 |
| Shortening Fat | 8 | 8 | 8 | 8 | | 8 |
| Ascorbyl palmitate | 0.2 | 0.2 | 0.2 | 0.2 | 0.2 | 0.2 |
| a-tocopherol | 0.1 | 0.1 | 0.1 | 0.1 | 0.1 | 0.1 |
| Glycerine | | | | 8 | | |
| Total | 100 | 100 | 100 | 100 | 100 | 100 |

1.1 Storage Conditions

All the formulations were stored for 1 month at 50° C. and for 6 months at 40° C.

2. Results

2.1 Appearance

At each time interval, the colour of the carprofen chewable treats had substantially darkened. Closer inspection revealed that this was due to darkening (or perhaps "toasting") of nutrisoy-grits at elevated temperatures. Some darkening could also have been due to the beef flavouring.

2.2 Carprofen Content

The results of carprofen assay during the compatibility study are listed in Table 11. These results clearly show that formulation CAR-2 (no nutrisoy grits) is the most stable formulation. The formulation CAR-5 (no shortening fat) was found to be relatively more stable than the other formulations for the first three months, after which a decrease in its stability was observed. Degradation of carprofen was, thus, attributed to nutrisoy grits, and to a lesser extent to shortening fat.

TABLE 11

Percentage of carprofen recovered from chewable treats after 6 months at 40° C.

| Sample Name | Carprofen (% initial) | | | | % Difference |
|---|---|---|---|---|---|
| | 0 Month | 1 Month | 3 Months | 6 Months | 0-6 Months |
| CAR-1 | 100.00 | 98.75 | 95.81 | 97.15 | 2.85% |
| CAR-2 | 100.00 | 98.64 | 98.14 | 98.86 | 1.14% |
| CAR-3 | 100.00 | 96.62 | 96.89 | 95.97 | 4.03% |
| CAR-4 | 100.00 | 96.68 | 95.93 | 95.38 | 4.62% |
| CAR-5 | 100.00 | 97.87 | 97.94 | 95.42 | 4.58% |
| CAR-6 | 100.00 | 96.43 | 96.63 | 95.89 | 4.11% |

2.3 pH

The greatest pH drop was observed in CAR-2 (no nutrisoy grits), which was also the most stable formulation in terms of carprofen recovery. Interestingly, a sample of CAR-2 stored at room temperature for three months did not show any pH drop indicating that the pH decreased only at elevated temperature. A slight decrease in pH was observed in all other formulations, except CAR-5 (no shortening Fat) as shown in Table 12.

TABLE 12 pH of carprofen chewable treats after 6 months at 40° C.

| Sample Name | pH | | | | % Difference |
|---|---|---|---|---|---|
| | 0 Month | 1 Month | 3 Months | 6 Months | 0-6 Months |
| CAR-1 | 5.76 | 5.66 | 5.63 | 5.72 | −0.75 |
| CAR-2 | 4.96 | 4.29 | 4.36 | 4.32 | −12.83 |
| CAR-3 | 6.03 | 5.88 | 5.75 | 5.53 | −8.29 |
| CAR-4 | 5.68 | 5.67 | 5.66 | 5.54 | −2.38 |
| CAR-5 | 5.63 | 5.72 | 5.69 | 5.70 | 1.30 |
| CAR-6 | 5.73 | 5.61 | 5.58 | 5.61 | −2.09 |

2.4 Moisture Content

The moisture content of all the formulations had increased after storage for six months at 40° C. The greatest increase was observed in the moisture content of CAR-4 (no gelatin) and CAR-5 (no shortening fat), indicating that gelatin and shortening limit moisture absorption into the chewable treats. The least increase in moisture content was observed in case of MLX-2 (no nutrisoy grits) and MLX-3 (beef flavour), indicating that nutrisoy grits and beef flavour tend to absorb atmospheric moisture.

TABLE 13

Moisture content (% w/w) of carprofen chewable treats after storage for 6 month at 40° C.

| Sample Name | Moisture content (% w/w) | | | % Difference |
|---|---|---|---|---|
| | 0 Month | 3 Months | 6 Months | (0-6 Months) |
| MLX-1 | 4.97 | 5.36 | 5.62 | 13.03 |
| MLX-2 | 5.22 | 5.33 | 5.47 | 4.69 |
| MLX-3 | 5.24 | 5.65 | 5.54 | 5.72 |
| MLX-4 | 4.58 | 5.36 | 5.62 | 22.70 |
| MLX-5 | 4.96 | 6.20 | 6.16 | 24.03 |
| MLX-6 | 5.89 | 6.51 | NT* | — |

NT*-Not tested due to insufficient sample

Example 4

Carprofen And Meloxicam Containing Chewable Treat

1. Experimental Design

Chewable treats containing carprofen (3.2% w/w) and Meloxicam (0.073% w/w) were studied to examine the stability of the treat over a period of six months.

Three formulation batches of chewable treats were prepared.

F1: Carprofen chewable treats containing 5% beef type flavour

F2: Carprofen chewable treats containing 10% beef type flavour

F3: Meloxicam chewable treats containing 10% beef type flavour.

TABLE 14

Formulation of F1-3

| No. | Ingredient | Function | Formulae (% w/w) | | |
|---|---|---|---|---|---|
| | | | F01 | F02 | F03 |
| 1 | Carprofen | API | 3.2 | 3.2 | — |
| 2 | Meloxicam | API | — | — | 0.073 |
| 3 | Ascorbyl Palmitate | Antioxidant | 0.2 | 0.2 | 0.2 |
| 4 | Decanox (tocopherol) | Antioxidant | 0.1 | 0.1 | — |
| 5 | Arbocel M80 (cellulose powder) | Diluent | 14.5 | 15 | 15 |
| 6 | Avicel DG (microcrystalline cellulose 75% w/w and dibasic calcium phosphate 25% w/w) | Binder | 5 | 5 | 6.227 |
| 8 | Methocel A15 Premium (methylcellulose) | Binder | 7 | 7 | 7 |
| 9 | Beef Type Flavour | Flavour | 5 | 10 | 10 |
| 10 | Icing Sugar | Sweetener | 20 | 19 | 20 |
| 11 | Sodium chloride | Humectant | — | 2 | 2 |
| 12 | Precirol ATO5 (glyceryl distearate) | Lubricant | 8 | 7.5 | 7.5 |
| 13 | Glycerine (vegetable) | Humectant | 16 | 11 | 11 |
| 14 | Propylene Glycol | Humectant | 11 | 12.5 | 12 |
| 15 | Pregelatinized maize starch | Disintegrant | 10 | 7.5 | 0 |
| | Total | | 100 | 100 | 100 |

The formulations were manufactured by the following method.

Carprofen or Meloxicam, Ascorbyl palmitate, Decanox, Arbocel M80, Avicel DG, Methocel A15 Premium, Beef Type Flavour, Icing Sugar, Sodium Chloride and Precirol ATO5 were blended together by dry blending in a planetary mixer.

After dry blending was complete, Glycerine and Propylene Glycol were added to the dry powder blend and the resultant mixture mixed in a planetary mixer until there are no lumps.

Pregelatinized Maize Starch was then added and the resultant mixture further blended.

The resultant mixture was then added to a Single Screw Extruder and extruded at about 46 rpm.

The amount of F1 and F2 manufactured was 500 g. The amount of F3 manufactured was 700 g.

1. Chemical Stability 1.1 F1 (Carprofen Chewable Treats Containing 5% Flavour)

F1 was stored in blister packs and foil packs at 40° C. and RT, respectively. The results of six month stability studies are summarized in Table 15.

TABLE 15

Carprofen content in F1 over 6 months.

| Storage Condition | % w/w Carprofen (% initial) | | | | |
|---|---|---|---|---|---|
| | 0 months | 1 month | 2 month | 3 month | 6 month |
| Room Temp (foil pack) | 3.10 (100.0%) | 3.05 (98.4%) | 3.16 (101.8%) | 3.07 (99.0%) | 3.05 (98.2%) |
| 40° C. (foil pack) | 3.10 (100.0%) | 3.11 (100.4%) | 3.15 (101.7%) | 3.03 (97.8%) | 3.07 (98.8%) |
| Room Temp (blister pack) | 3.10 (100.0%) | NT | NT | 3.064 (98.8%) | 3.06 (98.7%) |
| 40° C. (Blister pack) | 3.10 (100.0%) | NT | NT | 3.12 (100.5%) | 2.92 (94.1%) |

NT: Not Tested

As shown in Table 15 at 6 months there was very little degradation of carprofen in each of the foil packs and in the blister pack at RT. The percentage of carprofen reduced by 5.9% in the blister pack stored at 40° C.

1.2 F2 (Carprofen Chews Containing 10% Flavour)

F2 was stored in foil packs at 50° C., 40° C. and RT. The results of six month stability studies are summarized in Table 16.

TABLE 16

Carprofen content in F2 over 6 months.

| Storage Condition | % w/w Carprofen (% initial) | | | | |
|---|---|---|---|---|---|
| | 0 months | 1 month | 2 month | 3 month | 6 month |
| Room Temp (foil pack) | 3.15 (100.0%) | 3.08 (97.8%) | 3.15 (100.0%) | 3.04 (96.6%) | 3.03 (96.2%) |
| 40° C. (foil pack) | 3.15 (100.0%) | 3.05 (96.7%) | 3.14 (99.8%) | 3.01 (95.4%) | 3.05 (96.6%) |
| 50° C. (foil pack) | 3.15 (100.0%) | 3.05 (96.7%) | 3.14 (99.6%) | 2.96 (93.8%) | NT |

NT: Not Tested 1.3 F3 (Meloxicam Chews Containing 10% Flavour)

F3 was stored in foil packs at 50° C., 40° C. and RT, respectively. The results of 6-month stability studies are summarized in Table 17.

TABLE 17

Meloxicam content in F3 over 6 months.

| Storage Condition | % w/w Meloxicam (% initial) | | | | |
|---|---|---|---|---|---|
| | 0 months | 1 month | 2 month | 3 month | 6 month |
| Room Temp (foil pack) | 0.0690 (100.0%) | 0.0686 (99.4%) | 0.0683 (99.0) | 0.0677 (98.1%) | 0.0671 (97.2%) |
| 40° C. (foil pack) | 0.0690 (100.0%) | 0.0685 (99.3%) | 0.0669 (97.0%) | 0.0664 (96.2%) | 0.0669 (97.0%) |
| 50° C. (foil pack) | 0.0690 (100.0%) | 0.0666 (96.5%) | 0.0675 (97.8%) | 0.0654 (94.8%) | NT |

NT: Not Tested

2. Physical Stability 2.1 Appearance

Significant darkening of F1-3 chews was observed at 40° C. and 50° C., with the dark colour being more intense at the surface of the chew and in the interior. No significant colour change was observed in F1-3 chews stored at room temperature.

2.2 Moisture Content

Moisture content of the chews was analysed by Karl Fisher Titration method. Small changes in the moisture content (% w/w) of F1-3 were observed during six month storage as summarized in Table 18.

TABLE 18

Moisture content of F1-3 over 6 months.

| Sample Name | Package | Moisture content (% w/w) | | | | |
|---|---|---|---|---|---|---|
| | | 0 months | 1 months | 2 months | 3 months | 6 months |
| F1-RT | Foil pack | 8.2 | 4.1 | 4.7 | 5.9 | 6.5 |
| F1-40° C. | Foil pack | 8.2 | 4.7 | 4.6 | 5.0 | 5.5 |
| F1-RT | Blister pack | 8.2 | NT | NT | 8.1 | 6.1 |
| F1-40° C. | Blister pack | 8.2 | NT | NT | 5.6 | 8.7 |
| F2-RT | Foil pack | 3.5 | 5.3 | 4.2 | 4.9 | 6.6 |
| F2-40° C. | Foil pack | 3.5 | 4.8 | 4.7 | 6.3 | 4.8 |
| F2-50° C. | Foil pack | 3.5 | 3.2 | 5.0 | 5.1 | NT |
| F3-RT | Foil pack | 5.5 | 6.7 | 5.1 | 5.0 | 4.5 |
| F3-40° C. | Foil pack | 5.5 | 5.4 | 5.3 | 4.7 | 4.8 |
| F3-50° C. | Foil pack | 5.5 | 5.9 | 5.9 | 5.0 | NT |

NT: Not Tested

It is thought that the high initial moisture content of F1 could be due to time lag (12 days) between pulverization and analysis of the chews (which was avoided hereafter).

2.3 pH

Minimal changes in pH of F1-3 were observed during six month storage as summarized in Table 19.

TABLE 19 pH of F1-3 over 6 months.

| Sample Name | Package | pH | | | | |
|---|---|---|---|---|---|---|
| | | 0 months | 1 months | 2 months | 3 months | 6 months |
| F1-RT | Foil pack | 5.1 | 5.1 | 5.2 | 5.3 | 5.3 |
| F1-40° C. | Foil pack | 5.1 | 4.9 | 5.0 | 5.0 | 4.8 |
| F1-RT | Blister pack | 5.1 | NT | NT | 5.2 | 5.3 |
| F1-40° C. | Blister pack | 5.1 | NT | NT | 5.0 | 4.8 |
| F2-RT | Foil pack | 5.0 | 5.0 | 5.0 | 5.0 | 4.9 |
| F2-40° C. | Foil pack | 5.0 | 4.9 | 4.9 | 4.8 | 4.9 |
| F2-50° C. | Foil pack | 5.0 | 4.9 | 4.9 | 4.9 | NT |
| F3-RT | Foil pack | 5.3 | 5.4 | 5.3 | 5.2 | 5.4 |
| F3-40° C. | Foil pack | 5.3 | 5.3 | 5.3 | 5.1 | 5.4 |
| F3-50° C. | Foil pack | 5.3 | 5.2 | 5.3 | 5.2 | NT |

2.4 Microbiological Stability

Microbiological evaluation was done for F1 after six months at room temperature and for F2 after six months at room temperature and 40° C., respectively. The results of microbiological assay are summarized in Table 20.

TABLE 20

Microbiological testing in F1 and F2.

| Sample Name | Stability Time point | Package | Microbilogical Testing | | |
|---|---|---|---|---|---|
| | | | TAMC | TYMC | Pathogens* |
| F1-RT | 6 months | Foil pack | <10 cfu/g | <10 cfu/g | None detected |
| F2-40° C. | 6 months | Foil pack | <10 cfu/g | <10 cfu/g | None detected |
| F2-RT | 6 months | Blister pack | <10 cfu/g | <10 cfu/g | None detected |

* Pathogens tested: *E.coli, S.aurens, P.aeruginosa, Salmonella*

F1-3 are stable over the tested period.

Based on the stability trials, drug-excipient compatibility studies and extrusion trials, semi-soft chewable treats comprising carprofen and meloxicam were formulated as follows.

Water was not added to the chew formulation at any time during manufacture.

Guar gum was replaced with higher concentration of strong dry binding agents, Methocel (methylcellulose) and Avicel (75% microcrystalline cellulose+25% dibasic calcium phosphate), to improve rigidity and strength of the chews.

The amount of Nutrisoy grits was decreased or Nutrisoy was absent.

Povidones were removed due to trace peroxide impurities in them. They were substituted with other disintegrants, such as pregelatinized maize starch, croscarmellose sodium and sodium starch glycollate.

Ascorbyl palmitate was used as antioxidant, since this was a powder better distribution in the powder blend was expected. Tocopherols were used for synergistic effect with Ascorbyl palmitate.

Shortening fat was replaced with other fats/lipids that melt between 40-90° C. Glyceryl distearate NF/glycerol distearate (Type I) EP, having a melting point between 50-60° C. was used in a formulation. Several other fats, such as glycerol monostearate (melting point: 54-64° C.), behenoyl polyoxyl-8-glycerides NF (drop point: 60-74° C.), hydrogenated coconut oil or hard fat (melting point: 42-44° C.) were also tried.

Dextrose sugar replaced with a non-reducing sugar (sucrose) to avoid their Maillard reaction.

The chews manufactured in this manner had the following benefits.

Rigid, but chewy. Do not get deformed easily, 0% or very low friability

Do not harden or become brittle over time.

Easy to manufacture.

Good chemical stability of active ingredients.

No microbial contamination.

Dissolution rapid compared to other products in market (Drontal, Heartgard).

Example 5

Six Months Preliminary Stability Report for Meloxicam

This example describes a six month stability trial for three batches of meloxicam-containing dog chewable treats.

2.5 Experimental Design

Three small-scale batches, 1.5 kg each, of meloxicam-containing dog chewable treats were manufactured.

Each of the three batches represents a different formulation. All the chews from each batch were packed in heat-sealed aluminium foil bags and stored at three stability conditions for 12 months.

2.6 Formulation Details

Three batches, B1, B2 and B3, of meloxicam-containing dog chewable treats were prepared. Formulation details of each batch are shown in Table 21. All quantities are shown in % w/w.

TABLE 21

Formulation details for three batches of Meloxicam Dog Chewable Treat.

| Batch Number | B1 | B2 | B3 |
|---|---|---|---|
| Meloxicam | 0.073 | 0.073 | |
| Meloxicam-PEG6000(1:3) Granules | | | 0.292 |
| Guar Gum | 0.25 | 0.25 | 0.25 |
| Beef Flavour | 3.00 | 3.00 | 3.00 |
| Salt | 2.00 | 2.00 | 2.00 |
| Polyplasdone XL (crospovidone) | 5.00 | 5.00 | 5.00 |
| Arbocel M80 (cellulose powder) | 7.00 | 7.00 | 7.00 |
| NutrisoyGrits 40/20 | 25.00 | 25.00 | 25.00 |
| DextroseMonohydrate USP (QS) | 18.18 | 24.58 | 24.36 |
| Water | 10.00 | | |
| Glycerol | 13.00 | 13.00 | 13.00 |
| Propylene Glycol | 6.40 | 10.00 | 10.00 |
| Decanox (tocopherol) | 0.10 | 0.10 | 0.10 |
| Shortening fat | 10.00 | 10.00 | 10.00 |
| Total | 100.00 | 100.00 | 100.00 |

2.7 Storage Conditions and Tests

Stability samples were tested against the stability specification AR-STS-0014, Issue-1. The storage conditions and time points for stability tests are represented in Table 22.

TABLE 22

Storage conditions and time points for the preliminary stability test for Meloxicam Dog Chewable Treats.

| Storage conditions | Test intervals (months) | | | | | | | |
|---|---|---|---|---|---|---|---|---|
| | 0 | 1 | 2 | 3 | 6 | 9 | 12 | Spares |
| Room temperature | A | X* | X* | X* | X* | X | X | X |
| 30° C./65% RH | | X* | X* | X* | X | X | X | X |
| 40° C./65% RH | | X | X | X | X | X | X | X |

A Initial testing (T = 0): Full testing as per AR-STS-0014 (23 chews required).
X* Physical testing only as per AR-STS-0014: pH, moisture, disintegration and appearance (5 chews required).
X Full testing as per AR-STS-0014 except uniformity of content is not required (13 chews required).

Spares are placed at room conditions, 30° C./65% RH and 40° C./75% RH.

3. Results

The summary of test results are shown in Table 23 below.

TABLE 23

Summary of test results

| BN. | Time Point | Condition | MLX Content Average % | RRD % | RSD % | Water % | pH | Disintegration (min) |
|---|---|---|---|---|---|---|---|---|
| 052130 Original formulation | 0M | RT | 0.0729 | 1.64 | 0.79 | 14.34 | 6.2 | 50.4 |
| | 1M | RT | | | | 14.14 | 6.1 | 52.5 |
| | | 30° C. | | | | 14.44 | 5.8 | 65.4 |
| | | 40° C. | 0.0722 | 0.56 | 1.18 | 14.17 | 5.6 | 68.6 |
| | 2M | RT | | | | 14.69 | 6.1 | 64.2 |
| | | 30° C. | | | | 13.76 | 5.5 | 106.3 |
| | | 40° C. | 0.0701 | 2.70 | 1.14 | 15.68 | 5.4 | 128.6 |
| | 3M | RT | | | | 14.24 | 6.0 | 56.4 |
| | | 30° C. | | | | 15.29 | 6.6 | 122.3 |
| | | 40° C. | 0.0670 | 2.23 | 0.94 | 15.79 | 5.2 | 132.2 |
| | 6M | RT | | | | 14.06 | 5.9 | 79.5 |
| | | 30° C. | 0.0644 | −0.15 | 0.76 | 14.80 | 5.8 | 249.7 |
| | | 40° C. | 0.0639 | −1.56 | 0.98 | 15.37 | 5.8 | 360+ |

TABLE 23-continued

Summary of test results

| BN. | Time Point | Condition | MLX Content Average % | RRD % | RSD % | Water % | pH | Disintegration (min) |
|---|---|---|---|---|---|---|---|---|
| 052131 | 0M | RT | 0.0721 | 0.69 | 0.31 | 6.03 | 6.0 | 61.5 |
| No | 1M | RT | | | | 6.91 | 6.1 | 44.3 |
| water | | 30° C. | | | | 7.44 | 5.7 | 46.3 |
| adding | | 40° C. | 0.0693 | 0.43 | 0.22 | 6.94 | 5.5 | 44.5 |
| | 2M | RT | | | | 7.00 | 6.1 | 56.2 |
| | | 30° C. | | | | 7.10 | 5.6 | 50.3 |
| | | 40° C. | 0.0668 | 3.15 | 1.30 | 8.46 | 5.6 | 44.4 |
| | 3M | RT | | | | 6.63 | 6.0 | 42.4 |
| | | 30° C. | | | | 7.95 | 5.5 | 37.4 |
| | | 40° C. | 0.0649 | 1.23 | 0.51 | 8.17 | 6.3 | 28.4 |
| | 6M | RT | | | | 7.36 | 5.0 | 42.3 |
| | | 30° C. | 0.0618 | 0.16 | 0.48 | 8.32 | 5.1 | 29.5 |
| | | 40° C. | 0.0579 | 0.69 | 0.36 | 8.86 | 5.1 | 36.5 |
| 0S2132 | 0M | RT | 0.0735 | 7.87 | 3.25 | 5.81 | 6.0 | 65.5 |
| MLX- | 1M | RT | | | | 7.29 | 6.1 | 50.4 |
| PEG | | 30° C. | | | | 7.09 | 5.7 | 48.4 |
| granules | | 40° C. | 0.0687 | 6.59 | 2.91 | 6.99 | 5.6 | 46.7 |
| No | 2M | RT | | | | 6.95 | 6.0 | 53.8 |
| water | | 30° C. | | | | 8.50 | 5.6 | 45.5 |
| adding | | 40° C. | 0.0687 | 7.53 | 3.44 | 8.56 | 5.5 | 41.7 |
| | 3M | RT | | | | 7.19 | 6.0 | 38.3 |
| | | 30° C. | | | | 6.07 | 5.5 | 30.4 |
| | | 40° C. | 0.0684 | 4.49 | 2.15 | 6.01 | 5.3 | 27.7 |
| | 6M | RT | | | | 6.94 | 4.9 | 44.7 |
| | | 30° C. | 0.0635 | 2.69 | 1.22 | 8.44 | 5.0 | 34.9 |
| | | 40° C. | 0.0611 | 4.67 | 2.64 | 8.83 | 5.0 | 35.6 |

3.1 Organoleptic Properties

There was a significant change in the colour and appearance of the meloxicam-containing dog chewable treats. The colour of the chews grew darker with time and temperature. There was no change in the odour at any storage condition.

3.2 pH

There was a significant decrease in the pH of the meloxicam-containing dog chewable treats over a period of 6 months. The difference in pH was greater for B2 and B3 than for B1.

3.3 Disintegration Time

There was significant change in the disintegration time of all three batches. Disintegration time for B1 increased with temperature, whereas, the disintegration time of B2 and B3 decreased after storage at higher temperature.

The disintegration time for B2 and B3 after storage at any temperature was less than the corresponding disintegration time for B1.

3.4% Moisture Content

There was an overall increase in the moisture content of all the three batches of dog chews. Maximum change was observed in samples stored at 40° C./75% RH. The difference in moisture content was found to be more in B2 and B3 as compared to B1.

3.5 Meloxicam Content

Meloxicam content was found to decrease linearly with time. After storage for six months at 30° C./65% RH and 40° C./75% RH it had dropped to less than the specification limit of 90% w/w.

3.6 Uniformity of Content

Uniformity of content of meloxicam in meloxicam-containing dog chewable treats was tested only at the time of release and was found to be within acceptable limits.

3.7 Physical Nature

The chewable treats had not dried out and retained their soft pliable nature.

The chewable treats are subjected to a hardness measurement that measures the deformability of the chewable treat. A measurement lower than that for chewable treats manufactured with water demonstrates that manufacture with the absence of free water (i.e. added water) allows the chewable treat to retain its deformability compared to a chewable treat manufactured with added water. Chewable treats manufacture with water become brittle which affects their dissolution rate and drug stability.

4. Conclusions

Meloxicam content dropped below 90% w/w for all three batches of meloxicam-containing dog chewable treats, when tested after six month storage at 30° C./65% RH and 40° C./75% RH. This may be due to the presence of NutriSoyGrits 40/20, which Example 2 suggests has a detrimental effect on the stability of meloxicam. The presence of water in formulation B1 may also have a detrimental effect on the stability of meloxicam. Also, there was a significant change observed in appearance, disintegration time and moisture content of all three batches, at all storage conditions.

Example 6

Water Activity

The water activity of two chewable formulations was tested. One of the formulations was a placebo containing no pharmaceutically active agent and the other contained meloxicam. The method used was AOAC 978.18. The results are shown in Table 24 below.

TABLE 24

Water activity of chewable formulations.

| Formulation | Description | Water activity |
|---|---|---|
| F6 | 6 month old placebo chewable formulation | 0.335 |
| F3 | 23 month old meloxicam chewable formulation | 0.292 |

Both formulations had low water activity.

Details of the ingredients of F3 and F6 are provided in Table 25 below. All quantities are shown in % w/w.

TABLE 25

Ingredients of F3 and F6.

| Ingredient | F3 | F6 |
|---|---|---|
| Meloxicam | 0.073 | — |
| Ascorbyl Palmitate | 0.2 | 0.2 |
| Cellulose Powder | 15 | 13 |
| Avicel DG (Microcrystalline Cellulose 75% w/w and Dibasic Calcium Carbonate 25% w/w) | 6.127 | 6.5 |
| Methylcellulose | 7 | 7 |
| Beef type flavour | 10 | — |
| Vanilla flavour | — | 1 |
| Caramel colour | — | 0.3 |
| Confectioner's Sugar | 20 | 20 |
| Sodium chloride | 2 | — |
| Glyceryl Distearate | 7.5 | 8 |
| Glycerine (vegetable) | 11 | 14 |

TABLE 25-continued

Ingredients of F3 and F6.

| Ingredient | F3 | F6 |
|---|---|---|
| Propylene Glycol | 12 | 15 |
| Pregelatinized starch | 9 | 10 |
| Croscarmellose sodium | — | 5 |
| Total | 100.00 | 100.00 |

At the date of testing F3 was 23 months old and F6 was 6 months old. The data shows that a low water activity can be maintained in the chewable formulations over an extended period of time.

Example 7

Texture Profile Analysis

The texture profile of five chewable formulations (F1, F3, F7, F8, and F9) was analysed.

1. Formulations

The formulations were in the form of cylindrical extrudates having a diameter of 15 mm and a height between 14 and 16 mm.

Details of each the ingredients of each formulation are provided below in Table 26.

F1, F3, and F9 contained carprofen, meloxicam and metoclopramide, respectively. F7 and F8 were were placebos containing no pharmaceutically active agent. At the date of testing, F1 was 24 months old, F3 was 23 months old, F7 and F8 were 6 months old and F9 was 2 months old.

TABLE 26

Ingredients of formulations.

| Ingredient | F1 | F3 | F7 | F8 | F9 |
|---|---|---|---|---|---|
| Meloxicam | — | 0.073 | — | — | — |
| Carprofen | 3.2 | — | — | — | — |
| Metoclopramide | — | — | — | — | 0.3 |
| Ascorbyl Palmitate | 0.2 | 0.2 | 0.2 | 0.2 | 0.2 |
| Tocopherols | 0.1 | — | — | — | — |
| Arobcel M80 (Cellulose Powder) | 14.5 | 15 | 13 | 12.8 | 12.5 |
| Avicel DG (Microcrystalline Cellulose 75% w/w and Dibasic Calcium Carbonate 25% w/w) | 5 | 6127 | 6.5 | 5 | 5 |
| Methylcellulose | 7 | 7 | 7 | 7 | 7 |
| Artifical beef flavour | 5 | 10 | — | — | 5 |
| Butter caramel flavour | — | — | 1 | — | — |
| Roast pork flavour | — | — | — | 5 | — |
| Chicken fat concentrate | — | — | — | 0.5 | — |
| Stewed beef flavour | — | — | — | — | 0.5 |
| Caramel colour | — | — | 0.3 | — | — |
| Confectioner's Sugar | 20 | 20 | 20 | 20 | 20 |
| Sodium chloride | — | 2 | — | — | — |
| Glyceryl Distearate | 8 | 7.5 | 8 | 8 | 8 |
| Glycerine (vegetable) | 16 | 11 | 14 | 13 | 13 |
| Propylene Glycol | 11 | 12 | 15 | 13.5 | 13.5 |
| Pregelatinized starch | 10 | 9 | 10 | 10 | 10 |
| Croscarmellose sodium | — | — | 5 | 5 | 5 |
| Total | 100.00 | 100.00 | 100.00 | 100.00 | 100.00 |

2. Texture Profile Analysis

Texture profile analysis is a texture measurement that simulates two 'bites' by compressing a food sample twice between a base and a plate at constant speed and measuring the force versus time. The test is widely used in food research.

2.1 Test Procedure

A single cylindrical extrudate having a diameter of 15 mm and a height between 14 and 16 mm of each formulation was tested using an Instron 4444 texture analyser instrument. A double 9 mm compression was carried out on each tablet with a 65 mm diameter aluminium plate, at a crosshead speed of 100 mm/min. All tests were carried out at room temperature (25±1° C.).

2.2 Results

The results of the texture profile analysis are shown below in Tables 27 and 28.

TABLE 27

Compression.

| Formulation | Height (mm) | Compression Target (mm) | Actual Compression * (mm) | Compression (%) |
|---|---|---|---|---|
| F1 | 15.1 | 9 | 8.8 | 58 |
| F3 | 15.7 | 9 | 8.7 | 56 |
| F7 | 14.8 | 9 | 8.6 | 58 |
| F8 | 14.0 | 9 | 8.2 | 58 |
| F9 | 16.1 | 9 | 8.8 | 55 |

* Actual compression is dependent on the shape of the sample tested.

A comparable degree of compression was achieved with all tablets tested.

TABLE 27

Texture profile analysis.

| Formulation | Hardness (N) | Compression Energy % (N · mm) | Adhesion (N · mm) | Cohesion | Springiness (%) | Chewiness (N) | Modulus (N/mm) |
|---|---|---|---|---|---|---|---|
| F1 | 180 | 897 | −2.94 | 0.082 | 15 | 2.26 | 34.9 |
| F3 | 267 | 1432 | −6.14 | 0.081 | 18 | 3.90 | 53.2 |
| F7 | 162 | 740 | −0.49 | 0.088 | 19 | 2.78 | 28.9 |
| F8 | 231 | 912 | −2.55 | 0.089 | 19 | 3.93 | 34.4 |
| F9 | 154 | 819 | −2.61 | 0.086 | 19 | 2.57 | 31.4 |

The results are generally similar for all of the formulations tested. This suggests that texture of the formulation does not change significantly on storage.

Notably, all of the samples tested yielded, rather than fractured in the first bite.

Figure 2:
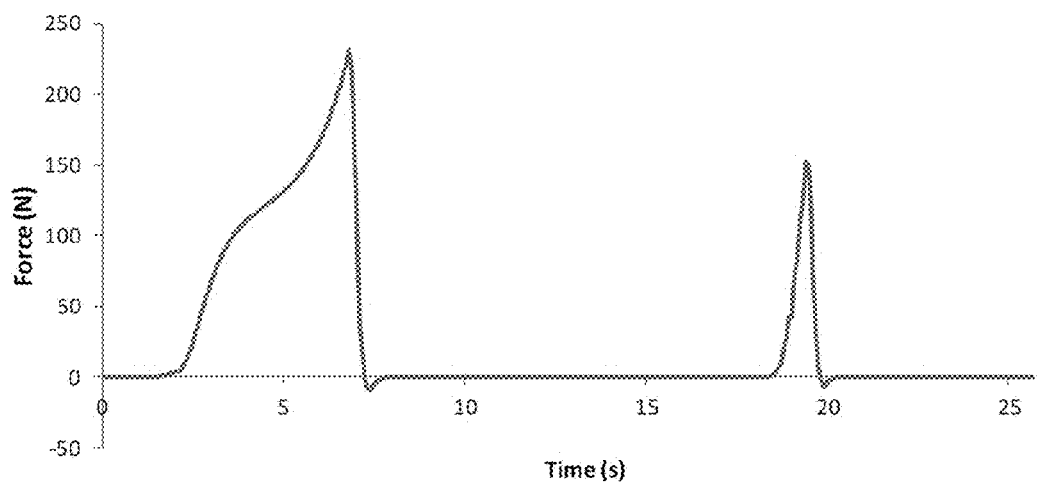
FIG. 2 shows a double compression curve for a placebo chewable formulation. The curve is a plot of force (N) applied to a cylindrical extrudate of the chewable formulation over time.

A double compression curve for F8 is shown in FIG. 2. The curve is typical for the formulations tested.

A description of the properties of the formulations in Table 27 above and how the properties were evaluated is provided in Table 28 below.

TABLE 28

Description of properties evaluated.

| Property | Definition or calculation |
|---|---|
| Fracture (N) | The first peak in the force curve. Also called brittleness. Not observed in any of the samples tested. |
| Hardness (N) | The force at maximum compression. |
| Compression energy (N.mm) | Area under the force-deformation curve for the first bite. |
| Adhesion (N.mm) | Area under the extension curve for the first bite. When the probe reverses the sample may stick and a negative force is recorded up until the sample releases. |
| Cohesiveness (–) | Compression energy of the second bite divided by the compression energy of the first bite. |
| Springiness (–) | Ratio of the duration of contact with the sample during the second compression to that during the first compression. Springiness is a measure of the extent to which the sample recovers from the first compression. A value of 1 means total recovery, a value of 0 means no recovery (sample does not bounce back from the compression). |
| Chewiness (N) | Product of hardness, cohesiveness and springiness. |
| Modulus (N/mm) | Initial slope of the force-deformation curve. Calculated by dividing the force at 3 mm compression by 3 mm. |

Example 8

Ingredients Of Chewable Formulations

Chewable formulations having the ingredients shown in Table 29 were prepared. All of the quantities are shown in % w/w.

TABLE 29

Ingredients of chewable formulations.

| Ingredient | Classification | Function | Content |
|---|---|---|---|
| API | Various | Therapeutic | 0.073-16.0% |
|  |  | Total API | 0.073-16.0% |
| Ascorbyl Palmitate | Fatty acid ester | Antioxidant/stabilizer | 0.20% |
| BHT | Phenolic | Antioxidant/stabilizer |  |
| Tocopherol | Vit E | Antioxidant/stabilizer | 0.10% |
| Buffers | Various | Stabilizer |  |
|  |  | Total antioxidant/stabilizer | 0-0.3% |
| Croscarmellose sodium (Ac-Di-Sol) | Cellulosic biopolymer | Super-Disintegrant | 0-25% |
| Sodium Starch Glycollate (SSG) | Starch | Super-Disintegrant | 0-5% |
| Polyplasdone XL (crosspovidone) | Povidone | Super-Disintegrant | 0-5% |
| Pregelatinized starch | Starch | Disintegration aid | 0-10% |
|  |  | Total disintegrant | 0-25% |
| Nutrisoy Grits | Protein | Filler | 20-25% |
| Wheat Germ | Protein | Filler | 25% |
| Arbocel M80 (cellulose powder) | Cellulosic biopolymer | Filler | 0-15% |
| Lactose monohydrate | Disaccharide sugar | Filler | 0-48% |
|  |  | Total filler | q.s. |
| Avicel DG (microcrystalline cellulose 75% w/w and dibasic calcium phosphate 25% w/w) | Microcrystalline cellulose and dibasic calcium phosphate | Filler/binder | 0-10% |
| Methocel A15 Premium (methylcellulose) | Cellulose ether biopolymer | Filler/binder | 3-15% |
|  |  | Total binder | 0.25-25% |

TABLE 29-continued

Ingredients of chewable formulations.

| Ingredient | Classification | Function | Content |
|---|---|---|---|
| Flavour (solid) | Synthetic | Flavour/taste masker | 3-10% |
| Flavour (liq) | Synthetic | Flavour/taste masker | 0.5-2% |
| | | Total flavour | 0-10% |
| Icing Sugar | Sugar | Sweetener | 0-30% |
| Dextrose Monohydrate | Sugar | Sweetener | 10.15-28.18% |
| Compressible Sugar | Sugar | Sweetener | 0-39% |
| | | Total sugar | 10-64% |
| Precirol ATO5 (glyceryl stearate) | Glycerol stearate (mixed polymer) | Lubricant (fat/lipid) | 7-8% |
| Shortening Fat | Lipid/fat | Lubricant (fat/lipid) | 10% |
| | | Total lubricant | 7-10% |
| Glycerine (vegetable) | Glycerol | Plasticizer/humectant | 0-36%% |
| Propylene Glycol | Glycol | Plasticizer/humectant | 0-31%% |
| | | Total plasticizer/humectant | 16-36% |
| PEG-6000 | | Protective coating | 0.219-20% |
| Stearic Acid | | Protective coating | 0.657% |
| | | Total coating | 0.219-20% |
| | | Total | 100% |

The active ingredient (API) in Table 29 above was selected from those listed in Table 30 below. All of the quantities are shown in % w/w.

TABLE 30

APIs in chewable formulations.

| API | Classification | Aqueous solubility | Content |
|---|---|---|---|
| Carprofen | NSAID | Poor | 3.2 |
| Meloxicam | NSAID | Poor | 0.073 |
| Diphenhydramine | Antihistamine | Soluble | 0.83 |
| Metoclorpramide | Antiemetic | Soluble | 0.33-2 |
| Spinosad | Parasiticide | Soluble | 16 |

TABLE 30-continued

APIs in chewable formulations.

| API | Classification | Aqueous solubility | Content |
|---|---|---|---|
| Prednisolone | Corticosteroid | Poor | 1.33 |
| Milbemycin oxime | Parasiticide | Poor | 0.1-3% |
| Pyrantel | Parasiticide | Poor | 10.56% |
| Abamectin | Parasiticide | Poor | 0.0073% |
| Praziquantel | Parasiticide | Soluble | 3.67% |
| Oxibendazole | Parasiticide | Poor | 16.50% |

Details of 45 chewable formulations (some placebo) that were prepared are provided in Table 31 below.

TABLE 31

Formulations of the invention.

| Ingredients | | 1 | 2 | 3 | 4 |
|---|---|---|---|---|---|
| API | | Meloxicam (0.073%) | Placebo | Meloxicam (0.073%) | Placebo |
| Disintegrant | Ac-Di-Sol | | | | |
| | Pre-gel Starch | | | | |
| | Other | Polyplasdone XL (5%) | Polyplasdone XL (5%) | Polyplasdone XL (5%) | Polyplasdone XL (5%) |
| Filler/ Binder | Arbocel M80 | 7.00% | 7% | 7% | 4% |
| | Avicel DG | | | | |
| | Binder | Guar gum (0.25%) | Guar gum (0.25%) | Guar gum (0.25%) | Guar gum (0.25%) |
| | Other | Wheat germ (25%) | Nutrisoy Grits (25%) | Nutrisoy Grits (25%) | Nutrisoy Grits (20%) |
| Plasticizer/ Humectant | Glycerine | 13% | 13% | 13% | 13% |
| | Propylene Glycol | 6.40% | 10.00% | 10.00% | 10.00% |
| | Other | Salt (2%) | Salt (2%) | Salt (2%) | Salt (1.5%) |
| Flavour/ Sweeteners/ Colour | Flavor | Beef Powder (3%) | Beef Powder (3%) | Beef Powder (3%) | Beef Powder (3%) |
| | Sugar | Dextrose (28.18%) | Dextrose (24.65%) | Dextrose (24.58%) | Dextrose (13.15%) |
| | Colour | | | | |

TABLE 31-continued

Formulations of the invention.

| | | | | | |
|---|---|---|---|---|---|
| AntiOx/ Stabilizers | Ascorbyl Palmitate | Decanox (0.1%) | Decanox (0.1%) | Decanox (0.1%) | Decanox (0.1%) |
| | Other | | | | |
| Lubricant | | Shortening (10%) | Shortening (10%) | Shortening (10%) | Shortening (10%) PEG6000 (20%) |
| Total liquid | | 19.40% | 23.00% | 23.00% | 23.00% |

| Ingredients | | 5 | 6 | 7 | 8 |
|---|---|---|---|---|---|
| API | | Placebo | Meloxicam (0.073%) | Meloxicam (0.073%) | Meloxicam (0.073%) |
| Disintegrant | Ac-Di-Sol | | | | |
| | Pre-gel Starch | | | | |
| | Other | Polyplasdone XL (5%) | Polyplasdone XL (5%) | Polyplasdone XL (5%) | Polyplasdone XL (5%) |
| Filler/ Binder | Arbocel M80 | 4% | 7% | 7% | 7% |
| | Avicel DG | | | | |
| | Binder | Guar gum (0.25%) | Guar gum (0.25%) | Guar gum (0.25%) | Guar gum (0.25%) |
| | Other | Nutrisoy Grits (25%) | Nutrisoy Grits (25%) | Nutrisoy Grits (25%) | Nutrisoy Grits (25%) |
| Plasticizer/ Humectant | Glycerine | 13% | 13% | 13% | 13% |
| | Propylene Glycol | 8% | 10% | 10% | 10% |
| | Other | Salt (1.5%) | Salt (2%) | Salt (2%) | Salt (2%) |
| Flavour/ Sweeteners/ Colour | Flavor Sugar Colour | Beef Powder (3%) Dextrose (10.15%) | Beef Powder (3%) Dextrose (24.36%) | Beef Powder (3%) Dextrose (23.92%) | Beef Powder (3%) Dextrose (23.92%) |
| AntiOx/ Stabilizers | Ascorbyl Palmitate | Decanox (0.1%) | Decanox (0.1%) | Decanox (0.1%) | Decanox (0.1%) |
| | Other | | | | |
| Lubricant | | Shortening (10%) PEG6000 (20%) | Shortening (10%) PEG6000 (0.219%) | Shortening (10%) PEG6000 (0.657%) | Shortening (10%) Stearic acid (0.657%) |
| Total liquid | | 21.00% | 23.00% | 23.00% | 23.00% |

| Ingredients | | 9 | 10 | 11 | 12 |
|---|---|---|---|---|---|
| API | | Carprofen (3.2%) | Carprofen (3.2%) | Carprofen (3.2%) | Meloxicam (0.073%) |
| Disintegrant | Ac-Di-Sol | | | | |
| | Pre-gel Starch | 10% | 5% | 7.50% | 9% |
| | Other | | | | |
| Filler/ Binder | Arbocel M80 | 14.5 | 14.5 | 15% | 15% |
| | Avicel DG | 5% | 5% | 5% | 6.13% |
| | Binder | Methocel (7%) | Methocel (7%) | Methocel (7%) | Methocel (7%) |
| | Other | | | | |
| Plasticizer/ Humectant | Glycerine | 16% | 16% | 11% | 11% |
| | Propylene Glycol | 11% | 11% | 12.50% | 12% |
| | Other | | | Salt (2%) | Salt (2%) |
| Flavour/ Sweeteners/ Colour | Flavor Sugar Colour | Beef Powder (5%) ICS (20%) | Beef Powder (10%) ICS (20%) | Beef Powder (10%) ICS (19%) | Beef Powder (10%) ICS (20%) |
| AntiOx/ Stabilizers | Ascorbyl Palmitate | Ascorbyl palmitate(0.2%) | Ascorbyl palmitate(0.2%) | Ascorbyl palmitate(0.2%) | Ascorbyl palmitate(0.2%) |
| | Other | Decanox (0.1%) | Decanox (0.1%) | Decanox (0.1%) | Decanox (0.1%) |
| Lubricant | | Precirol AT05 (8%) | Precirol AT05 (8%) | Precirol AT05 (7.5%) | Precirol AT05 (7.5%) |
| Total liquid | | 27.00% | 27.00% | 23.50% | 23.00% |

| Ingredients | | 13 | 14 | 15 | 16 |
|---|---|---|---|---|---|
| API | | Carprofen (3.2%) | Carprofen (3.2%) | Placebo | Placebo |
| Disintegrant | Ac-Di-Sol | | 5% | 5% | 5% |
| | Pre-gel Starch | 6% | 5% | 10% | 10% |
| | Other | SSG(5%) | | | |
| Filler/ Binder | Arbocel M80 | 13% | 13% | 13% | 12.80% |
| | Avicel DG | 5% | 5% | 6% | 5% |
| | Binder | Methocel (7%) | Methocel (7%) | Methocel (7%) | Methocel (7%) |
| | Other | | | | |
| Plasticizer/ Humectant | Glycerine | 10% | 11% | 12% | 13% |
| | Propylene Glycol | 12% | 12% | 12% | 14% |
| | Other | Salt (2%) | Salt (2%) | Salt (2%) | |
| Flavour/ Sweeteners/ Colour | Flavor Sugar Colour | Beef Powder (10%) ICS (19%) | Beef Powder (10%) ICS (19%) | Beef liq (0.5%) lactose (23.8%) | Beef Powder (5%) ICS (20%) |
| AntiOx/ | Ascorbyl | Ascorbyl | Ascorbyl | Ascorbyl | Ascorbyl |

TABLE 31-continued

Formulations of the invention.

| | | | | | |
|---|---|---|---|---|---|
| Stabilizers | Palmitate | palmitate(0.2%) | palmitate(0.2%) | palmitate(0.2%) | palmitate(0.2%) |
| | Other | Decanox (0.1%) | Decanox (0.1%) | | |
| Lubricant | | Precirol AT05 (7.5%) | Precirol AT05 (7.5%) | Precirol AT05 (7.5%) | Precirol AT05 (8%) |
| Total liquid | | 22.00% | 23.00% | 24.00% | 27.00% |

| Ingredients | | 17 | 18 | 19 | 20 |
|---|---|---|---|---|---|
| API | | Placebo | Placebo | Placebo | Placebo |
| Disintegrant | Ac-Di-Sol | 5% | 5% | 5% | 5% |
| | Pre-gel Starch | 10% | 10% | 10% | 10% |
| | Other | | | | |
| Filler/ | Arbocel M80 | 12.80% | 13.80% | 13% | 13% |
| Binder | Avicel DG | 5% | 6% | 6.50% | 6.50% |
| | Binder | Methocel (7%) | Methocel (7%) | Methocel (7%) | Methocel (7%) |
| | Other | | | | |
| Plasticizer/ | Glycerine | 13% | 13% | 14% | 14% |
| Humectant | Propylene Glycol | 13.50% | 14% | 15% | 15% |
| | Other | | | | |
| Flavour/ | Flavor | Beef pdr + liq (5% + 0.5%) | Butter Caramel Liq (1%) | Butter Caramel Liq (1%) | Vanilla liq + Vanillin (1% + 0.4%) |
| Sweeteners/ | Sugar | ICS (20%) | ICS (21%) | ICS (20%) | ICS (20%) |
| Colour | Colour | | Caramel (2%) | Caramel (0.3%) | Caramel (0.3%) |
| AntiOx/ | Ascorbyl | Ascorbyl | Ascorbyl | Ascorbyl | Ascorbyl |
| Stabilizers | Palmitate | palmitate(0.2%) | palmitate(0.2%) | palmitate(0.2%) | palmitate(0.2%) |
| | Other | | | | |
| Lubricant | | Precirol AT05 (8%) | Precirol AT05 (8%) | Precirol AT05 (8%) | Precirol AT05 (8%) |
| Total liquid | | 26.50% | 27.00% | 29.00% | 29.00% |

| Ingredients | | 21 | 22 | 23 | 24 |
|---|---|---|---|---|---|
| API | | Placebo | Placebo | Placebo | Placebo |
| Disintegrant | Ac-Di-Sol | 5% | 5% | 5% | 5% |
| | Pre-gel Starch | 10% | 10% | 10% | 10% |
| | Other | | | | |
| Filler/ | Arbocel M80 | 12.80% | 12.80% | 12.80% | 12.80% |
| Binder | Avicel DG | 5% | 5% | 5% | 5% |
| | Binder | Methocel (7%) | Methocel (7%) | Methocel (7%) | Methocel (7%) |
| | Other | | | | |
| Plasticizer/ | Glycerine | 13% | 13% | 13% | 13% |
| Humectant | Propylene Glycol | 13.5% | 13.5% | 13.5% | 13.5% |
| | Other | | | | |
| Flavour/ | Flavor | Chicken pdr + Fish liq (5% + 0.5%) | Beef pdr + liq (5% + 0.5%) | Pork pdr + Chicken liq (5% + 0.5%) | Chicken pdr + Chicken liq (5% + 0.5%) |
| Sweeteners/ | Sugar | ICS (20%) | ICS (20%) | ICS (20%) | ICS (20%) |
| Colour | Colour | | | | |
| AntiOx/ | Ascorbyl | Ascorbyl | Ascorbyl | Ascorbyl | Ascorbyl |
| Stabilizers | Palmitate | palmitate(0.2%) | palmitate(0.2%) | palmitate(0.2%) | palmitate(0.2%) |
| | Other | | | | |
| Lubricant | | Precirol AT05 (8%) | Precirol AT05 (8%) | Precirol AT05 (8%) | Precirol AT05 (8%) |
| Total liquid | | 26.50% | 26.50% | 26.50% | 26.50% |

| Ingredients | | 25 | 26 | 27 | 28 |
|---|---|---|---|---|---|
| API | | Metoclorpramide (0.3%) | Spinosad (16%) | Defenhydramine (0.83%) | Prednisolone (1.3%) |
| Disintegrant | Ac-Di-Sol | 5% | 5% | 5% | 5% |
| | Pre-gel Starch | 10% | | 10% | 10% |
| | Other | | | | |
| Filler/ | Arbocel M80 | 12.50% | 6.80% | 9.97% | 10.70% |
| Binder | Avicel DG | 5% | 5% | 7% | 7% |
| | Binder | Methocel (7%) | Methocel (7%) | Methocel (7%) | Methocel (7%) |
| | Other | | | | |
| Plasticizer/ | Glycerine | 13% | 12.50% | 13% | 14% |
| Humectant | Propylene Glycol | 13.5% | 12% | 13.50% | 15% |
| | Other | | | | |
| Flavour/ | Flavor | Beef pdr + liq (5% + 0.5%) | Beef pdr + liq (5.5% + 2%) | Pork pdr + Chicken liq (5% + 0.5%) | Butter Caramel Liq (1%) |
| Sweeteners/ | Sugar | ICS (20%) | ICS (20%) | ICS (20%) | ICS (21%) |
| Colour | Colour | Caramel (0.3%) | | | |

TABLE 31-continued

Formulations of the invention.

| | | | | | |
|---|---|---|---|---|---|
| AntiOx/ Stabilizers | Ascorbyl Palmitate Other | Ascorbyl palmitate(0.2%) | Ascorbyl palmitate(0.2%) | Ascorbyl palmitate(0.2%) | Ascorbyl palmitate(0.2%) |
| Lubricant | | Precirol AT05 (8%) | Precirol AT05 (8%) | Precirol AT05 (8%) | Precirol AT05 (8%) |
| Total liquid | | 26.50% | 24.50% | 26.50% | 29.00% |
| Ingredients | | 29 | 30 | 31 | 32 |
| API | | Placebo | Metoclorpramide (2%) | Metoclorpramide (2%) | Metoclorpramide (2%) |
| Disintegrant | Ac-Di-Sol | 4% | 10% | 5% | 25% |
| | Pre-gel Starch Other | | | | |
| Filler/ | Arbocel M80 | 0.00% | 0.00% | 0.00% | 15.00% |
| Binder | Avicel DG | 0% | 2% | 4% | 2% |
| | Binder Other | Methocel (4%) | Methocel (3%) | Methocel (6%) | Methocel (3%) |
| Plasticizer/ | Glycerine | 9% | 10% | 10.00% | 20% |
| Humectant | Propylene Glycol Other | 13% | 6% | 6% | 6% |
| Flavour/ Sweeteners/ | Flavor | Compressible Sugar (39%) | Compressible Sugar (30%) | Compressible Sugar (30%) | Compressible Sugar (10%) |
| Colour | Sugar Colour | ICS (25%) | ICS (30%) | ICS (30%) | ICS (10%) |
| AntiOx/ Stabilizers | Ascorbyl Palmitate Other | | | | |
| Lubricant | | Precirol AT05 (6.5%) | Precirol AT05 (7%) | Precirol AT05 (7%) | Precirol AT05 (7%) |
| Total liquid | | 21.50% | 16.00% | 16.00% | 26.00% |
| Ingredients | | 33 | 34 | 35 | 36 |
| API | | Metoclorpramide (2%) | Metoclorpramide (2%) | Metoclorpramide (2%) | Carprofen (2%) |
| Disintegrant | Ac-Di-Sol Pre-gel Starch Other | 5% | 25% | 5% | 5% |
| Filler/ | Arbocel M80 | 15.00% | 2.00% | | |
| Binder | Avicel DG | 10% | 10% | 2% | 2% |
| | Binder Other | Methocel (15%) | Methocel (15%) | Methocel (3%) Lactose (48%) | Methocel (3%) Lactose (5%) |
| Plasticizer/ | Glycerine | 18% | 11% | 12.00% | 10% |
| Humectant | Propylene Glycol Other | 8% | 18% | 11% | 6% |
| Flavour/ Sweeteners/ | Flavor | Compressible Sugar (10%) | | | Compressible Sugar (30%) |
| Colour | Sugar Colour | ICS (10%) | ICS (10%) | ICS (10%) | ICS (30%) |
| AntiOx/ Stabilizers Other | Ascorbyl Palmitate | | | | |
| Lubricant | | Precirol AT05 (7%) | Precirol AT05 (7%) | Precirol AT05 (7%) | Precirol AT05 (7%) |
| Total liquid | | 26.00% | 29.00% | 23.00% | 16.00% |
| Ingredients | | 37 | 38 | 39 | 40 |
| API | | Carprofen (2%) | Carprofen (2%) | Carprofen (2%) | Carprofen (2%) |
| Disintegrant | Ac-Di-Sol Pre-gel Starch Other | 25% | 5% | 8% | 25% |
| Filler/ | Arbocel M80 | | | | |
| Binder | Avicel DG | 2% | 10% | 3% | 10% |
| | Binder Other | Methocel (3%) Lactose (33%) | Methocel (15%) Lactose (30%) | Methocel (4.5%) | Methocel (10%) |
| Plasticizer/ | Glycerine | 10% | 10% | 6% | 13% |
| Humectant | Propylene Glycol Other | 8% | 11% | 10% | 16% |
| Flavour/ Sweeteners/ | Flavor | | | Compressible Sugar (30%) | |

TABLE 31-continued

Formulations of the invention.

| | | | | | |
|---|---|---|---|---|---|
| Colour | Sugar Colour | ICS (10%) | ICS (10%) | ICS (30%) | ICS(10%) |
| AntiOx/ Stabilizers | Ascorbyl Palmitate Other | | | | |
| Lubricant | | Precirol AT05 (7%) | Precirol AT05 (7%) | Precirol AT05 (7%) | Precirol AT05 (7%) |
| Total liquid | | 18.00% | 21.00% | 16.00% | 29.00% |

| Ingredients | | 41 | 42 | 43 | 44 |
|---|---|---|---|---|---|
| API | | Carprofen (2%) | Carprofen (2%) | Carprofen (2%) | Carprofen (2%) |
| Disintegrant | Ac-Di-Sol | 25% | 25% | 25% | 25% |
| | Pre-gel Starch | | | | |
| | Other | | | | |
| Filler/ Binder | Arbocel M80 Avicel DG | 10% | 10% | 10% | 10% |
| | Binder | Methocel (10%) | Methocel (10%) | Methocel (10%) | Methocel (10%) |
| | Other | | | | |
| Plasticizer/ Humectant | Glycerine | 0% | 36% | 0% | 25% |
| | Propylene Glycol | 25% | 0% | 31% | 0% |
| | Other | | | | |
| Flavour/ Sweeteners/ Colour | Flavor Sugar | ICS(10%) | ICS(10%) | ICS(10%) | ICS(10%) |
| | Colour | | | | |
| AntiOx/ Stabilizers | Ascorbyl Palmitate Other | | | | |
| Lubricant | | Precirol AT05 (7%) | Precirol AT05 (7%) | Precirol AT05 (7%) | Precirol AT05 (7%) |
| Total liquid | | 25.00% | 36.00% | 31.00% | 25.00% |

| Ingredients | | 45 |
|---|---|---|
| API | | Carprofen (2%) |
| Disintegrant | Ac-Di-Sol | 25% |
| | Pre-gel Starch | |
| | Other | |
| Filler/ Binder | Arbocel M80 Avicel DG | 10% |
| | Binder | Methocel (10%) |
| | Other | |
| Plasticizer/ Humectant | Glycerine | 25% |
| | Propylene Glycol | 10% |
| | Other | |
| Flavour/ Sweeteners/ Colour | Flavor Sugar | ICS(10%) |
| | Colour | |
| AntiOx/ Stabilizers | Ascorbyl Palmitate Other | |
| Lubricant | | Precirol AT05 (7%) |
| Total liquid | | 35.00% |

Example 9

Dissolution of Formulations of the Invention

Eight chewable formulations were prepared and their dissolution tested. The procedure used was as described above in Example 1. The results are shown below in Table 32. All of the quantities are shown in % w/w.

TABLE 32

Dissolution of formulations of the invention.

| | API | DT (mins) | Dissolution of API at 15 mins |
|---|---|---|---|
| F#1 | Metoclorpramide | 22 | <75% |
| F#2 | Metoclorpramide | 30 | >75% |
| F#3 | Metoclorpramide | 12 | >75% |
| F#4 | Metoclorpramide | 15 | >75% |
| F#5 | Carprofen | 30 | <75% |

TABLE 32-continued

Dissolution of formulations of the invention.

| | API | DT (mins) | Dissolution of API at 15 mins |
|---|---|---|---|
| F#6 | Carprofen | 15 | <75% |
| F#7 | Carprofen | 18 | >75% |
| F#8 | Carprofen | 27 | >75% |

Details of the ingredients of formulations F#1-F#8 are shown below in Table 33. All of the quantities are shown in % w/w.

TABLE 33

Ingredients of formulations.

| Ingredient | F#1 | F#2 | F#3 | F#4 | F#5 | F#6 | F#7 | F#8 |
|---|---|---|---|---|---|---|---|---|
| Soluble API (Metoclorpramide) | 2% | 2% | 2% | 2% | — | — | — | — |
| Insoluble API (Carprofen) | — | — | — | — | 2% | 2% | 2% | 2% |
| Disintegrant (Ac-Di-Sol) | 10% | 5% | 25% | 5% | 5% | 25% | 5% | 7.5% |
| Binder (2:3) (Avicel DG:Methocel A15) | 5% | 10% | 25% | 5% | 5% | 5% | 25% | 7.5% |
| Sweetener (Icing Sugar) | 30% | 30% | 10% | 10% | 30% | 10% | 10% | 30% |
| Sweetener (Di-Pac Sugar) | 30% | 30% | — | — | 30% | — | — | 30% |
| Diluent (Arbocel M80/Lactose) | — | — | 2% | 48% | 5% | 33% | 30% | — |
| Precirol AT05 | 7% | 7% | 7% | 7% | 7% | 7% | 7% | 7% |
| Glycerine | 10% | 10% | 11% | 12% | 10% | 10% | 10% | 6% |
| Propylene Glycol | 6% | 6% | 18% | 11% | 6% | 8% | 11% | 10% |

Figure 3:
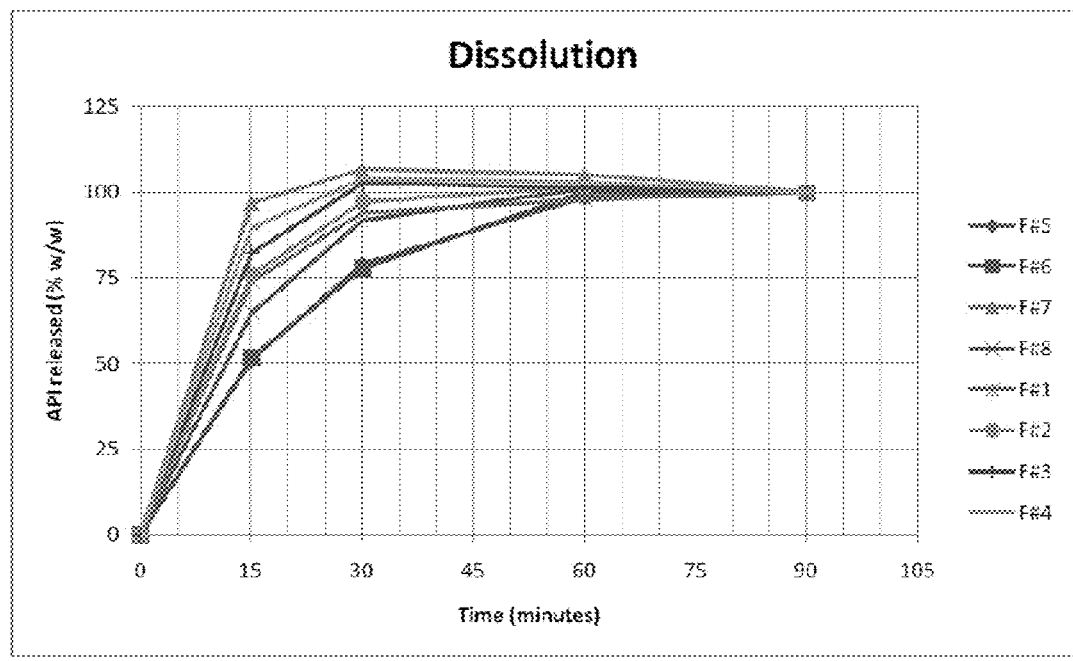
FIG. 3 shows the dissolution profiles of eight chewable formulations.

The dissolution profiles of the formulations over time are shown in FIG. 3. At 30 minutes, the dissolution of all of the formulations was >75%. At 90 minutes, the dissolution of all of the formulations was 100%.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

The invention claimed is:

1. A shelf stable chewable formulation, comprising:
a nutritional or pharmaceutically active agent; and
a plasticiser, and
wherein the formulation is formed by extrusion and wherein at least 95, 96, 97, 98, or 99% by weight of any water present in the chewable formulation is present in a bound state.

2. The chewable formulation according to claim 1, wherein the pharmaceutically active agent is selected from anesthetics, corticosteroids, NSAIDS, antibiotics, antiemetics, anti-thyroidal agents or anti-parasiticidal agents, or any combination of any two or more thereof.

3. The chewable formulation according to claim 1, wherein the chewable formulation further comprises a component selected from the group consisting of a filler, a diluent, a binder, a sweetener, a flavouring agent, a plasticizer, a humectant, a fat, a lipid, an antioxidant, a colouring agent, a disintegrating agent, a preservative, a buffering agent, and any combination thereof.

4. The chewable formulation according to claim 3, wherein when a filler is included, the filler comprises 2, 4, 6, 8, 10, 12, 14, 16, 18, 20, 22, 24, 26, 28, 30, 32, 34, 36, 38 or 40% by weight of the formulation.

5. The chewable formulation according to claim 3, wherein when a binder is included, the binder comprises 0.1, 0.2, 0.3, 0.5, 0.5, 0.6, 0.7, 0.8, 0.9, 1, 2, 3, 4, 5, 6, 7, 8, 9, 0, 11, 12, 13, 14 or 15% by weight of the formulation.

6. The chewable formulation according to claim 3, wherein when a sweetener is included, the sweetener comprises 5, 6, 7, 8, 9, 10, 11, 12, 13, 14, 15, 16, 17, 18, 19, 20, 21, 22, 23, 24, 25, 26, 27, 28, 29 or 30% by weight of the formulation.

7. The chewable formulation according to claim 3, wherein when a flavouring agent is included, the flavouring agent comprises 1, 2, 3, 4, 5, 6, 7, 8, 9, 10, 11, 12, 13, 14 or 15% by weight of the formulation.

8. The chewable formulation according to claim 3, wherein when a plasticizer is included, the plasticizer comprises 5, 6, 7, 8, 9, 10, 11, 12, 13, 14, 15, 16, 17, 18, 19, 20, 21, 22, 23, 24, 25, 26, 27, 28, 29 or 30% by weight of the formulation.

9. The chewable formulation according to claim 3, wherein when a humectant is included, the humectant comprises 0.2, 0.3, 0.4, 0.5, 0.6, 0.7, 0.8, 0.9, 1, 2, 3, 4 or 5% by weight of the formulation.

10. The chewable formulation according to claim 3, wherein the humectant is in a solid form.

11. The chewable formulation according to claim 3, wherein the humectant is selected from propylene glycol and glycerine.

12. The chewable formulation according to claim 3, wherein when a lubricant is included, the lubricant comprises 2, 3, 4, 5, 6, 7, 8, 9, 10, 11, 12, 13, 14, 15, 16, 17, 18% by weight of the formulation.

13. The chewable formulation according to claim 3, wherein when a lubricant is included, the lubricant comprises about 0.1% by weight of the formulation.

14. The chewable formulation according to claim 3, wherein when a disintegrating agent is included, the disintegrating agent comprises 1, 2, 3, 4, 5, 6, 7, 8, 9, 10, 11, 12, 13, 14 or 15% by weight of the formulation.

15. The chewable formulation according to claim 3, wherein when a fat and or a lipid is included, the fat and/or lipid comprises 2, 3, 4, 5, 6, 7, 8, 9, 10, 11, 12, 13, 14, 15, 16, 17, 18% by weight of the formulation.

16. The chewable formulation according to claim 1, wherein the chewable formulation provides at least 12 months shelf life.

17. The chewable formulation according to claim 1, wherein the chewable formulation delivers at least 80% of the active ingredient loading within 50 minutes of administration to the target animal.

18. The chewable formulation according to claim 1, wherein the water activity ($a_w$) of the chewable formulation is less than 0.93.

19. A shelf stable chewable formulation, comprising:
a nutritional or pharmaceutically active agent; and
a plasticiser, and
wherein the formulation is formed by extrusion and the water activity ($a_w$) of the chewable formulation is less than 0.93.

20. The chewable formulation according to claim 19, wherein the pharmaceutically active agent is selected from anesthetics, corticosteroids, NSAIDS, antibiotics, antiemetics, anti-thyroidal agents or anti-parasiticidal agents, or any combination of any two or more thereof.

21. The chewable formulation according to claim 19, wherein the chewable formulation further comprises a component selected from the group consisting of a filler, a diluent, a binder, a sweetener, a flavouring agent, a plasticizer, a humectant, a fat, a lipid, an antioxidant, a colouring agent, a disintegrating agent, a preservative, a buffering agent, and any combination thereof.

22. The chewable formulation according to claim 19, wherein when a filler is included, the filler comprises 2, 4, 6, 8, 10, 12, 14, 16, 18, 20, 22, 24, 26, 28, 30, 32, 34, 36, 38 or 40% by weight of the formulation.

23. The chewable formulation according to claim 19, wherein when a binder is included, the binder comprises 0.1, 0.2, 0.3, 0.5, 0.5, 0.6, 0.7, 0.8, 0.9, 1, 2, 3, 4, 5, 6, 7, 8, 9, 0, 11, 12, 13, 14 or 15% by weight of the formulation.

24. The chewable formulation according to claim 19, wherein when a sweetener is included, the sweetener comprises 5, 6, 7, 8, 9, 10, 11, 12, 13, 14, 15, 16, 17, 18, 19, 20, 21, 22, 23, 24, 25, 26, 27, 28, 29 or 30% by weight of the formulation.

25. The chewable formulation according to claim 19, wherein when a flavouring agent is included, the flavouring agent comprises 1, 2, 3, 4, 5, 6, 7, 8, 9, 10, 11, 12, 13, 14 or 15% by weight of the formulation.

26. The chewable formulation according to claim 19, wherein when a plasticizer is included, the plasticizer comprises 5, 6, 7, 8, 9, 10, 11, 12, 13, 14, 15, 16, 17, 18, 19, 20, 21, 22, 23, 24, 25, 26, 27, 28, 29 or 30% by weight of the formulation.

27. The chewable formulation according to claim 19, wherein when a humectant is included, the humectant comprises 0.2, 0.3, 0.4, 0.5, 0.6, 0.7, 0.8, 0.9, 1, 2, 3, 4 or 5 % by weight of the formulation.

28. The chewable formulation according to claim 19, wherein the humectant is in a solid form.

29. The chewable formulation according to claim 19, wherein the humectant is selected from propylene glycol and glycerine.

30. The chewable formulation according to claim 19, wherein when a lubricant is included, the lubricant comprises 2, 3, 4, 5, 6, 7, 8, 9, 10, 11, 12, 13, 14, 15, 16, 17, 18% by weight of the formulation.

31. The chewable formulation according to claim 19, wherein when a lubricant is included, the lubricant comprises about 0.1% by weight of the formulation.

32. The chewable formulation according to claim 19, wherein when a disintegrating agent is included, the disintegrating agent comprises 1, 2, 3, 4, 5, 6, 7, 8, 9, 10, 11, 12, 13, 14 or 15% by weight of the formulation.

33. The chewable formulation according to claim 19, wherein when a fat and or a lipid is included, the fat and/or lipid comprises 2, 3, 4, 5, 6, 7, 8, 9, 10, 11, 12, 13, 14, 15, 16, 17, 18% by weight of the formulation.

34. The chewable formulation according to claim 19, wherein at least 95, 96, 97, 98, 99% by weight of any water present in the chewable formulation is present in a bound state.

35. The chewable formulation according to claim 19, wherein the chewable formulation provides at least 12 months shelf life.

36. The chewable formulation according to claim 19, wherein the chewable formulation delivers at least 80% of the active ingredient loading within 50 minutes of administration to the target animal.

37. A shelf stable chewable formulation, comprising:
a nutritional or pharmaceutically active agent; and
a plasticiser; and wherein
the chewable formulation is formed by extrusion;
at least 95, 96, 97, 98, or 99% by weight of any water present in the chewable formulation is present in a bound state;
the chewable formulation provides at least 12 months shelf life;
the chewable formulation delivers at least 80% of the active ingredient loading within 50 minutes of administration to the target animal; and
the water activity ($a_w$) of the chewable formulation is less than 0.93.

* * * * *